US012220288B2

(12) United States Patent
Chekh et al.

(10) Patent No.: US 12,220,288 B2
(45) Date of Patent: Feb. 11, 2025

(54) SYSTEMS AND METHODS FOR ORTHODONTIC AND RESTORATIVE TREATMENT PLANNING

(71) Applicant: Align Technology, Inc., San Jose, CA (US)

(72) Inventors: Dmitry Yurievich Chekh, Moscow (RU); David Patrick Lopes, El Dorado Hills, CA (US); Vladislav Andreevich Miryaha, Dolgoprudny (RU); Elena Agilina, New York, NY (US); Boris Aleksandrovich Vysokanov, Moscow (RU); Vera Vladimirovna Kadrul, Moscow (RU); Anastasia Chikhanova, Moscow (RU); Aleksei Lisitsin, Chelyabinsk (RU); Valery Prokoshev, Vladimir (RU); Travis Harrison, San Clemente, CA (US); Akhil Deshpande, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 168 days.

(21) Appl. No.: 18/050,284

(22) Filed: Oct. 27, 2022

(65) Prior Publication Data
US 2023/0132201 A1 Apr. 27, 2023

Related U.S. Application Data

(60) Provisional application No. 63/374,802, filed on Sep. 7, 2022, provisional application No. 63/265,010, filed
(Continued)

(51) Int. Cl.
*A61C 13/00* (2006.01)
*A61B 5/00* (2006.01)
(Continued)

(52) U.S. Cl.
CPC ........ *A61C 13/0004* (2013.01); *A61B 5/0088* (2013.01); *A61C 7/002* (2013.01);
(Continued)

(58) Field of Classification Search
CPC ...... A61C 13/0004; A61C 7/002; G06T 19/20
See application file for complete search history.

(56) References Cited

U.S. PATENT DOCUMENTS 5,975,893 A 11/1999 Chishti et al.
6,227,850 B1 5/2001 Chishti et al.
(Continued)

OTHER PUBLICATIONS

International Search Report and Written Opinion for International Application No. PCT/US2022/078761 mailed May 16, 2023, 26 pages.
(Continued)

*Primary Examiner* — Phong X Nguyen
(74) *Attorney, Agent, or Firm* — FORTEM IP LLP

(57) ABSTRACT

Systems and methods for planning a treatment for a patient's teeth are provided. In some embodiments, a method includes receiving input data representing an initial tooth arrangement of a patient's teeth. The method can include determining a target tooth arrangement for the patient's teeth, the target tooth arrangement including a change in mass of at least one tooth. The method can also include generating a plurality of intermediate tooth arrangements configured to adjust the patient's teeth from the initial tooth arrangement toward the target tooth arrangement. The method can further include generating instructions to output a visualization showing a difference in tooth mass between at least one intermediate tooth arrangement of the plurality of intermediate tooth arrangements and the target tooth arrangement.

20 Claims, 41 Drawing Sheets
(7 of 41 Drawing Sheet(s) Filed in Color)

Related U.S. Application Data on Dec. 6, 2021, provisional application No. 63/263,139, filed on Oct. 27, 2021.

(51) Int. Cl.

| | |
|---|---|
| *A61C 7/00* | (2006.01) |
| *A61C 9/00* | (2006.01) |
| *A61C 13/34* | (2006.01) |
| *G06T 7/00* | (2017.01) |
| *G06T 19/20* | (2011.01) |
| *G06V 20/40* | (2022.01) |
| *G06V 40/16* | (2022.01) |
| *G16H 20/40* | (2018.01) |

(52) U.S. Cl.
CPC ............ *A61C 9/0053* (2013.01); *A61C 13/34* (2013.01); *G06T 7/0012* (2013.01); *G06T 7/0014* (2013.01); *G06T 19/20* (2013.01); *G06V 20/46* (2022.01); *G06V 40/161* (2022.01); *G06V 40/171* (2022.01); *G16H 20/40* (2018.01); *G06T 2200/24* (2013.01); *G06T 2207/10016* (2013.01); *G06T 2207/20084* (2013.01); *G06T 2207/30036* (2013.01); *G06T 2207/30201* (2013.01); *G06T 2210/41* (2013.01); *G06T 2219/2004* (2013.01); *G06T 2219/2021* (2013.01)

(56) References Cited

U.S. PATENT DOCUMENTS

| | | |
|---|---|---|
| 6,227,851 B1 | 5/2001 | Chishti et al. |
| 6,299,440 B1 | 10/2001 | Phan et al. |
| 6,309,215 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,450,807 B1 | 9/2002 | Chishti et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 6,830,450 B2 | 12/2004 | Knopp et al. |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,192,273 B2 | 3/2007 | McSurdy, Jr. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,545,221 B2 | 10/2013 | Stone-Collonge et al. |
| 8,562,338 B2 | 10/2013 | Kitching et al. |
| 8,591,225 B2 | 11/2013 | Wu et al. |
| 8,788,285 B2 | 7/2014 | Kuo |
| 8,807,999 B2 | 8/2014 | Kuo et al. |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 9,700,385 B2 | 7/2017 | Webber |
| 9,844,424 B2 | 12/2017 | Wu et al. |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,537,406 B2 | 1/2020 | Wu et al. |
| 10,595,966 B2 | 3/2020 | Carrier, Jr. et al. |
| 10,617,489 B2 | 4/2020 | Grove et al. |
| 10,706,321 B1 * | 7/2020 | Chen .................... G06T 3/4007 |
| 10,722,328 B2 | 7/2020 | Velazquez et al. |
| 10,758,321 B2 | 9/2020 | Stone-Collonge et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,912,629 B2 | 2/2021 | Tanugula et al. |
| 10,973,611 B2 | 4/2021 | Pokotilov et al. |
| 10,993,782 B1 * | 5/2021 | Raslambekov ......... G06T 19/00 |
| 10,993,783 B2 | 5/2021 | Wu et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,045,283 B2 | 6/2021 | Riley et al. |
| 11,071,608 B2 | 7/2021 | Derakhshan et al. |
| 11,096,763 B2 | 8/2021 | Akopov et al. |
| 11,103,330 B2 | 8/2021 | Webber et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,154,381 B2 | 10/2021 | Roschin et al. |
| 11,259,896 B2 | 3/2022 | Matov et al. |
| 11,357,598 B2 | 6/2022 | Cramer |
| 11,395,717 B2 | 7/2022 | Yuryev et al. |
| 11,432,908 B2 | 9/2022 | Kopelman et al. |
| 11,464,604 B2 | 10/2022 | Makarenkova et al. |
| 11,478,334 B2 | 10/2022 | Matov et al. |

(56) References Cited

U.S. PATENT DOCUMENTS

| | | |
|---|---|---|
| 11,484,389 B2 | 11/2022 | Sterental et al. |
| 11,521,732 B2 | 12/2022 | Levin et al. |
| 11,534,272 B2 | 12/2022 | Li et al. |
| 11,553,988 B2 | 1/2023 | Mednikov et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2014/0335470 A1* | 11/2014 | Fisker ................... G06F 30/00 700/98 |
| 2014/0342304 A1 | 11/2014 | Meletiou, Jr. |
| 2015/0305669 A1* | 10/2015 | Hultgren ............... A61C 19/05 433/215 |
| 2016/0004811 A1* | 1/2016 | Somasundaram ..... G06V 40/10 703/11 |
| 2016/0220200 A1* | 8/2016 | Sandholm ............ A61B 5/4848 |
| 2016/0310235 A1 | 10/2016 | Derakhshan et al. |
| 2017/0135792 A1 | 5/2017 | Webber |
| 2017/0135793 A1 | 5/2017 | Webber et al. |
| 2017/0165032 A1 | 6/2017 | Webber et al. |
| 2017/0273760 A1 | 9/2017 | Morton et al. |
| 2017/0372032 A1* | 12/2017 | Kuo ....................... A61C 7/002 |
| 2018/0153648 A1 | 6/2018 | Shanjani et al. |
| 2018/0280118 A1 | 10/2018 | Cramer |
| 2019/0000593 A1 | 1/2019 | Cam et al. |
| 2019/0029784 A1 | 1/2019 | Moalem et al. |
| 2019/0046297 A1 | 2/2019 | Kopelman et al. |
| 2019/0060034 A1* | 2/2019 | Hultgren ................ A61C 19/05 |
| 2019/0266796 A1* | 8/2019 | Comer ................... G06T 17/20 |
| 2019/0298494 A1 | 10/2019 | Webber et al. |
| 2019/0314119 A1 | 10/2019 | Kopelman et al. |
| 2019/0328487 A1 | 10/2019 | Levin et al. |
| 2019/0328488 A1 | 10/2019 | Levin et al. |
| 2020/0107915 A1 | 4/2020 | Roschin et al. |
| 2020/0155274 A1 | 5/2020 | Pimenov et al. |
| 2020/0281697 A1* | 9/2020 | Brandt ................... G16H 30/20 |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0360109 A1 | 11/2020 | Gao et al. |
| 2020/0390522 A1* | 12/2020 | Pokotilov ............. A61C 7/002 |
| 2021/0073998 A1 | 3/2021 | Brown et al. |
| 2021/0134436 A1 | 5/2021 | Meyer et al. |
| 2021/0174477 A1 | 6/2021 | Shi et al. |
| 2021/0259809 A1 | 8/2021 | O'Leary et al. |
| 2022/0071740 A1* | 3/2022 | Raslambekov ......... G06T 17/10 |
| 2022/0148263 A1* | 5/2022 | Vannahme .............. G06T 17/20 |
| 2022/0270762 A1* | 8/2022 | Crawford ............... G16H 50/50 |
| 2022/0304774 A1* | 9/2022 | Wratten, Jr. ........... B33Y 80/00 |
| 2022/0323190 A1 | 10/2022 | Kopelman et al. |
| 2023/0132201 A1* | 4/2023 | Chekh .................. G06T 7/0012 345/419 |
| 2023/0270526 A1* | 8/2023 | Choi ..................... A61C 13/34 433/24 |

OTHER PUBLICATIONS

Kazemi et al., "One Millisecond Face Alignment with an Ensemble of Regression Trees," KTH, Royal Institute of Technology, Computer Vision and Active Perception Lab, 8 pages.

"Take motion photos & use Top Shot on your Pixel phone," Google Camera Help, 2 pages.

Visin et al., "ReNet: A Recurrent Neural Network Based Alternative to Convolutional Networks," Jul. 23, 2015, 9 pages.

* cited by examiner

*18 *19 *20 *21 *22       *23 *24 *25 *26 *27

*37 *38 *39 *40   *28    *43 *44 *45 *46
*42 *41                   *48 *47

*1                *29                              *17

*30

*2                                                 *16
                  *31
              *32 *34 *36
*3            *33  *35                             *15

*51 *52 *53
      *50 *62 *63 *64 *54
*4  *49 *61         *65 *55                        *14
      *60 *68 *67 *66 *56
         *59 *58 *57
*5                                                 *13

*6                                      *12

*7                  *11

*8    *9    *10

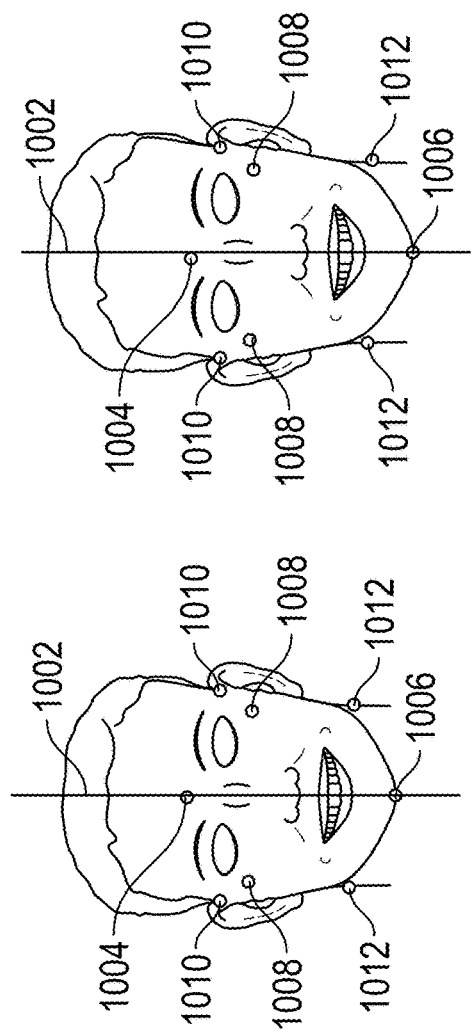
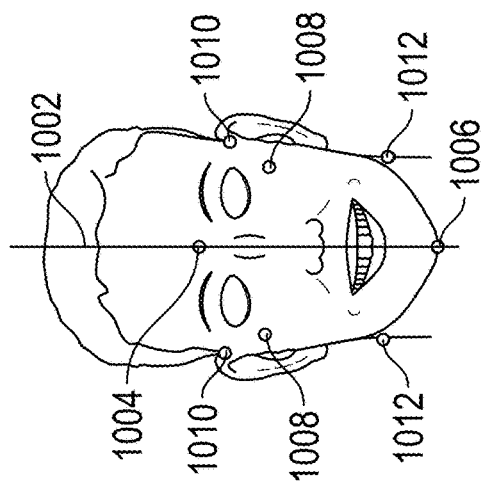
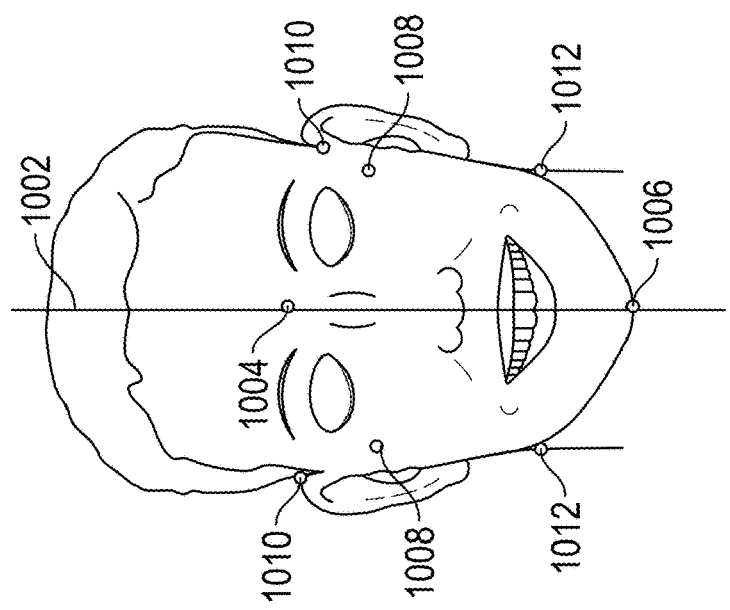
FIG. 10A
FIG. 10B
FIG. 10C
FIG. 10D

SYSTEMS AND METHODS FOR ORTHODONTIC AND RESTORATIVE TREATMENT PLANNING

CROSS-REFERENCE TO RELATED APPLICATION(S)

The present application claims the benefit of priority to U.S. Provisional Application No. 63/263,139, filed Oct. 27, 2021; U.S. Provisional Application No. 63/265,010, filed Dec. 6, 2021; and U.S. Provisional Application No. 63/374,802, filed Sep. 7, 2022; each of which is incorporated by reference herein in its entirety.

TECHNICAL FIELD

The present technology generally relates to treatment planning, and in particular, to systems and methods for orthodontic and restorative treatment planning.

BACKGROUND

The aesthetics and/or function of a patient's teeth may be compromised if one or more teeth are chipped, broken, worn down through grinding or other means, or simply malformed. Restorative treatment procedures can be used to repair or correct the shape of a patient's tooth, such as by applying a restorative object to the tooth and/or by removing portions of the tooth. However, patients may be reluctant to undergo restorative treatment for malformed or injured teeth due to the invasive nature of such procedures. Additionally, excessive tooth mass reduction during a restorative treatment procedure may compromise the integrity and vitality of the tooth, thus increasing the risk of complications such as fracture and tooth loss. Accordingly, improved approaches for reducing the invasiveness of restorative treatments are needed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale. Instead, emphasis is placed on illustrating clearly the principles of the present disclosure.

FIG. 10A illustrates facial landmarks that can be used to determine a face type, in accordance with embodiments of the present technology.

FIGS. 10B-10D illustrate representative examples of face types, in accordance with embodiments of the present technology.

DETAILED DESCRIPTION

Figure 1:
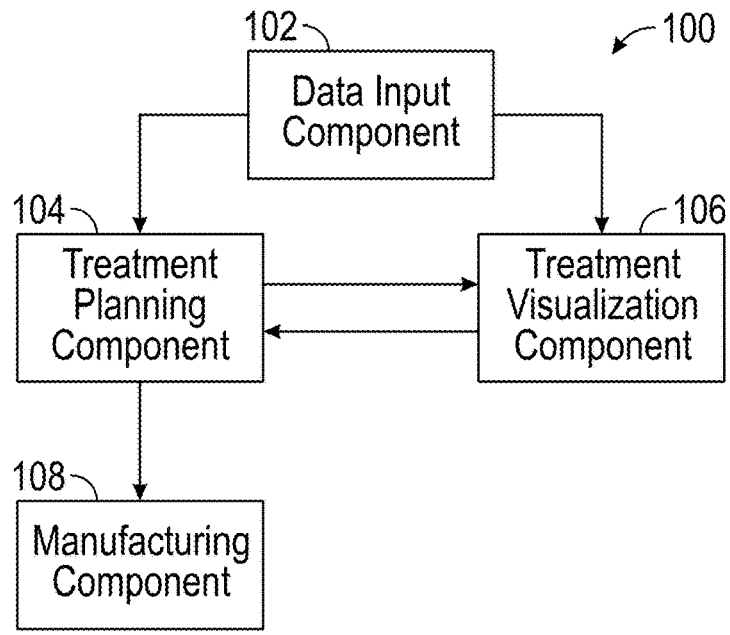
FIG. 1 is a schematic block diagram illustrating a system for treatment planning, in accordance with embodiments of the present technology.

The present technology relates to systems, methods, and devices for planning a combined orthodontic and restorative treatment, also referred to herein as an "orthodontic-restorative" or "ortho-restorative" treatment. In some embodiments, an ortho-restorative treatment plan includes (1) repositioning one or more teeth and (2) altering the mass of one or more teeth, such as by applying restorative objects (e.g., crowns, veneers, edge bonding, composites, implants, prosthetics) to one or more teeth and/or removing portions of one or more teeth. Ortho-restorative treatments may be less invasive compared to conventional restorative-only treatments because orthodontic repositioning of the teeth may decrease the amount of tooth mass addition and/or reduction needed to achieve the treatment target. Additionally, ortho-restorative treatments may be faster than conventional orthodontics-only treatments because modifying the patient's tooth mass may reduce the amount of orthodontic repositioning needed to achieve the treatment target.

In some embodiments, for example, a method for ortho-restorative treatment planning includes receiving input data representing an initial tooth arrangement of a patient's teeth, and outputting a visualization of a treatment plan for achieving a target tooth arrangement for the patient's teeth. The target tooth arrangement can include a change in mass of at least one tooth. The visualization can show a plurality of intermediate tooth arrangements configured to move the patient's teeth from the initial tooth arrangement toward the target tooth arrangement. The visualization can also show a difference in tooth mass between at least one intermediate tooth arrangement and the target tooth arrangement. Accordingly, a user (e.g., clinician, technician, patient) can use the visualization to evaluate the invasiveness, duration, and/or efficacy of the ortho-restorative treatment plan. The visualization can also allow the user to quickly assess the effects of any changes to the orthodontic and/or restorative aspects of the treatment plan, thus allowing the treatment plan to be customized to the particular patient's goals and preferences. For example, a patient may opt for additional orthodontic treatment stages to reduce the invasiveness of the restorative procedure, or the patient may be willing to undergo larger amounts of tooth mass reduction and/or addition to decrease the time to achieve the target tooth arrangement.

The present technology can provide many advantages over conventional treatment planning approaches. For example, orthodontic work and restoration work are conventionally planned in silos as two disconnected tasks, even though better patient outcomes may be achieved through a combination of both treatments. In some instances, restorative work may benefit from a prior orthodontic setup to achieve the best functional and/or aesthetic results for the patient. However, conventional systems and methods lack integrations that allow for concurrent planning of ortho-restorative procedures, which can result in cumbersome and disconnected workflows, more difficulties in planning combined procedures and/or communicating the benefits of such procedures to the patient, multiple iterations between clinicians and treatment providers to achieve a sufficiently good result for the patient, inefficiency, and/or poorer patient outcomes.

To address these and other challenges, the present technology can provide an integrated ortho-restorative workflow and software platform that allows users to plan orthodontic therapy and restorative work concurrently. For example, the present technology can allow the user to determine an orthodontic treatment plan that provides improved tooth positioning for subsequent restorative procedures (e.g., reduces the invasiveness of tooth mass modifications needed). Accordingly, the present technology can provide better product relevance, improved patient outcomes, more convenient workflows, improved adoption for interdisciplinary practices, and/or flexibility for support by partnered laboratories and/or manufacturers.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

As used herein, the terms "vertical," "lateral," "upper," and "lower" can refer to relative directions or positions of features of the embodiments disclosed herein in view of the orientation shown in the Figures. For example, "upper" or "uppermost" can refer to a feature positioned closer to the top of a page than another feature. These terms, however, should be construed broadly to include embodiments having other orientations, such as inverted or inclined orientations where top/bottom, over/under, above/below, up/down, and left/right can be interchanged depending on the orientation.

The headings provided herein are for convenience only and do not interpret the scope or meaning of the claimed present technology. Embodiments under any one heading may be used in conjunction with embodiments under any other heading.

I. Systems and Methods for Ortho-Restorative Treatment Planning

The present technology provides systems and methods for planning an ortho-restorative treatment for a patient. In some embodiments, an ortho-restorative treatment plan includes: (1) an orthodontic treatment procedure in which one or more teeth are repositioned from an initial tooth arrangement toward a target tooth arrangement, and (2) a restorative treatment procedure in which the shape of one or more existing teeth is modified and/or one or more missing teeth are replaced. The orthodontic and restorative treatment procedures can be performed sequentially (e.g., all tooth repositioning is performed before any restorative treatments are performed, or vice-versa), concurrently (e.g., any particular stage of the treatment plan can include both tooth repositioning and restorative treatment), or suitable combinations thereof.

The orthodontic treatment procedure can involve applying a series of orthodontic appliances that are configured to incrementally move the teeth through a series of intermediate tooth arrangements. Some or all of the orthodontic appliances can include a polymeric shell including a plurality of teeth-receiving cavities configured to receive and resiliently reposition the teeth toward a particular intermediate tooth arrangement. Additional details and examples of orthodontic appliances suitable for use with the present technology are provided in Section II below.

The restorative treatment procedure can involve applying at least one restorative object to the patient's arch to increase a mass of an existing tooth or replace a missing tooth ("tooth mass addition"), removing a portion of an existing tooth ("tooth mass reduction"), or suitable combinations thereof. Examples of restorative objects (also referred to herein as "restoratives" or "restorations") include, but are not limited to, crowns, veneers, edge bonding, composites, implants, and prosthetics. In some instances, to aid the fitting of the restorative object over an existing tooth, a portion of the tooth can be removed to provide a mounting surface to receive the restorative object. Different types of restorative objects may require differing amounts of tooth reduction (e.g., a veneer may require less tooth mass reduction than a crown). The amount of tooth mass reduction can also vary depending on the position of the tooth. Optionally, one or more neighboring teeth may also undergo tooth mass reduction to provide space for the restorative object.

FIG. 1 is a schematic block diagram illustrating a system 100 for treatment planning, in accordance with embodiments of the present technology. The system 100 can be configured to provide a software platform that provides a single ecosystem for planning and visualizing ortho-restorative treatment procedures and/or other procedures performed on the patient's craniofacial region. The system 100 includes a data input component 102, a treatment planning component 104, a treatment visualization component 106, and a manufacturing component 108.

The data input component 102 is configured to receive patient data from one or more input devices. The patient data can include any data relevant to a treatment procedure for the patient. For example, the patient data can include data of the patient's teeth, gingiva, arch, intraoral cavity, jaws, face, and/or any other hard or soft tissues of the craniofacial region. The patient data can include photographs, videos, scan data (e.g., intraoral and/or extraoral scans), magnetic resonance imaging (MRI) data, radiographic data (e.g., standard x-ray data such as bitewing x-ray data, panoramic x-ray data, cephalometric x-ray data, computed tomography (CT) data, cone-beam computed tomography (CBCT) data, fluoroscopy data), motion data, and the like. The patient data can include 2D data (e.g., 2D photographs or videos), 3D data (e.g., 3D photographs, intraoral and/or extraoral scans, digital models), 4D data (e.g., fluoroscopy data, dynamic articulation data, hard and/or soft tissue motion capture data), or suitable combinations thereof.

The data input component 102 can be operably coupled to various peripheral devices (not shown) in order to receive patient data therefrom. The peripheral devices can be associated with and/or operated by a healthcare provider (e.g., a clinician), a technician, a patient, or any other suitable user. The peripheral devices can be or include a computing device (e.g., personal computer, laptop, workstation, server, mobile device) that receives, stores, and/or processes the patient data for transmission to the data input component 102. The patient data can be transmitted to the data input component 102 via any suitable combination of wired and/or wireless communication methods.

In some embodiments, for example, the data input component 102 receives data from a scanner configured to obtain a 3D digital representation (e.g., images, surface topography data) of a patient's teeth, such as via direct intraoral scanning or indirectly via casts, impressions, models, etc. The scanner can include a probe (e.g., a handheld probe) for optically capturing 3D structures (e.g., by confocal focusing of an array of light beams). Examples of scanners suitable for use with the system 100 include, but are not limited to, the iTero® intraoral digital scanner manufactured by Align Technology, Inc., the 3M True Definition Scanner, and the Cerec Omnicam manufactured by Sirona®. The data obtained by the scanner can be transmitted to a clinician's computing device, which in turn can transmit the data to the data input component 102.

As another example, the data input component 102 can receive patient data from a mobile device (e.g., smartphone, tablet) associated with a patient. In some embodiments, the mobile device includes or is operably coupled to an imaging device (e.g., a camera) that generates 2D and/or 3D image data (e.g., photographs, video) of a patient's teeth, arch, face, head, etc. The mobile device can implement a mobile application that instructs the patient to capture images from one or more views, such as a profile view of the patient's head, a front view of the patient's head with a neutral expression, a front view of the patient's head while smiling, a view of the upper jaw, a view of the lower jaw, a right buccal view with the jaw closed, an anterior view with the jaw closed, a left buccal view with the jaw closed, a right buccal view with the jaw open, an anterior view with jaw open, and/or a left buccal view with the jaw open. Optionally, the mobile application can instruct the patient to capture a video, such as video data showing the patient smiling, speaking, moving their jaws, turning their head, etc. The mobile application can then transmit the image data to the data input component 102.

The treatment planning component 104 is configured to generate a treatment plan for the patient, based on the patient data from the data input component 102. As previously discussed, the treatment plan can include an orthodontic treatment, a restorative treatment, or a combined ortho-restorative treatment. In some embodiments, for example, the treatment planning component 104 is configured to receive a digital representation of an initial tooth arrangement of a patient from the data input component 102. The treatment planning component 104 can then determine a target tooth arrangement to be achieved via orthodontic and/or restorative treatment. The target tooth arrangement can be an arrangement of the patient's teeth that achieves a desired aesthetic and/or functional treatment goal (e.g., correct malocclusions, repair missing, malformed, and/or damaged teeth). Optionally, the target tooth arrangement can be determined based at least in part on patient data, such as a photograph of the patient's smile. The treatment planning component 104 can then generate a treatment plan for achieving the target tooth arrangement, such as a series of intermediate tooth arrangements configured to reposition the teeth from the initial tooth arrangement toward the target tooth arrangement and/or one or more tooth mass modifications. The target tooth arrangement and treatment plan can be determined manually based on input from a technician, automatically using software algorithms, or suitable combinations thereof. Additional details of the processes that can be performed by the treatment planning component 104 are described further below.

The treatment visualization component 106 is configured to output a visualization that graphically represents the treatment plan generated by the treatment planning component 104. For example, in embodiments where the treatment plan includes repositioning the patient's teeth from the initial tooth arrangement toward the target tooth arrangement via a series of intermediate tooth arrangements, the treatment visualization component 106 can output a plurality of 3D models showing the initial tooth arrangement, target tooth arrangement, and/or intermediate tooth arrangements. As another example, in embodiments where the treatment plan includes tooth mass addition and/or reduction, the treatment visualization component 106 can show the amounts and/or locations of tooth mass addition and/or reduction. Optionally, the treatment visualization component 106 can also receive and display patient data received from the data input component 102 (e.g., an image of the patient's smile) to provide additional guidance to a user reviewing the treatment plan. In some embodiments, the treatment visualization component 106 displays multiple types of patient data (e.g., 2D, 3D, and/or 4D data) concurrently using graphical user interface elements such as side-by-side views, overlays (e.g., in which each layer can be independently turned on, turned off, or adjusted in opacity), animations, etc. This approach allows the user to visualize the planned treatment in different contexts, e.g., with respect to the patient's facial features, soft tissues, hard tissues, jaw articulation, etc. Additional details of the processes that can be performed by the treatment visualization component 106 are described further below.

In some embodiments, the treatment plan produced by the treatment planning component 104 is displayed to a user (e.g., clinician, technician, patient) via the visualization produced by the treatment visualization component 106. The treatment visualization component 106 can also provide user interface tools allowing the user to provide feedback on the treatment plan, as described in detail below. For example, the user can modify the treatment plan, such as by changing the positions of one or more teeth, changing an amount of tooth mass addition and/or reduction, changing the shape of a restorative object, changing the number of treatment stages, etc. The feedback can be used to directly update the treatment plan, or can be transmitted to the treatment planning component 104, which can update the treatment plan accordingly. The updated treatment plan can be transmitted back to the treatment visualization component 106 for further user review. This process can be repeated until the user approves the treatment plan.

Optionally, once the treatment plan is approved, the treatment planning component 104 can transmit instructions (e.g., STL files, CLI files, CAD files) to the manufacturing component 108 for fabricating one or more devices for use with the treatment plan. For example, the manufacturing component 108 can produce a series of orthodontic appliances configured to reposition the patient's teeth from the initial tooth arrangement toward the target tooth arrangement. The manufacturing component 108 can also produce attachments, attachment placement templates, and/or other devices to be used in conjunction with an orthodontic appliance, e.g., to improve control over the forces on the patient's teeth. As another example, the manufacturing component 108 can produce one or more restorative objects to be applied to the patient's arch, such as a crown, vencer, prosthetic, implant, etc. In a further example, the manufacturing component 108 can produce a guide or template to be placed in the patient's intraoral cavity to assist a clinician in performing a treatment procedure, such as preparing a tooth for a restorative object, performing tooth mass addition or reduction, placing an attachment or restorative object on a tooth, etc.

In some embodiments, the manufacturing component 108 is configured to fabricate the device(s) using an additive manufacturing technique. Additive manufacturing (also referred to herein as "3D printing") includes a variety of technologies which fabricate 3D objects directly from digital models through an additive process. In some embodiments, additive manufacturing includes depositing a precursor material (e.g., a polymeric resin) onto a build platform. The precursor material can be cured, polymerized, melted, sintered, fused, and/or otherwise solidified to form a portion of the object and/or to combine the portion with previously formed portions of the object. In some embodiments, the additive manufacturing techniques provided herein build up the object geometry in a layer-by-layer fashion, with successive layers being formed in discrete build steps. Alternatively or in combination, the additive manufacturing techniques described herein can allow for continuous build-up of an object geometry.

Examples of additive manufacturing techniques suitable for use with the methods described herein include, but are not limited to, the following: (1) vat photopolymerization, in which an object is constructed from a vat of liquid photopolymer resin, including techniques such as stereolithography (SLA), digital light processing (DLP), continuous liquid interface production (CLIP), two-photon induced photopolymerization (TPIP), and volumetric additive manufacturing (VAM); (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer-by-layer, and direct ink writing (DIW); (5) powder bed fusion, including techniques such as direct metal laser sintering (DMLS), electron beam melting (EBM), selective heat sintering (SHS), selective laser melting (SLM), and selective laser sintering (SLS); (6) sheet lamination, including techniques such as laminated object manufacturing (LOM) and ultrasonic additive manufacturing (UAM); and (7) directed energy deposition, including techniques such as laser engineering net shaping, directed light fabrication, direct metal deposition, and 3D laser cladding.

In some embodiments, the system 100 is used to monitor and/or update a treatment plan after the treatment procedure has already started. For example, the data input component 102 can receive patient data indicative of a state of the patient's teeth, gingiva, arch, jaws, face, etc., after the start of treatment. The patient data can be transmitted to the treatment planning component 104 for comparison with the original treatment plan. If the treatment planning component 104 determines that the treatment plan should be modified (e.g., the patient's teeth are off-course), the treatment planning component 104 can generate a revised treatment plan. For example, the revised treatment plan can include modifications to the target tooth arrangement and/or to one or more intermediate tooth arrangements. The revised treatment plan can be transmitted to the treatment visualization component 106 for user review. Once the revised treatment plan is approved, the treatment planning component 104 can send instructions to the manufacturing component 108 to fabricate one or more devices for implementing the revised treatment plan (e.g., new orthodontic appliances, attachments, restorative objects, etc.). This process can be repeated as desired until the patient has achieved the desired treatment goal.

The system 100 illustrated in FIG. 1 can be configured in many different ways. For example, the various components 102-108 of the system 100 can be implemented by one or more computing devices (e.g., a server, personal computer, workstation, mainframe, laptop, mobile device) having software and hardware components (e.g., processors, memory, user input and output devices, network interfaces, etc.) configured to perform the various operations described herein. For example, some or all of the components 102-108 can be implemented as a distributed "cloud" service across any suitable combination of hardware and/or virtual computing resources.

In some embodiments, some or all of the components 102-108 can be disposed on a single computing device and/or can be part of a single communications network. Alternatively, some or all of the components 102-108 can be located on distinct and separate computing devices. The components 102-108 can be operably coupled via one or more communications networks, such as any of the following: a wired network, a wireless network, a metropolitan area network (MAN), a local area network (LAN), a wide area network (WAN), a virtual local area network (VLAN), an internet, an extranet, an intranet, and/or any other suitable type of network or combinations thereof.

Although FIG. 1 illustrates the components 102-108 of the system 100 as being separate functional elements, in other embodiments, some or all of the components 102-108 can be combined. For example, the data input component 102 can be combined with the treatment planning component 104, the treatment planning component 104 can be combined with the treatment visualization component 106, etc. Additionally, any of the components 102-108 can be divided into smaller sub-components, and/or the system 100 can include other components not shown in FIG. 1.

Figure 2:
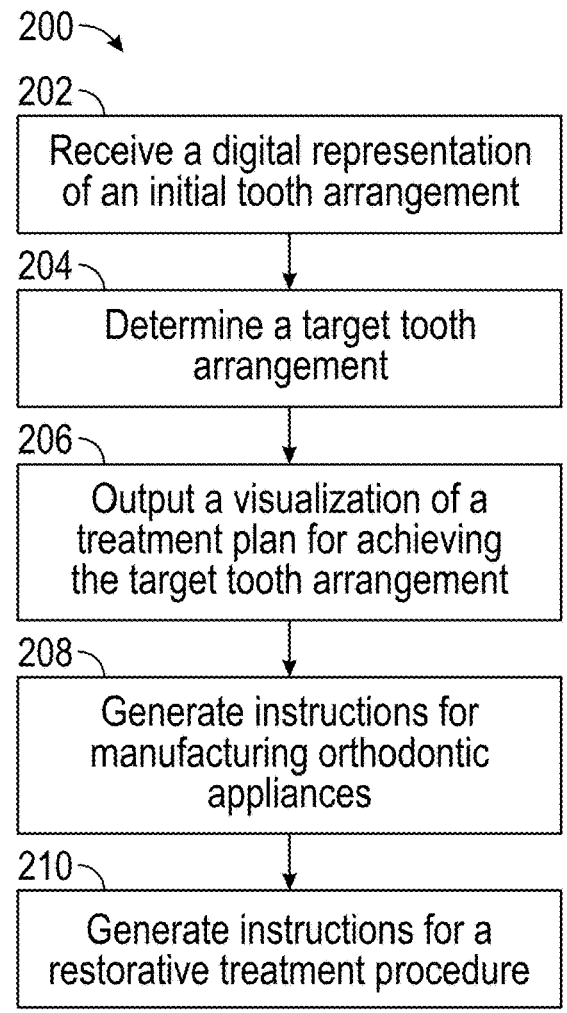
FIG. 2 is a flow diagram illustrating a method for planning an ortho-restorative treatment, in accordance with embodiments of the present technology.

FIG. 2 is a flow diagram illustrating a method 200 for planning an ortho-restorative treatment, in accordance with embodiments of the present technology. The method 200 can be performed using any suitable system or device, such as the system 100 of FIG. 1. In some embodiment, some or all of the processes of the method 200 are implemented as computer-readable instructions (e.g., program code) that are configured to be executed by one or more processors of a computing device.

The method 200 begins at block 202 with receiving a digital representation of an initial tooth arrangement of a patient. In some embodiments, the digital representation is received at a data input component of a software platform for ortho-restorative treatment planning, such as the data input component 102 of the system 100 of FIG. 1. The digital representation can be generated from any of the patient data types described elsewhere herein (e.g., photographs, videos, scan data, MRI data, radiographic data, motion data). For example, in some embodiments, the digital representation is a 3D model generated from intraoral scan data of the patient's teeth, gingiva, and/or other intraoral tissues.

At block 204, the method 200 continues with determining a target tooth arrangement for the patient's teeth. In some embodiments, the target tooth arrangement is determined by a treatment planning component of a software platform for ortho-restorative treatment planning, such as the treatment planning component 104 of the system 100 of FIG. 1. The target tooth arrangement can be a prescribed arrangement of the teeth that meets the patient's desired aesthetic and/or functional treatment goals. For example, the target tooth arrangement can correspond to an improved (e.g., "ideal") arch form and/or smile for the patient. In some embodiments, the process of block 204 involves analyzing the patient's initial tooth arrangement to identify indications to be treated (e.g., maloccluded, malformed, damaged, and/or missing teeth), then determining a target tooth arrangement that would correct some or all of the indications through a combination of orthodontic repositioning and tooth mass modification. For instance, tooth repositioning can be prescribed to correct malocclusions and/or to create space for restorative objects to be applied to the patient's arch. Tooth mass modifications can be prescribed for teeth that are damaged, malformed, missing, or otherwise deviate from the desired shape, and/or to create space for orthodontic movements. Accordingly, the target tooth arrangement can include (1) one or more teeth that have been repositioned (e.g., via tipping, translation, rotation, extrusion, intrusion, root movement) relative to the initial tooth arrangement, and/or (2) one or more teeth that have undergone a change in mass (e.g., tooth mass addition, tooth mass reduction) relative to the initial tooth arrangement.

In some embodiments, the ortho-restorative treatment procedure involves completing all orthodontic repositioning before performing any restorative procedures. In such embodiments, the process of block 204 can involve first determining a desired arrangement of the patient's teeth to be achieved through orthodontic repositioning ("final orthodontic position"). The final orthodontic position can be achieved by incrementally moving the teeth from the initial tooth arrangement through a series of intermediate tooth arrangements, as described elsewhere herein. Subsequently, the process of block 204 can involve determining one or more restorative adjustments to the teeth in the final orthodontic position. For example, the shapes of one or more teeth in the final orthodontic position can be modified via tooth mass addition and/or reduction to conform to a desired shape, such as generic shape selected from a library of tooth shapes. Optionally, the generic shape can be altered (e.g., scaled up, scaled down, other changes in tooth geometry) to avoid collisions, maintain sufficient interproximal spacing, avoid excessive changes in tooth mass that might affect vitality, etc. The resulting tooth arrangement with the restorative adjustments can be the target tooth arrangement for the ortho-restorative treatment plan.

The target tooth arrangement can be determined based on orthodontic principles, a prescription from a clinician, patient preference, and/or other relevant considerations. In some embodiments, the target tooth arrangement is designed at least partly based on the patient's unique facial features, also referred to herein as "facially-driven" treatment planning. Facially-driven treatment planning can include, for example, determining one or more facial lines (e.g., smile lines) corresponding to the patient's unique facial anatomy, using the facial lines to determine a target smile for the patient, then generating a target tooth arrangement that would produce the target smile. Additional details of processes for determining a target smile and/or target tooth arrangement for a patient are provided below.

At block 206, the method 200 can include outputting a visualization of a treatment plan for achieving the target tooth arrangement. As discussed above, the treatment plan can include repositioning one or more teeth, altering the mass of one or more teeth, or suitable combinations thereof. For example, the treatment plan can include a plurality of intermediate tooth arrangements representing orthodontic treatment stages for sequentially repositioning the patient's teeth from the initial tooth arrangement toward the target tooth arrangement. In such embodiments, the visualization can include graphical representations (e.g., 3D models) of the initial tooth arrangement, intermediate tooth arrangements, and target tooth arrangement.

In embodiments where the treatment plan includes modifying the mass of one or more teeth, the visualization can also show a difference in tooth mass between the target tooth arrangement and at least one other tooth arrangement (e.g., the initial tooth arrangement or an intermediate tooth arrangement). For example, the visualization can include a graphical representation depicting the amounts and locations of tooth mass addition and/or reduction at each treatment stage relative to the target tooth arrangement. Accordingly, the visualization can also provide guidance for tailoring the treatment plan to achieve the desired balance of invasiveness, duration, and efficacy.

In some embodiments, the visualization is output by a treatment visualization component of a software platform for ortho-restorative treatment planning, such as the treatment visualization component 106 of the system 100 of FIG. 1. For example, the visualization can be displayed to a user (e.g., clinician, technician, patient) as part of a user interface (UI) of the software platform. The UI can be shown on a display (e.g., screen, monitor) of a computing device (e.g., personal computer, workstation, laptop, mobile device). The computing device can include input devices (e.g., keyboard, pointing device, mouse, scanner, interactive displays, touchpad, joystick) allowing the user to interact with the visualization. For example, the user can interact with the visualization when reviewing the treatment plan (e.g., change viewing angle, zoom in, zoom out, hide/show various components, change the appearance (e.g., color, opacity) of displayed components). As another example, the user can interact with the visualization to provide feedback modifying the treatment plan (e.g., change the positions of one or more teeth, change the location and/or amount of tooth mass modification, change the position of one or more facial lines). Additional details of the UI and associated methods are provided below.

At block 208, the method 200 optionally includes generating instructions for fabricating one or more orthodontic appliances. As described in greater detail elsewhere herein, the orthodontic appliances can be configured to incrementally reposition the patient's teeth from the initial tooth arrangement toward the target tooth arrangement according to the treatment plan. In some embodiments, the instructions are configured for manufacturing the orthodontic appliance using direct fabrication, e.g., by directly printing the appliance in accordance with the various additive manufacturing techniques described herein. In other embodiments, the instructions can be configured for indirect fabrication of the appliance, e.g., by thermoforming the appliance over a mold of the patient's teeth.

At block 210, the method 200 optionally includes generating instructions for a restorative treatment procedure. The instructions can include, for example, instructions to a clinician indicating the locations in the patient's arch where restorative objects are to be added and/or where tooth mass is to be removed (e.g., to correct the shape of a tooth or in preparation for applying a restorative object). Alternatively or in combination, the instructions can include manufacturing instructions for fabricating at least one restorative object. For example, the instructions can include a 3D model or other digital representation of the geometry of the restorative object. The instructions can be configured for manufacturing the restorative object via any suitable technique, such as direct fabrication, indirect fabrication, etc. Optionally, the instructions can be configured for manufacturing a guide or template to be placed in the patient's intraoral cavity to assist a clinician in performing the restorative treatment procedure.

The method 200 can be varied in many different ways. For example, some of the processes shown in FIG. 2 can be omitted (e.g., the processes of block 208 and/or block 210) and/or the method 200 can include additional processes not shown in FIG. 2. Moreover, the method 200 can be combined with any of the other methods described herein.

Figure 3:
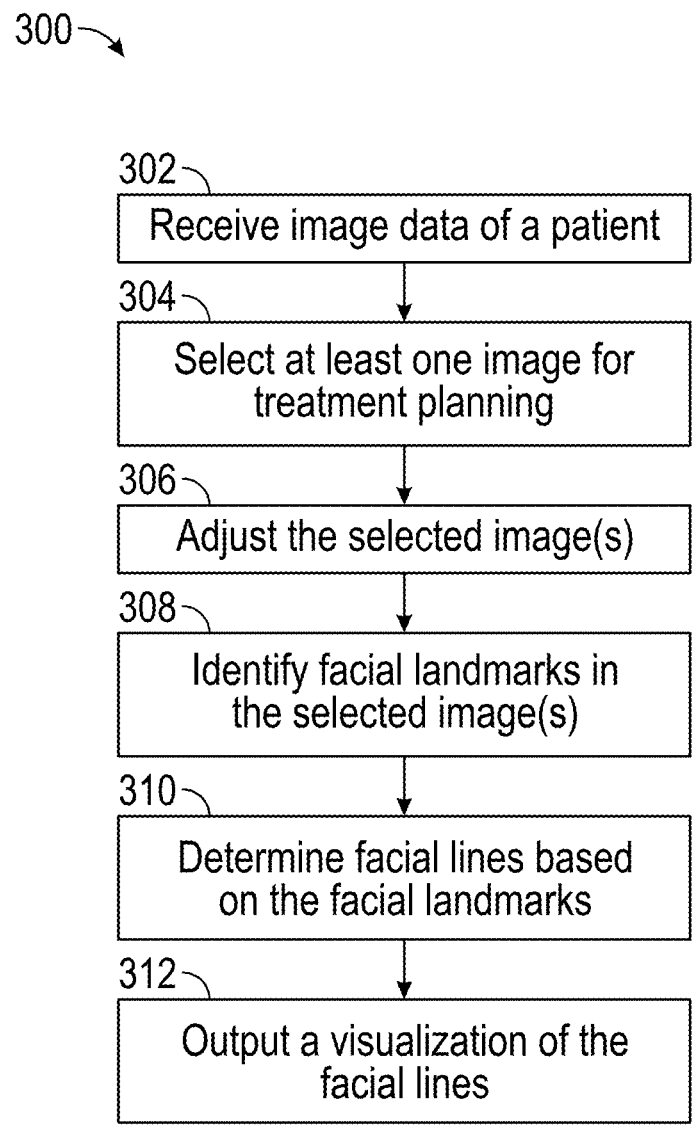
FIG. 3 is a flow diagram illustrating a method for determining facial lines of a patient, in accordance with embodiments of the present technology.

FIG. 3 is a flow diagram illustrating a method 300 for determining facial lines of a patient, in accordance with embodiments of the present technology. In some embodiments, the facial lines correlate to the patient's unique anatomical features and are used as visual guidance to assist a user (e.g., a clinician or technician) in planning a treatment for the patient. For example, smile lines are a type of facial line that can be used to define a target smile for a patient, e.g., a smile that is considered aesthetically pleasing based on the patient's particular facial anatomy. The smile lines can thus be used as a reference when determining a target tooth arrangement for the patient, e.g., the user can select target tooth positions and/or shapes that would cause the patient's smile to conform more closely to the smile lines.

The method 300 can be performed using any suitable system or device. In some embodiment, some or all of the processes of the method 300 are implemented as computer-readable instructions (e.g., program code) that are configured to be executed by one or more processors of a computing device. For example, some or all of the processes of the method 300 can be performed by one or more components of the system 100 of FIG. 1, such as the data input component 102, the treatment planning component 104, and/or the treatment visualization component 106. In some embodiments, the treatment visualization component 106 is or includes a cloud service component that implements a software tool configured to perform some or all of the processes of the method 300. Additionally, some or all of the processes of the method 300 can be performed in a semi-automated or fully automated manner. This approach allows facial lines to be determined according to a clinical protocol, which can improve the consistency and accuracy of ortho-restorative treatment planning across different patients.

The method 300 begins at block 302 with receiving image data of a patient. The image data can depict the patient's anatomy before the start of a treatment procedure and can be used as a reference for treatment planning, as described further below. For example, the image data can include at least one image of the patient's mouth in one or more positions. The patient's mouth can be in a smiling position (e.g., a social smiling position), a repose position with relaxed muscles and lips slightly parted, an anterior retracted open bite or closed bite position, etc. Optionally, the image data can also depict other parts of the patient's anatomy, such as the patient's face, head, neck, shoulders, and/or torso, or the entire body of the patient. For instance, the image data can include at least one image showing the patient's entire face from a frontal view while the patient is smiling ("full-face smile image"). As another example, the image data can include at least one image showing the patient's entire face from a frontal view while the patient's mouth is in a repose position ("full-face repose image"). In a further example, the image data can include at least one intraoral image (e.g., an intraoral anterior image and/or intraoral buccal image).

The image data can be a single image (e.g., a photograph) or can include a plurality of images (e.g., multiple photographs, a video including multiple image frames). Any suitable type of image data can be used, such as 2D images (e.g., photographs), 3D images (e.g., 3D scans), 4D images (e.g., motion capture data), or suitable combinations thereof. The image data can be obtained using any suitable imaging device, such as a camera, scanner, etc. In some embodiments, the image data is obtained using a remote imaging device (e.g., a camera of a patient's mobile device, a DSLR camera) and is subsequently transmitted to an ortho-restorative treatment planning system (e.g., the data input component 102 of the system 100 of FIG. 1).

Optionally, at block 304, the method 300 can include selecting at least one image to be used for treatment planning. This approach can be used in embodiments where the image data includes a plurality of images (e.g., two, three, four, five, 10, 20, 50, or more images). For example, multiple images can be obtained by taking several photographs of the patient or by taking a video of the patient. The process of block 304 can involve selecting one or more of the images that meet certain quality criteria for use in treatment planning. For example, the quality criteria for a full face smile image can include one or more of the following: position of the patient's head (e.g., frontal view), position of the patient's mouth (e.g., wide smile), visibility of the face (e.g., the entire face is visible), visibility of the teeth (e.g., most of the teeth are shown, cutting edges are visible), clarity (e.g., lack of blurriness) of the patient's mouth and/or other facial regions, resolution of the patient's mouth and/or other facial regions, and/or whether the patient's eyes are open. The quality criteria may differ for other types of images (e.g., full-face repose image, intraoral anterior image, intraoral buccal image).

The image selection process of block 304 can be performed in various ways. For example, the image data can be analyzed using computer vision and/or machine learning algorithms to determine whether each image meets the specified quality criteria. In embodiments where a machine learning algorithm is are used, the machine learning algorithm can implement a neural network and/or deep learning model, such as a convolutional neural network (CNN). The machine learning algorithm can be an image classifier that is trained on image data that has been labeled with specific features relevant to image quality (e.g., "head orientation," "blurriness") and/or has been classified as either "suitable" or "unsuitable" for treatment planning purposes. The output of the machine learning algorithm can be a binary classification (e.g., "suitable" or "unsuitable") or can be a score (e.g., a real number between 0 to 1) indicative of the image quality. For example, images having a score above a particular threshold may be selected, while images having a score below the threshold may be rejected. As another example, the images can be ranked based on their score, and one or more of the highest scoring images can be selected.

Optionally, in embodiments where the image data is a temporal sequence of images (e.g., consecutive frames of a video), the temporal information can be taken into account during the image selection process of block 304. For example, if the time interval between images is relatively small, it can be assumed that any changes in patient pose (e.g., head orientation, mouth position), etc., between images would also be relatively small. Accordingly, images that are taken sufficiently close in time to an image in which the patient is in an unsuitable pose may be automatically rejected, since the patient will likely be in the same or a similar unsuitable pose in those images. Optionally, the change in patient pose between images (e.g., head rotation velocity) can be calculated and used to predict which images should be accepted or rejected.

In some embodiments, the image selection process of block 304 is performed in a fully automated manner, e.g., the machine learning algorithm automatically analyzes the image data and selects one or more images to be used for treatment planning. Alternatively, the image selection process can be performed in a semi-automated manner, e.g., the machine learning algorithm automatically analyzes and selects one or more images for review by a user, and the user accepts or rejects the selected images. If none of the images are determined to be of sufficient quality for treatment planning by the machine learning algorithm and/or the user, the user can be instructed to obtain new image data of the patient.

The image selection process of block 304 can provide many advantages. For example, it may be difficult and time-consuming for a user to obtain patient images of sufficient quality by taking individual photographs of the patient. Clinicians may have not enough time to carefully take photographs of the patient and/or re-take photographs if any of them are inappropriate. Moreover, it may be difficult to determine whether the patient is in the proper pose (e.g., correct head orientation and/or mouth opening) for treatment planning purposes. The process of block 304 allows for the automated selection of images from a short video of the patient (or other collection of patient images), thus improving the quality and consistency of images used for treatment planning, while also decreasing the amount of time needed to obtain patient images. Additionally, the image selection process can be highly computationally efficient and can therefore be performed on a mobile device, such as a patient's smartphone or tablet.

Figure 4:
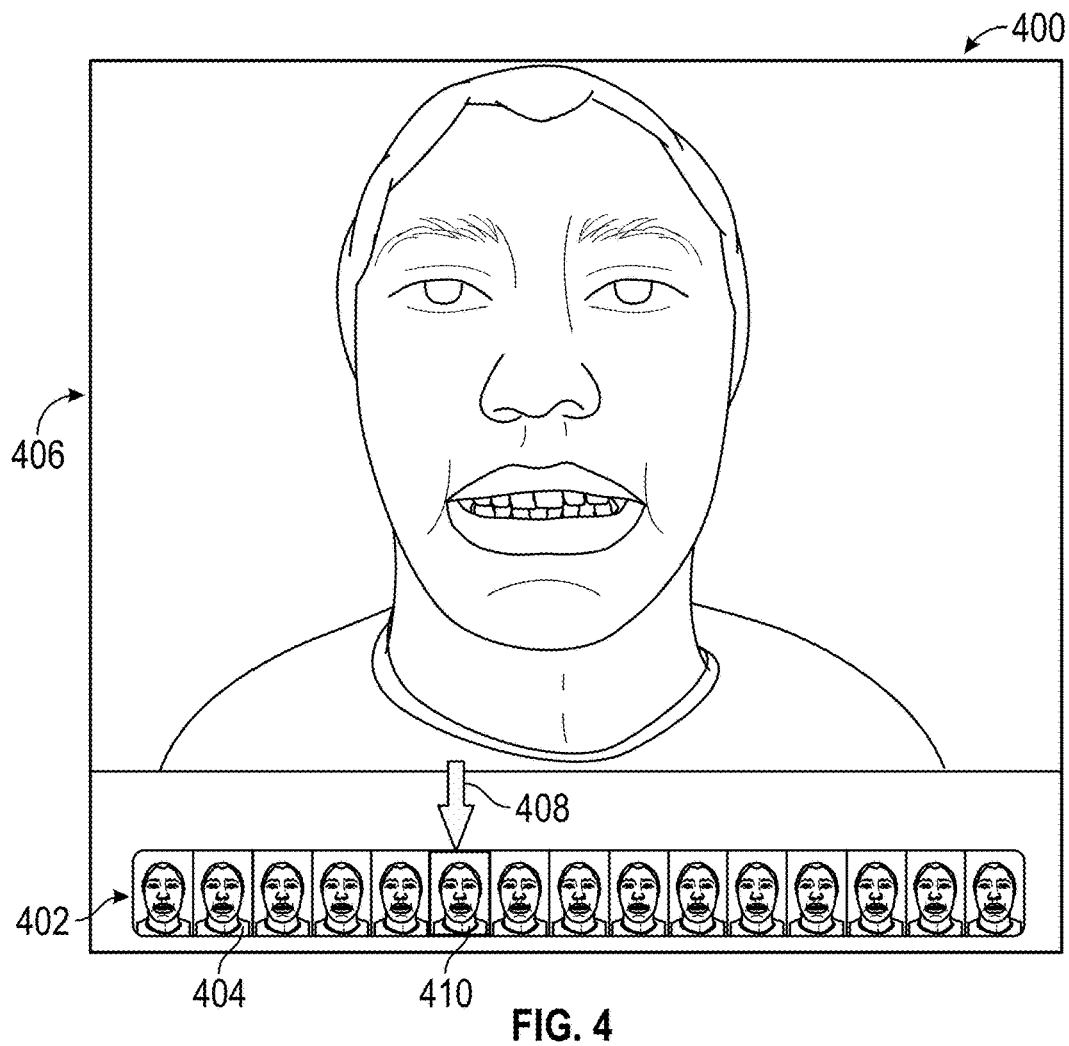
FIG. 4 illustrates a representative example of a user interface for selecting a patient image for treatment planning, in accordance with embodiments of the present technology.

FIG. 4 illustrates a representative example of a UI 400 for selecting a patient image for treatment planning, in accordance with embodiments of the present technology. The UI 400 can be displayed on any suitable computing device, such as a mobile device, personal computer, laptop, workstation, etc. The UI 400 can include an image gallery 402 (e.g., in carousel format) showing a plurality of candidate images 404 of the patient. The UI 400 can also include a viewing panel 406 that allows a user to view a full-sized version of one or more of the candidate images 404.

Once at least one candidate image 404 has been selected for use in treatment planning, in accordance with the process of block 304, the UI 400 can display one more indicators 408 (e.g., arrows, borders, highlighting) showing the selected image 410. Accordingly, the user can review the selected image 410 and/or candidate images 404 via the UI 400. Optionally, the UI 400 can allow the user to approve the selected image 410, reject the selected image 410, choose a different candidate image 404, and/or obtain new candidate images 404.

Referring again to FIG. 3, at block 306, the method 300 can optionally include adjusting the selected image(s). The adjustments can be configured to prepare the image(s) for use in treatment planning and can include any of the following: rotating, translating, cropping, enlarging, shrinking, adjusting color, adjusting contrast, adjusting brightness, increasing sharpness, reducing noise, and/or any other suitable image processing technique. For example, in some embodiments, the adjustment process of block 306 includes rotating a selected image to a vertical orientation, as described below in connection with FIGS. 5-7C.

Figure 5:
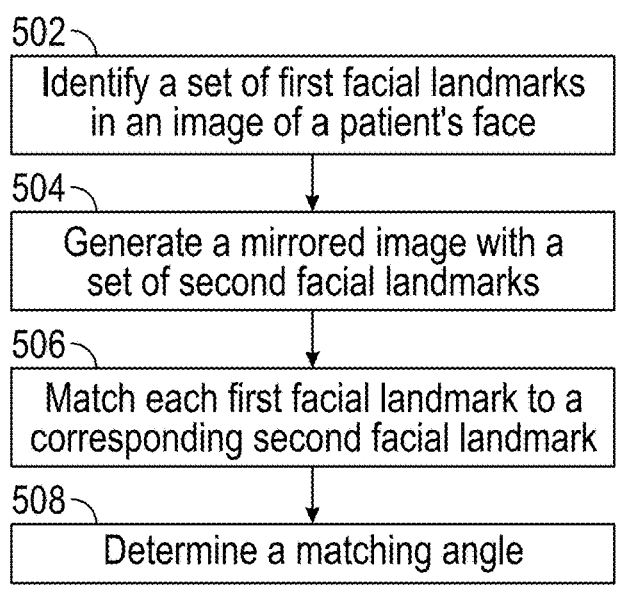
FIG. 5 is a flow diagram illustrating a method for rotating an image to a vertical orientation, in accordance with embodiments of the present technology.
Figure 6A:
FIG. 6A is a photograph of a patient's face in a skewed orientation, in accordance with embodiments of the present technology.
Figure 6B:
FIG. 6B is the photograph of FIG. 6A after being rotated into a vertical orientation, in accordance with embodiments of the present technology.

FIG. 5 is a flow diagram illustrating a method 500 for rotating an image to a vertical orientation, in accordance with embodiments of the present technology. For example, FIG. 6A is a photograph 600a of a patient's face in a skewed orientation (e.g., the patient's midline is not parallel to the vertical axis of the image), and FIG. 6B is the photograph 600b after being rotated into a vertical orientation, in accordance with embodiments of the present technology. In some instances, it may be easier and more accurate to detect facial landmarks and/or determine facial lines when the patient's face is in a vertical orientation. Although a user may manually rotate the image prior to treatment planning, this may introduce inaccuracies due to human error, particularly if the amount of skew is relatively small and/or if the patient's face is asymmetric (e.g., by nature or due to trauma). The method 500 of FIG. 5 can automatically rotate a skewed patient image into a vertical orientation, thus improving the consistency and accuracy of the treatment planning process.

The method 500 begins at block 502 with identifying a set of first facial landmarks in an image of a patient's face. The first facial landmarks can be one or more reference points corresponding to various anatomical features of the face, such as the eyes, eyebrows, nose, subnasion, mouth, lips, teeth, gingiva, checks, chin, jawline, etc. In some embodiments, the first facial landmarks are reference points that are responsible for perception of facial symmetry but are relatively independent of the patient's facial expression. For example, the first facial landmarks can include one or more landmarks on or near the eyes, nose, and/or subnasion, and/or can exclude one or more landmarks on or near the eyebrows and/or chin. The first facial landmarks can be manually identified by a user (e.g., a technician), automatically identified by a computing device (e.g., using computer vision and/or machine learning algorithms), or suitable combinations thereof (e.g., a computing device automatically identifies candidate landmarks which are subsequently reviewed and/or adjusted by a user), as described in greater detail elsewhere herein.

Figure 7A:
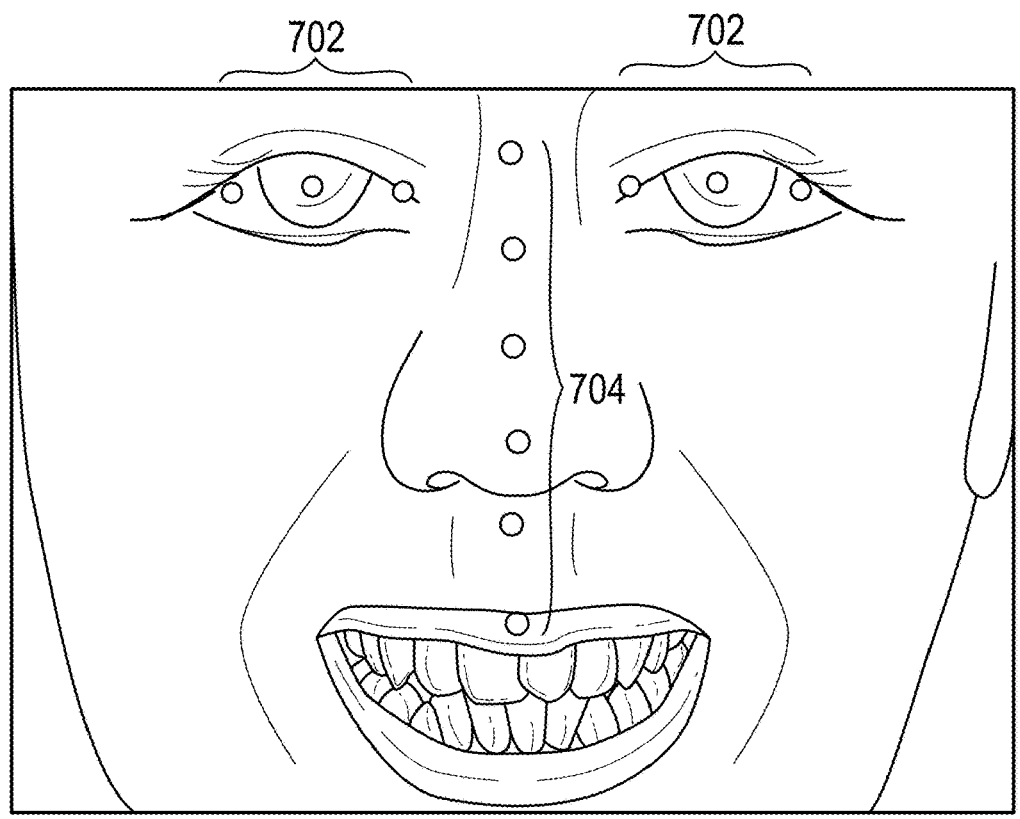
FIG. 7A illustrates a representative example of facial landmarks, in accordance with embodiments of the present technology.

FIG. 7A illustrates a representative example of facial landmarks, in accordance with embodiments of the present technology. In the illustrated embodiment, a total of 12 facial landmarks are shown: 6 facial landmarks associated with the patient's eyes ("eye landmarks 702"), and 6 facial landmarks associated with the patient's nose and subnasion ("nose/subnasion landmarks 704"). For example, the eye landmarks 702 can include, for each eye, one landmark 702 at or near the inner corner of the eye, one landmark 702 at or near the outer corner of the eye, and one landmark 702 at or near the center of the eye. The nose/subnasion landmarks 704 can lie on or near the patient's midline, and can extend from the bridge of the patient's nose to the patient's upper lip. In other embodiments, however, a different number and/or combination of facial landmarks can be used.

Figure 7B:
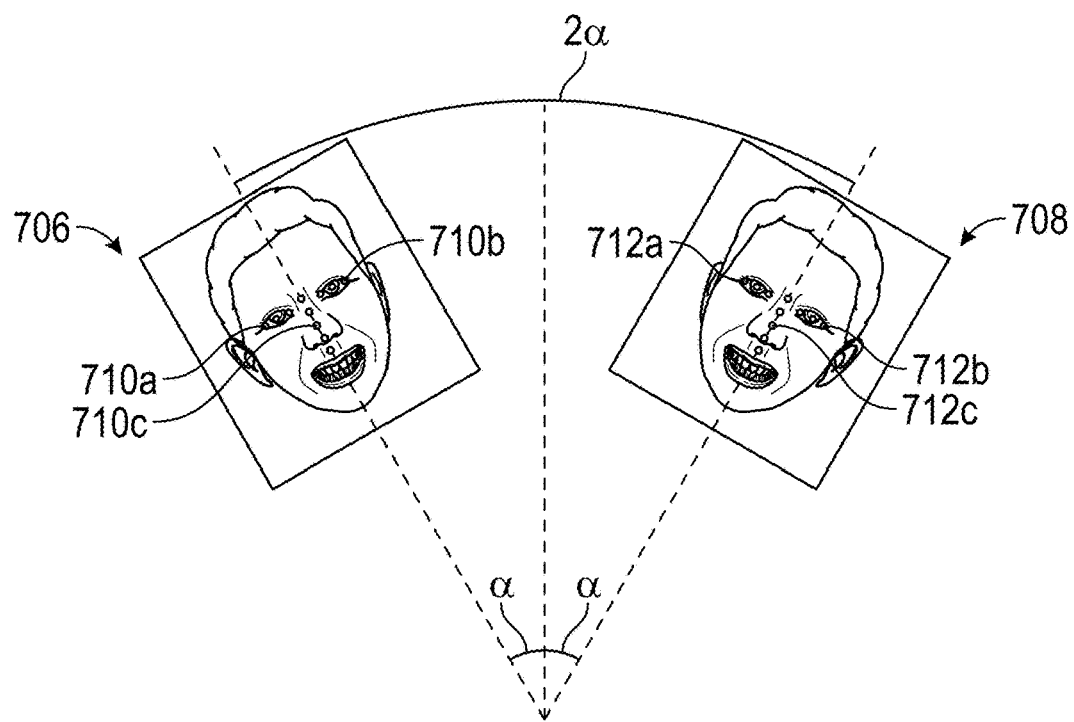
FIG. 7B illustrates an original image and a mirrored image, in accordance with embodiments of the present technology.
Figure 7C:
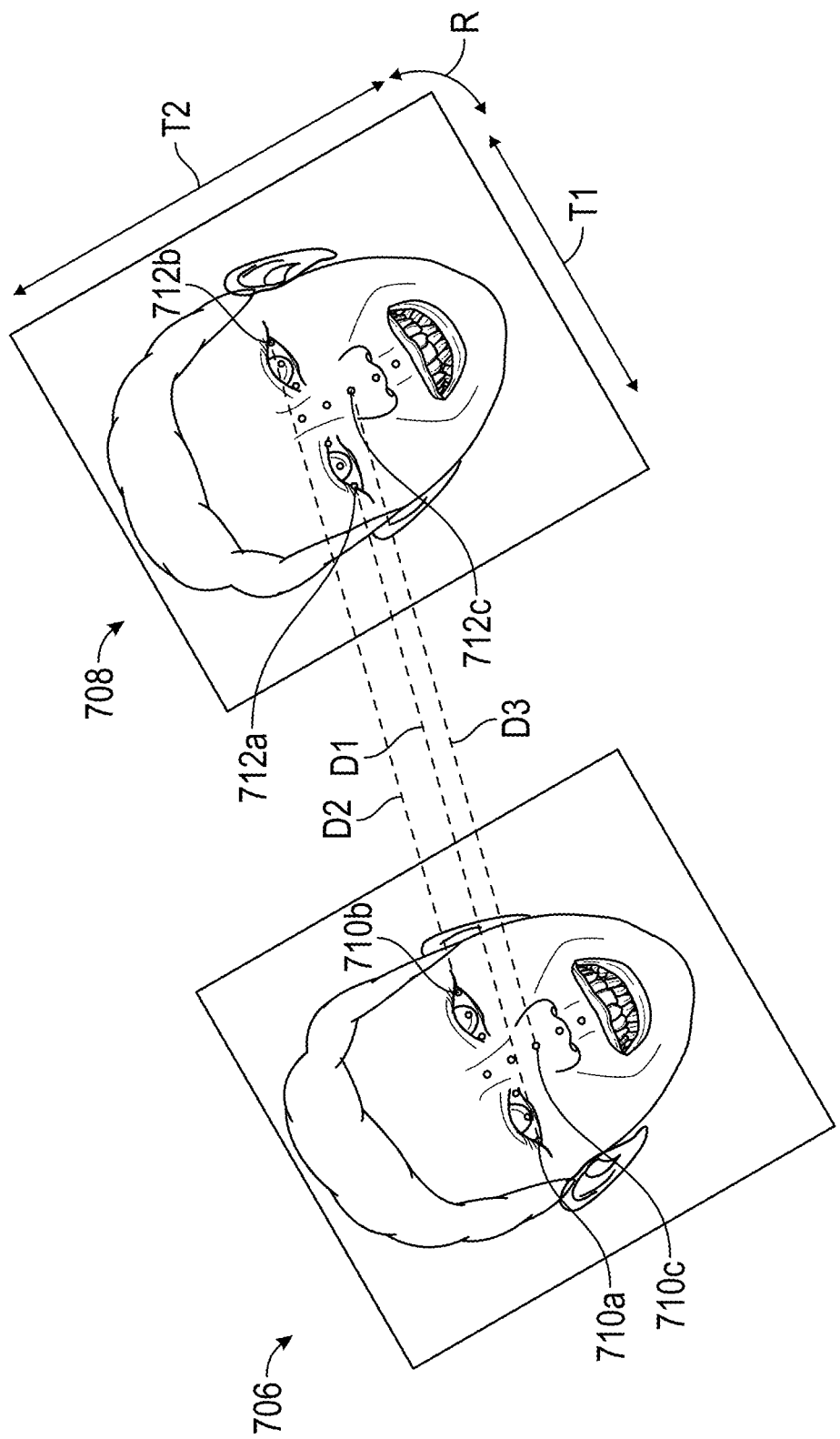
FIG. 7C illustrates matching facial landmarks in the original image and the mirrored image of FIG. 7B, in accordance with embodiments of the present technology.

Referring again to FIG. 5, at block 504, the method 500 can include generating a mirrored image with a set of second facial landmarks. For example, FIG. 7B illustrates an original image 706 and a mirrored image 708. The original image 706 can include a set of first facial landmarks, such as a plurality of first eye landmarks (e.g., landmarks 710a, 710b) and a plurality of first nose/subnasion landmarks (e.g., landmark 710c). The mirrored image 708 can include a plurality of second facial landmarks, such as a plurality of second eye landmarks (e.g., landmarks 712a, 712b) and a plurality of second nosc/subnasion landmarks (e.g., landmark 712c). The second facial landmarks of the mirrored image 708 can be manually identified by a user, automatically identified by a computing device, or suitable combinations thereof.

Referring again to FIG. 5, at block 506, the method 500 can include matching each first facial landmark to a corresponding second facial landmark. In some embodiments, as shown in FIG. 7B, each first eye landmark is matched to a second eye landmark that is on the same side of the face in the original image 706 and the mirrored image 708 (e.g., first eye land mark 710a is matched to second eye landmark 712a, first eye landmark 710b is matched to second eye landmark 712b), while each first nose/subnasion landmark is matched to its mirrored second nose/subnasion landmark (e.g., first nose/subnasion landmark 710c is matched to second nose/subnasion landmark 712c).

In some embodiments, the matching process of block 506 includes translating and/or rotating the mirrored image 708 to minimize the sum of squared distances between each first facial landmark in the original image 706 and its corresponding second facial landmark in the mirrored image 708. For example, referring to FIG. 7C, the mirrored image 708 can be translated along directions T1 and/or T2, and/or rotated along direction R. The distances between each of the first and second facial landmarks can be measured (e.g., distance D1 between first eye landmark 710a and second eye landmark 712a, distance D2 between first eye landmark 710b and second eye landmark 712b, distance D3 between first nosc/subnasion landmark 710c and second nose/subnasion landmark 712c). Subsequently, a numerical optimization method (e.g., Powell's method) can be used to determine the translation distance and/or rotation angle that minimizes the sum of the squared distances. In some embodiments, the facial landmarks are all weighted equally in the numerical optimization algorithm. In other embodiments, some of the facial landmarks can be weighted differently, e.g., distances determined from the eye landmarks can be weighted more heavily than distances determined from the nose/subnasion landmarks, or vice-versa.

Referring again to FIG. 5, at block 508, the method 500 can include determining a matching angle, based on the matching process of block 506. The matching angle can be the rotation angle of the mirrored image 708 that minimizes the sum of squared distances between the first and second facial landmarks, as described above. The matching angle can correspond to the angle $2a$ shown in FIG. 7B. The rotation angle that places the original image 706 in a vertical orientation can be half of the matching angle, e.g., the angle α shown in FIG. 7B. The original image 706 can then be rotated into a vertical orientation using the matching angle, and the rotated image can be used for subsequent processing.

Figures 8A, 8B:
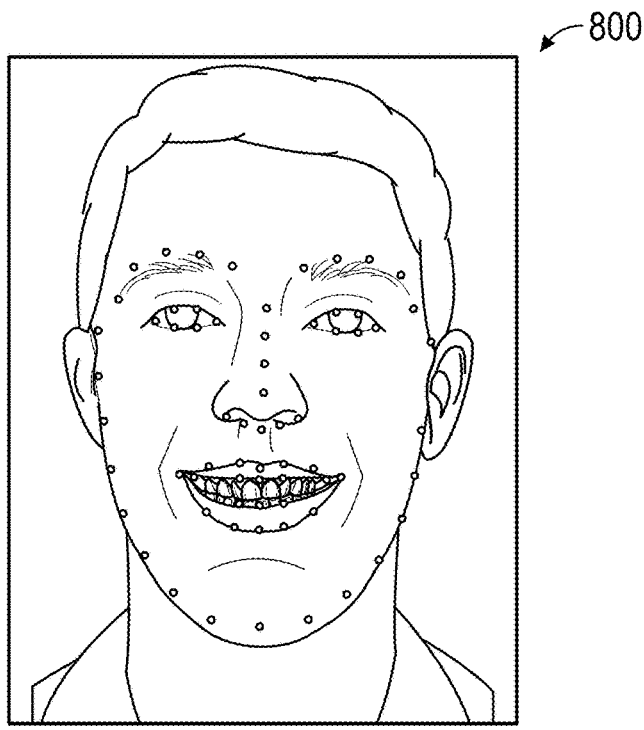
FIG. 8A illustrates a representative example of facial landmarks, in accordance with embodiments of the present technology.
FIG. 8B illustrates a representative example of a patient image in which the facial landmarks of FIG. 8A have been identified.

Referring again to FIG. 3, at block 308, the method 300 can continue with identifying one or more facial landmarks in the selected image(s). As previously described, the facial landmarks can be reference points corresponding to various anatomical features of the patient's face (e.g., eyes, eyebrows, nose, subnasion, mouth, lips, teeth, gingiva, checks, chin, jawline). For example, FIG. 8A shows 68 facial landmarks and their corresponding indices. The facial landmarks can include any of the following: facial outline landmarks (1-17) corresponding to the outline of the patient's face (e.g., chin and jawline), eyebrow landmarks (18-27) corresponding to the upper edge of the patient's eyebrows, nasal landmarks (28-36) corresponding to the features of the patient's nose (e.g., nasal centerline, subnasion), eye landmarks corresponding to the features of the patient's eyes (37-48) (e.g., corners, lids), and/or mouth landmarks corresponding to the features of the patient's mouth (49-68) (e.g., lips, mouth opening, teeth, gingiva).

FIG. 8B illustrates a representative example of a patient image 800 in which the 68 facial landmarks of FIG. 8A have been identified. The identification can be performed by a facial landmark detector algorithm utilizing suitable computer vision and/or machine learning techniques (e.g., CNNs and/or other deep learning techniques). The input to the algorithm can be a patient image, and the output of the algorithm can be the locations (e.g., x- and y-coordinates) of each facial landmark in the patient image. For example, the facial landmark detector algorithm can use an ensemble of regression trees that have been trained on a plurality of manually annotated patient images to estimate the locations of facial landmarks from a sparse subset of pixel intensities.

Referring again to FIG. 3, at block 310, the method 300 can include determining one or more facial lines (e.g., smile lines), based on the facial landmarks. As described elsewhere herein, the facial lines can correlate to the patient's unique anatomical features and can be used to define an aesthetic and/or functional treatment goal for the patient. For example, the facial lines can be smile lines defining one or more parameters of a target smile, such as the curvature of the smile, the locations and geometry of the teeth exposed by the smile, etc. A representative example of a process for determining facial lines is described below in connection with FIGS. 9A-12C.

Figure 9A:
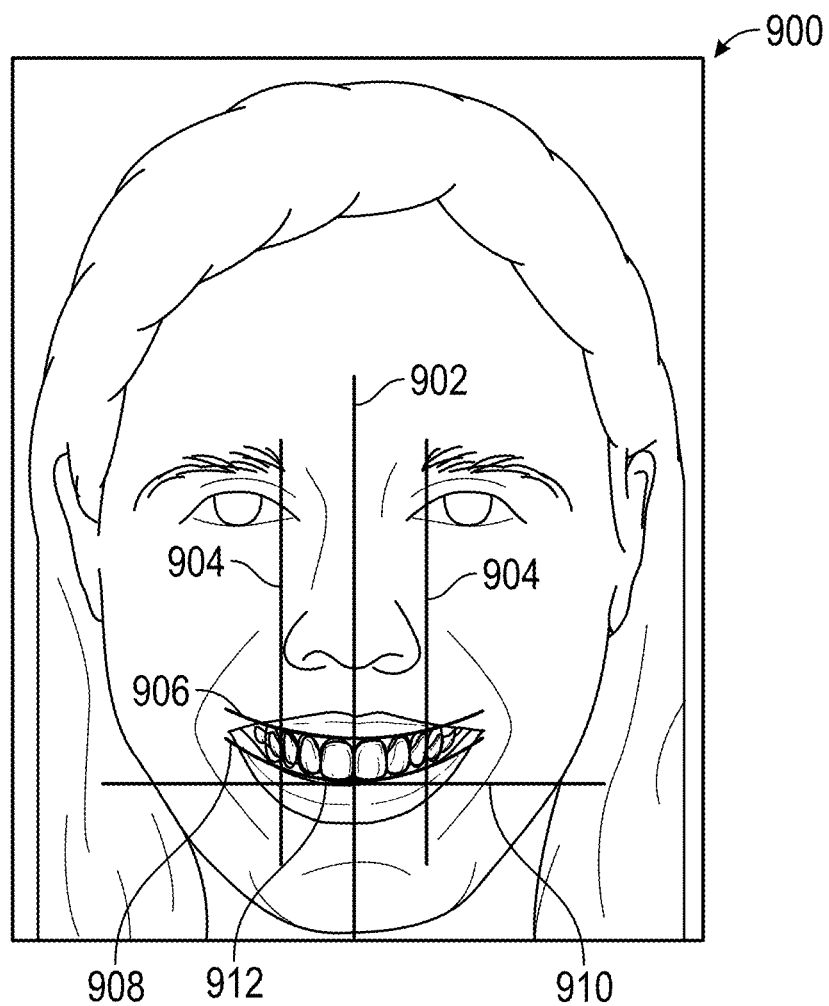
FIG. 9A is a representative example of a patient image including facial lines, in accordance with embodiments of the present technology.

FIG. 9A is a representative example of a patient image 900 including facial lines, in accordance with embodiments of the present technology. The facial lines can include a facial midline 902, a pair of intercanine width (ICW) lines 904, a gingival line 906, an incisal edge line 908, a horizontal line 910, and/or a plurality of tooth outlines 912. The facial midline 902 can be a vertical line corresponding to the center of the patient's face. The ICW lines 904 can be vertical lines passing through the right and left maxillary canines, respectively, such that the distance between the ICW line 904 corresponds to the ICW of the patient. The gingival line 906 can be a curved line corresponding to the exposed gingival margin and/or the lower edge of the patient's upper lip. The incisal edge line 908 can be a curved line corresponding to the exposed incisal edges of the teeth and/or the upper edge of the patient's lower lip. The horizontal line 910 can be orthogonal to the facial midline 902. The horizontal line 910 can be tangential to the lowest point of the gingival line 906. The tooth outlines 912 can correspond to the patient's front teeth (e.g., central incisors, lateral incisors, canines) and can be based on one or more tooth proportions, such as the ratio of the height of central incisor to the width of the central incisors ("centrals height to width ratio"), the ratio of the width of the lateral incisors to the width of the central incisors ("laterals to centrals to width ratio"), and/or the ratio of the width of the canine to the width of the lateral incisors ("canines to laterals width ratio").

Figure 9B:
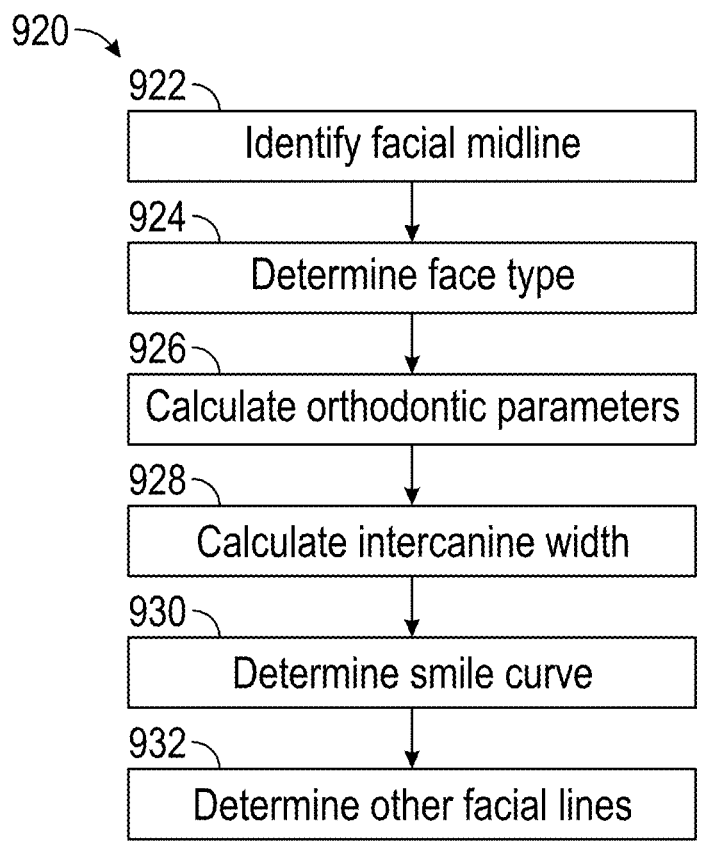
FIG. 9B is a flow diagram illustrating a method for determining facial lines, in accordance with embodiments of the present technology.

FIG. 9B is a flow diagram illustrating a method 920 for determining facial lines, in accordance with embodiments of the present technology. The method 920 begins at block 922 with determining a facial midline. The facial midline can be determined from the patient image in various ways, such as calculated based on one or more facial landmarks (e.g., any of the facial landmarks illustrated in FIG. 8A). For example, the locations of facial landmarks that are expected to be at or near the center of the patient's face (e.g., nose/subnasion landmarks) can be directly used as points on the facial midline. Alternatively or in combination, the locations of facial landmarks that are expected to be vertically symmetric about the facial midline can be used to calculate midpoints, and the midpoints can be used as points on the facial midline. In some embodiments, the facial midline is calculated by determining a plurality of midline sections from respective sets of facial landmarks, then averaging the midline sections. For example, an upper midline section can be calculated based on landmarks at or near the eyes, a lower midline section can be calculated based on landmarks at or near the subnasion and/or lips, and the upper and lower midlines sections can be averaged to determine the facial midline.

At block 924, the method 920 can include determining a face type of the patient. For example, FIG. 10A illustrates facial landmarks that can be used to determine a face type, in accordance with embodiments of the present technology. The facial landmarks can include the facial midline 1002, the glabella 1004, the chin 1006, the prominences of the cheekbones 1008, the temples superior to the ears 1010, and/or the mandibular angles 1012. In some embodiments, the facial landmarks are used to generate one or more measurements, which in turn are used to classify the patient's face into one of a plurality of different face types (e.g., short, average, tall). For example, the measurements can include the distance from the glabella 1004 to the chin 1006, the distance between the cheekbones 1008, the distance between the temples 1010, and/or the distance between the mandibular angles 1012. In some embodiments, the face type is defined by the ratio $\beta$=height/width, where the height corresponds to the distance from the glabella 1004 to the chin 1006, and the width corresponds to the distance between the mandibular angles 1012. Higher values of $\beta$ can correlate to a taller face type, while lower values of $\beta$ can correlate to a shorter face type.

FIGS. 10B-10D illustrate three representative examples of face types, in accordance with embodiments of the present technology. In a short-type face (FIG. 10B), the distance between the glabella 1004 and the chin 1006 can be similar to or equal to the distance between the cheekbones 1008 (e.g., within 10%), and/or the distance between the cheekbones 1008 can be similar or equal to the distance between the mandibular angles 1012 (e.g., within 10%).

In an average-type face (FIG. 10C), the distance between the glabella 1004 and the chin 1006 can be much greater than the distance between the cheekbones 1008 (e.g., 15% to 20% greater), the distance between the cheekbones 1008 can be similar to or equal to the distance between the mandibular angles 1012 (e.g., within 10%), and/or the distance between the temples 1010 can be greater than the distance between the mandibular angles 1012 (e.g., 10% to 15% greater).

In a tall-type face (FIG. 10D), the distance between the glabella 1004 and the chin 1006 can be much greater than the distance between the cheekbones 1008 (e.g., at least 20% greater), the distance between the glabella 1004 and the chin 1006 can be much greater than the distance between the mandibular angles 1012 (e.g., at least 20% greater), and/or the distance between the glabella 1004 and the chin 1006 can be much greater than the distance between the temples 1010 (e.g., at least 20% greater). The distance between the temples 1010 can be similar or equal to the distance between the mandibular angles 1012 (e.g., within 10%), and/or the distance between the cheekbones 1008 can be similar or equal to the distance between the mandibular angles 1012 (e.g., within 10%).

Referring again to FIG. 9B, at block 926, the method 920 can include calculating one or more orthodontic parameters, based on the face type. The orthodontic parameters can define various dimensions and/or proportions of the patient's teeth that can be used to define an aesthetically pleasing target smile. For example, the orthodontic parameters can include a central incisor width (CIW), Recurring Esthetic Dental (RED) proportion, and/or ICW multiplier.

Figure 11:
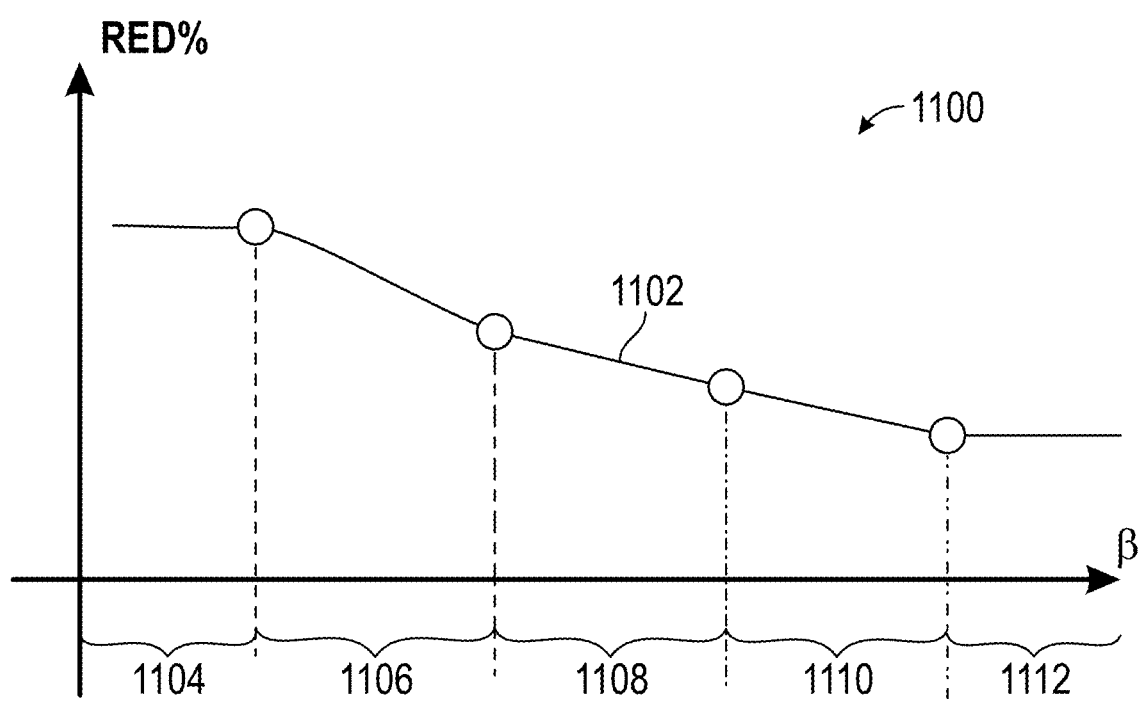
FIG. 11 is a graph illustrating the relationship between face type and the Recurring Esthetic Dental proportion, in accordance with embodiments of the present technology.

The orthodontic parameters can be calculated in various ways. In some embodiments, for instance, some or all of the orthodontic parameters are calculated from the ratio β using a continuous function. As an example, FIG. 11 is a graph 1100 illustrating the relationship between β and the RED proportion (RED %). The corresponding RED % for a particular value of β can be determined by inputting β into a continuous function, represented by a curve 1102 in FIG. 11. As previously discussed, the patient's face type can be categorized based on the value of β, e.g., a value within range 1104 corresponds to a "very short" face type, a value within range 1106 corresponds to a "short" face type, a value within range 1108 corresponds to an "average" face type, a value within range 1110 corresponds to a "tall" face type, and a value within range 1112 corresponds to a "very tall" face type. The CIW and/or ICW multiplier can also be determined from β via respective continuous functions.

As another example, some or all of the orthodontic parameters can be determined based on the face type using a table of discrete values. For example, the CIW can be calculated based on the face type and an intercanthal distance measured between the inner corners of the eyes. The ICW multiplier can be selected from one of a plurality of discrete values based on the face type (e.g., the ICW multiplier is a first value for a very tall face type, the ICW multiplier is a second value for a tall face type, and so on). The RED proportion can also be selected from one of a plurality of discrete values based on the face type (e.g., the RED proportion is a first value for a very tall face type, the RED proportion is a second value for a tall face type, and so on).

Referring again to FIG. 9B, at block 928, the method 920 can continue with calculating the ICW. In some embodiments, the ICW is calculated using two different approaches: an "inside-out" approach and an "outside-in approach." For the inside-out approach, the average width of the eyes is calculated, and each ICW line is positioned at a location that is a predetermined percentage of the average width (e.g., 10%) offset from the inner canthus of the eye. For the outside-in approach, the ICW is calculated from by multiplying the CIW with the ICW multiplier. The results from the inside-out and outside-in approach can then be averaged and used as the final ICW value. This technique can make the ICW calculation more robust and applicable for a wide variety of faces.

At block 930, the method 920 can include determining at least one smile curve. The smile curve can be determined from one or more reference points on the patient's teeth ("tooth reference points"). The tooth reference points can include any locations suitable for defining the curvature of the patient's target smile, such as the cusps or tips of one or more teeth (e.g., central incisors, lateral incisors, canines), midpoints between two teeth (e.g., midpoint between the upper central incisors, midpoint between an upper central incisor and a lower central incisor), etc. The tooth reference points can be automatically or semi-automatically determined from an image of the patient's teeth (e.g., the same image used in the other processes of the method 920) and/or other data of the patient's teeth (e.g., scan data).

Figure 12A:
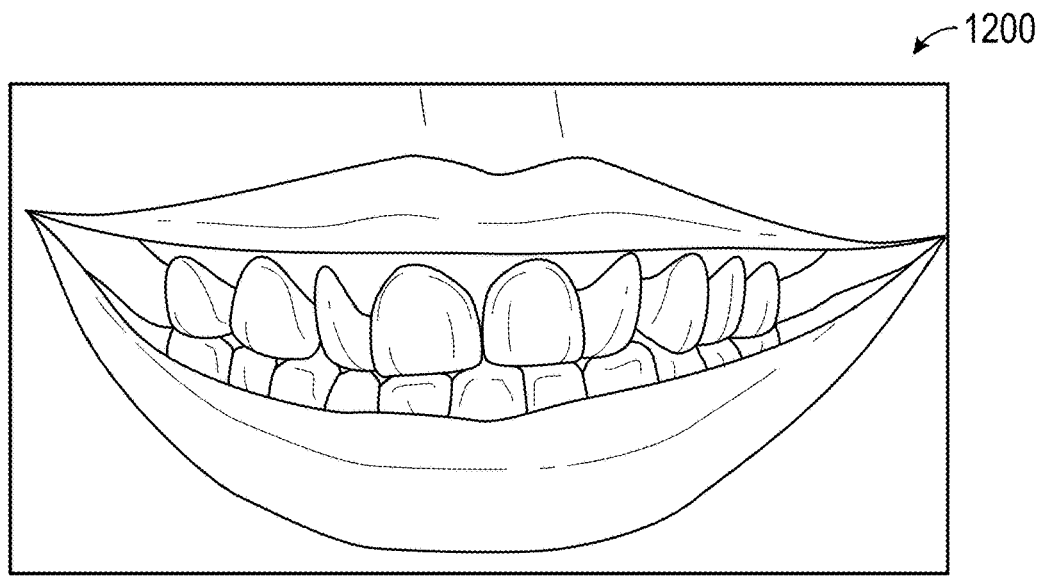
FIGS. 12A-12C illustrate a process for determining tooth reference points and a smile curve, in accordance with embodiments of the present technology.
Figure 12B:
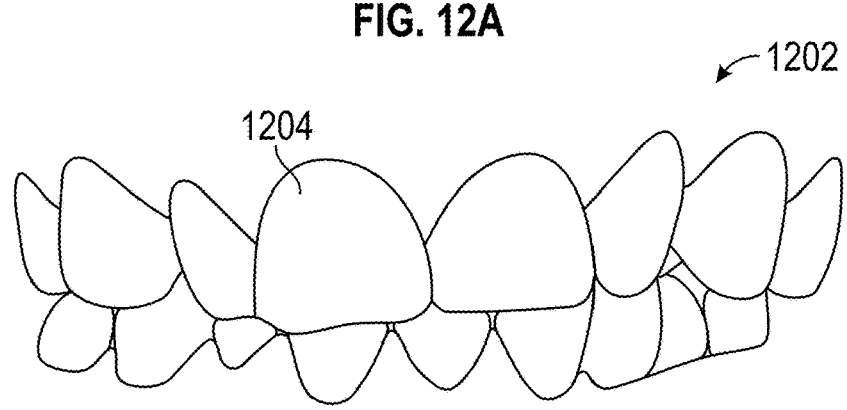
Figure 12C:
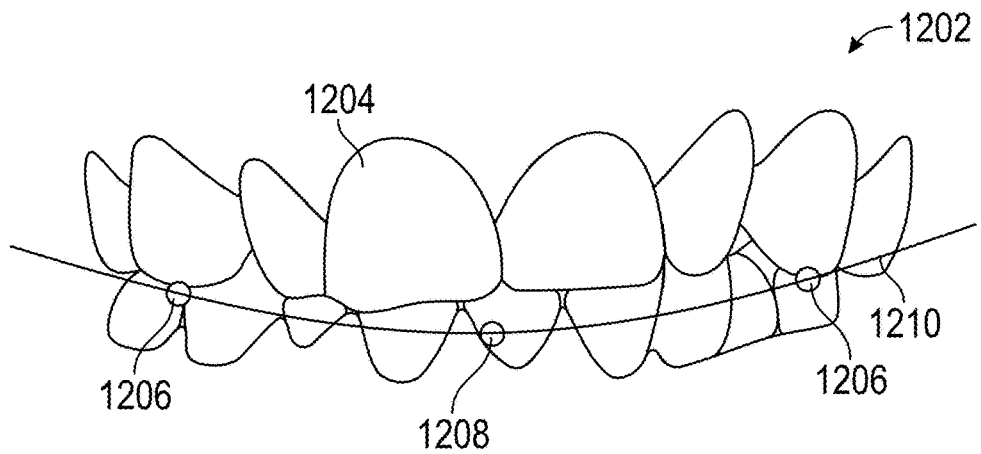

In some embodiments, the tooth reference points are determined using a teeth segmentation algorithm. The teeth segmentation algorithm can utilize any suitable computer vision and/or machine learning technique, such as a deep neural network architecture for object recognition based on recurrent neural networks (RNNs). For example, FIG. 12A illustrates an image 1200 of the teeth that can be used as input into the teeth segmentation algorithm, and FIG. 12B illustrates a segmentation mask 1202 that can be the output of the teeth segmentation algorithm. The segmentation mask 1202 can include a tooth mask 1204 for each of the patient's frontal teeth (e.g., 8 upper frontal teeth and 8 lower frontal teeth). Each tooth mask 1204 can includes a 2D shape representing the location and geometry of the corresponding tooth in the image 1200. The teeth segmentation algorithm can also output a confidence value (e.g., a number from 0 to 1) for each tooth mask 1204. The tooth mask 1204 can be considered to be sufficiently high quality for use if the confidence value is above a predetermined threshold (e.g., greater than or equal to 0.8). As shown in FIG. 12C, the segmentation mask 1202 can then be used to determine a plurality of tooth reference points, such as canine tip points 1206 and a leveling point 1208. A smile curve 1210 can then be determined by drawing a parabola through the tooth reference points. Alternatively or in combination, the curvature of the smile curve 1210 can be determined based on the curvature of the lower lips (e.g., facial landmarks 61, 65, 66, 67, and 68 in FIG. 7A).

Optionally, the segmentation mask 1202 can also be used to determine a pixel to mm conversion coefficient. In such embodiments, a tooth dimension (e.g., CIW) can be measured in pixels from the segmentation mask 1202. The conversion coefficient can then be calculated based on statistical data of the tooth dimension (e.g., the average CIW is approximately 9 mm). The conversion coefficient can be used to set distance-based limitations in subsequent treatment planning processes.

Referring again to FIG. 9B, at block 932, the method 920 can include determining at least one other facial line. For example, one or more facial lines can be determined from the smile curve of block 930. In some embodiments, the incisal edge line is the same as the smile curve. The gingival line can be determined by moving the center point of the smile curve vertically upwards by the central incisor height, and the curvature of the gingival line can be a predetermined value determined from previous treatment cases. The tooth outlines can be determined by calculating additional tooth dimensions and/or proportions from the CIW and RED proportions from block 926, such as the lateral incisor width, canine width, centrals height to width ratio, laterals to centrals width ratio, and/or canines to laterals width ratio. Additional examples of techniques for calculating facial lines and tooth proportions are described in U.S. Pat. No. 10,758,322, filed Mar. 20, 2018, the disclosure of which is incorporated by reference herein in its entirety.

Referring again to FIG. 3, at block 312, the method 300 can include outputting a visualization of the facial lines. The visualization can depict the facial lines overlaid onto an image of the patient's face (e.g., the selected image used to determine the facial lines). Optionally, the visualization can also include a 3D model of the teeth and/or gingiva overlaid onto the image of the patient's face, thus producing a composite image (also referred to herein as an "in-face visualization"). Representative examples of techniques for generating such composite images are described in U.S. Pat. No. 10,758,322, filed Mar. 20, 2018, the disclosure of which is incorporated by reference herein in its entirety. The 3D model can depict the patient's teeth in an initial tooth arrangement before the start of a treatment procedure, an intermediate tooth arrangement during a stage of the treatment procedure, and/or a target tooth arrangement that is the intended goal of the treatment procedure.

The visualization can be displayed to a user (e.g., clinician, technician, patient) so the user can assess how a particular tooth arrangement compares to the target smile defined by the facial lines. For example, the user can use the facial lines as a reference when designing and/or modifying a target tooth arrangement for the patient. Optionally, the user can provide feedback modifying one or more of the facial lines, which in turn can be used to update the treatment plan, as described in greater detail below.

The method 300 can be varied in many different ways. For example, some of the processes shown in FIG. 3 can be omitted (e.g., the processes of blocks 304 and/or 306) and/or the method 300 can include additional processes not shown in FIG. 3. Moreover, the method 300 can be combined with any of the other methods described herein. For instance, some or all of the processes of the method 300 can be performed as part of the processes of blocks 204 and/or 206 of the method 200 of FIG. 2.

Figure 13:
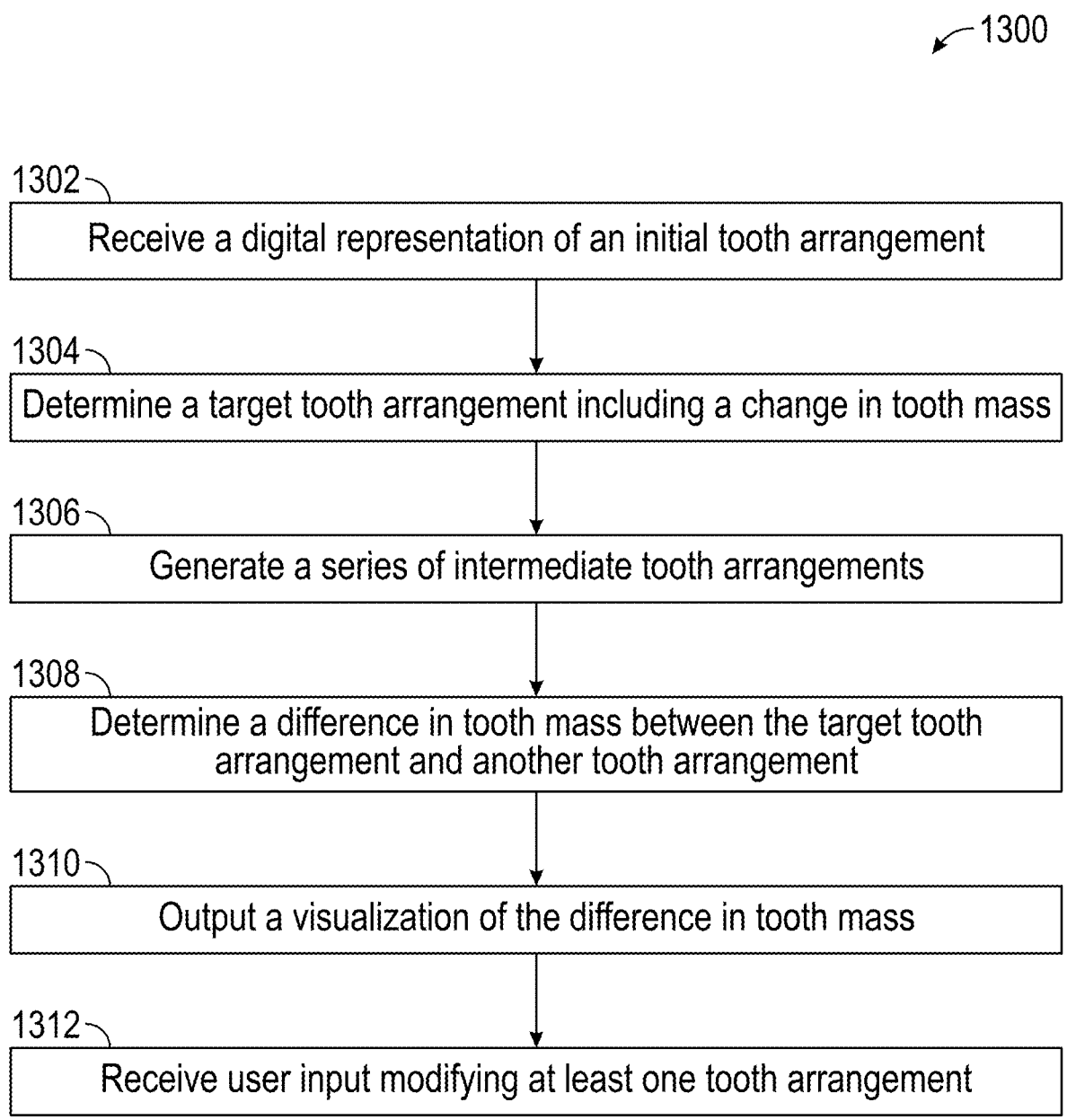
FIG. 13 is a flow diagram illustrating a method for planning an ortho-restorative treatment, in accordance with embodiments of the present technology.

FIG. 13 is a flow diagram illustrating a method 1300 for planning an ortho-restorative treatment, in accordance with embodiments of the present technology. As previously described, an ortho-restorative treatment can include repositioning one or more teeth to correct malocclusions, while also altering the mass of one or more teeth to restore damaged or missing teeth and/or to correct the shape of malformed teeth. In some instances, it may be challenging for a clinician to determine an appropriate combination of tooth movements and tooth mass modification that would achieve the desired treatment goal while reducing invasiveness and treatment duration. The method 1300 can assist the clinician with ortho-restorative treatment planning by determining how orthodontic tooth movements may affect the tooth mass modification needed, and vice-versa. For example, the method 1300 can be used to generate a visualization (e.g., a heatmap overlay) that allows the clinician to view the locations and/or amounts of tooth mass modification at each treatment stage. Accordingly, the present technology can improve the efficacy of ortho-restorative treatment planning by optimizing tooth movements, improving the reliability of restorative placement, and reducing the amount of tooth mass modification used.

The method 1300 can be performed using any suitable system or device. In some embodiment, some or all of the processes of the method 1300 are implemented as computer-readable instructions (e.g., program code) that are configured to be executed by one or more processors of a computing device. For example, some or all of the processes of the method 1300 can be performed by one or more components of the system 100 of FIG. 1, such as the data input component 102, the treatment planning component 104, and/or the treatment visualization component 106.

The method 1300 begins at block 1302 with receiving a digital representation of an initial tooth arrangement. The process of block 1302 can be identical or generally similar to the process of block 202 of the method 200 of FIG. 2. For example, the digital representation can be a 3D model of a patient's teeth before the start of the ortho-restorative treatment procedure.

At block 1304, the method 1300 can include determining a target tooth arrangement including a change in tooth mass. The process of block 1304 can be identical or generally similar to the process of block 204 of the method 200 of FIG. 2. For example, the target tooth arrangement can be determined by identifying one or more indications present in the initial tooth arrangement (e.g., maloccluded, malformed, damaged, and/or missing teeth), then determining changes to the position and/or shape of one or more teeth that would correct some or all of the indications. The target tooth arrangement can include changing the mass of at least one tooth. For example, the target tooth arrangement can include at least one tooth having a restorative object that increases the overall mass of the tooth, such as a crown, veneer, composite, etc. As another example, the target tooth arrangement can include at least one restorative object (e.g., a prosthesis) that replaces a missing tooth. In a further example, the target tooth arrangement can include at least one tooth that has undergone a reduction in mass, e.g., to achieve a desired shape, prepare the tooth for receiving a restorative object, making space to accommodate a restorative object on another tooth, making space to accommodate orthodontic movements, etc.

In some embodiments, the target tooth arrangement is determined based at least in part on the patient's facial anatomy. For example, the target tooth arrangement can be designed using one or more facial lines (e.g., smile lines) as a reference. As previously described with respect to the method 300 of FIG. 3, the facial lines can be automatically generated from one or more images of the patient's face, and can define the features of a target smile that is likely to be considered aesthetically pleasing according to the patient's facial features. In such embodiments, the process of block 1304 can include adjusting the position and/or shape of one or more teeth to conform to the facial lines. For example, referring again to FIG. 9A, the shapes and/or positions of one or more teeth can be adjusted so that, in the target tooth arrangement: (1) the teeth are generally symmetric about the facial midline 902; (2) the distance between the canines is substantially equal to the ICW defined by the ICW line 904 (e.g., within 10%); (3) the upper and lower portions of the front teeth (e.g., incisors, canines) are generally aligned with the gingival line 906 and incisal edge line 908, respectively; (4) the lower portions of the central incisors are generally aligned with the horizontal line 910; and/or (5) the sizes and shapes of the teeth generally conform to the sizes and shapes of the tooth outlines 912.

The target tooth arrangement can be determined manually by a user (e.g., a clinician, technician), automatically by a computing device (e.g., using a software algorithm implemented by the treatment planning component 104 of FIG. 1), or suitable combinations thereof. In embodiments where the target tooth arrangement is determined by a user, the user can refer to a visualization including one or more facial lines (e.g., smile lines) for guidance, as previously described in connection with block 312 of FIG. 3.

At block 1306, the method 1300 can include generating a series of intermediate tooth arrangements. The series of intermediate tooth arrangements can be configured to adjust the patient's teeth from the initial tooth arrangement toward the target tooth arrangement. Each intermediate tooth arrangement can correspond to an orthodontic treatment stage to be achieved with a respective orthodontic appliance, as described elsewhere herein.

At block 1310, the method 1300 can include determining a difference in tooth mass between the target arrangement and at least one other tooth arrangement, also referred to herein as "tooth mass analysis." The other tooth arrangement can be the initial tooth arrangement or an intermediate tooth arrangement. Optionally, the process of block 1310 includes performing tooth mass analysis on the initial tooth arrangement and all of the intermediate tooth arrangements.

The tooth mass analysis can be performed in various ways. For example, the tooth mass analysis can involve identifying, for each tooth in the other tooth arrangement ("original tooth"), a corresponding tooth in the target tooth arrangement ("target tooth"). The target tooth can be the same tooth as the original tooth, except that the target tooth has been adjusted via orthodontic repositioning and/or tooth mass modification. The position and/or shape of the original tooth can then be compared to the position and/or shape of the target tooth to identify (1) locations where the original tooth has added mass compared to the target tooth, (2) locations where the original tooth has reduced mass compared to the target tooth, and/or (3) locations where the mass of the original tooth is the same as the mass of the target tooth. These locations can be marked using visual indicators (e.g., different colors, textures, opacities, borders, labels) to provide a visualization of the tooth mass analysis results, as discussed further below.

Figure 14A:
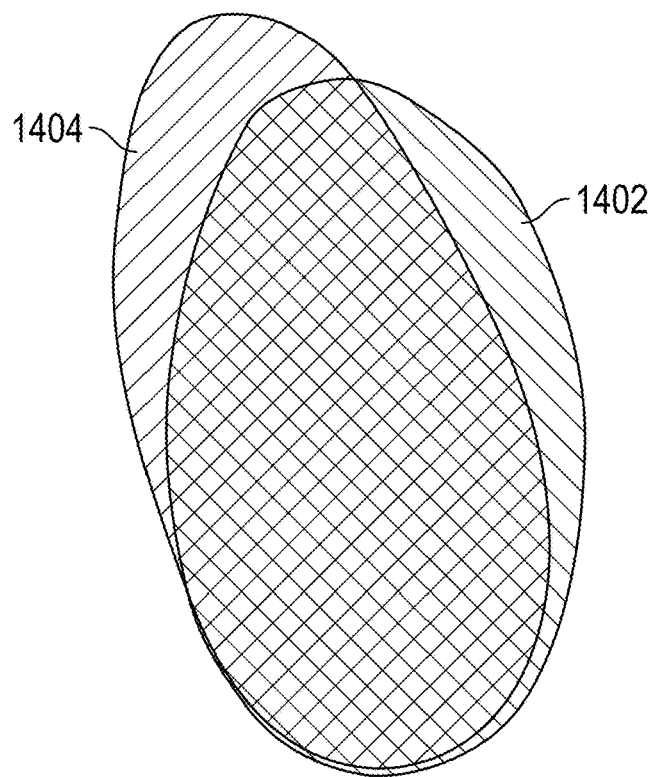
FIGS. 14A-14E are partially schematic illustrations of a process for tooth mass analysis, in accordance with embodiments of the present technology.

FIGS. 14A-14E are partially schematic illustrations of a process for tooth mass analysis, in accordance with embodiments of the present technology. Referring first to FIG. 14A, an original tooth 1402 (e.g., a tooth in the initial tooth arrangement or an intermediate tooth arrangement) can have a different geometry than a target tooth 1404 (e.g., the corresponding tooth in the target tooth arrangement). The different geometry can result from tooth repositioning, tooth mass addition (e.g., application of a restorative object), tooth mass reduction, or a combination thereof.

Figure 14B:
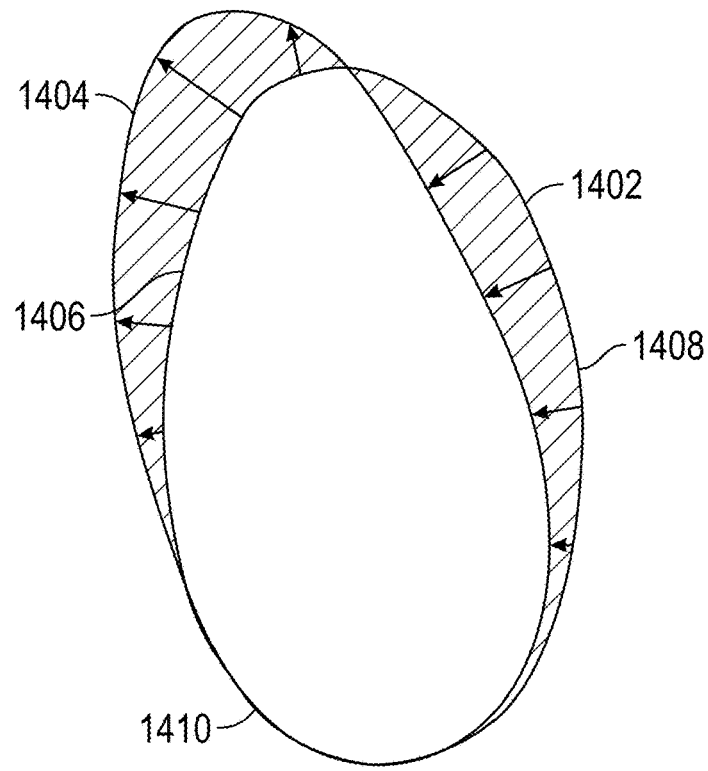

Referring next to FIG. 14B, to determine the change in tooth mass, the surface of the original tooth 1402 can be compared to the surface of the target tooth 1404 to identify differences indicative of tooth mass addition and/or reduction. In the illustrated embodiment, for example, the surface of the original tooth 1402 differs from the surface of the target tooth 1404 at a first region 1406 and a second region 1408. At the first region 1406, the surface of the original tooth 1402 is recessed relative to the surface of the target tooth 1404, thus indicating that tooth mass addition would occur at the first region 1406. At the second region 1408, the surface of the original tooth 1402 is protruded relative to the surface of the target tooth 1404, thus indicating tooth mass reduction would occur at the second region 1408. At a third region 1410, the surface of the original tooth 1402 can be aligned with the surface of the target tooth 1404, thus indicating no change in tooth mass would occur at the third region 1410.

Figure 14C:
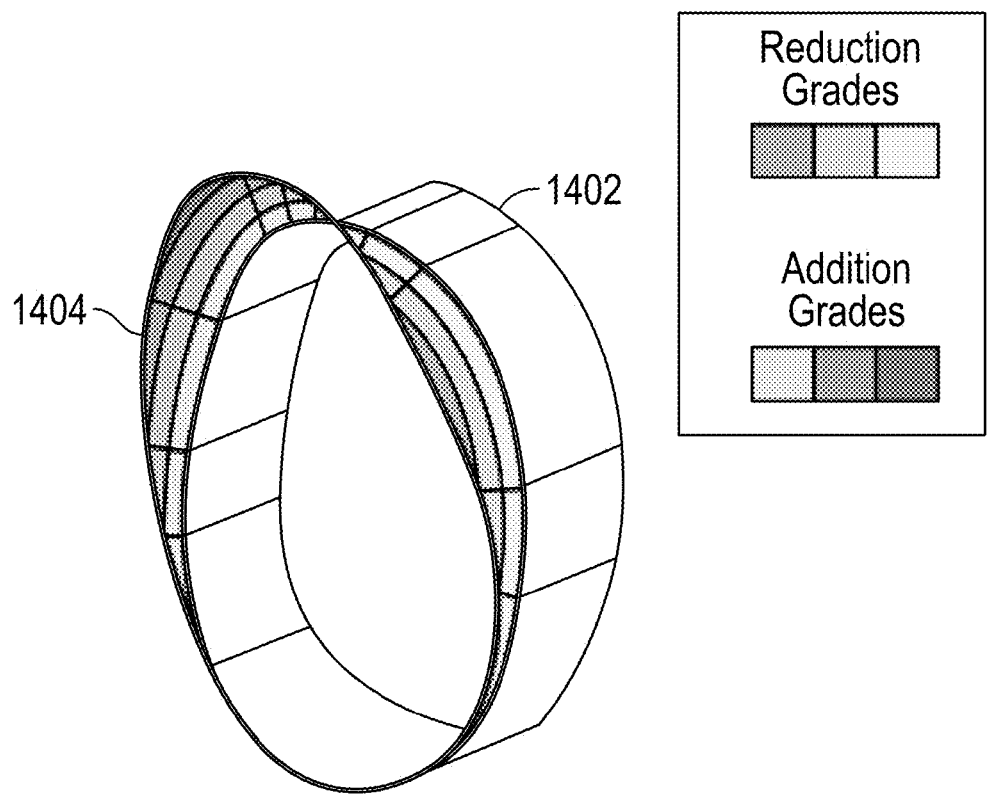

Referring next to FIG. 14C, the distance between the surface of the original tooth 1402 and the target tooth 1404 can be measured at multiple locations. For example, positive distance values ("addition grades") can represent locations where tooth mass addition will occur, negative distance values ("reduction grades") can represent locations where tooth mass reduction will occur, and zero can represent locations where no changes in tooth mass will occur. Optionally, a heatmap scale can be defined, with different colors of the heatmap corresponding to different distance values. In some embodiments, the distance values can be categorized into discrete grades, e.g., a first color is used for tooth mass addition of up to 0.5 mm, a second color is used for tooth mass addition greater than 0.5 mm and up to 1 mm, a third color is used for tooth mass addition greater than 1 mm and up to 2 mm, etc.

Figure 14D:
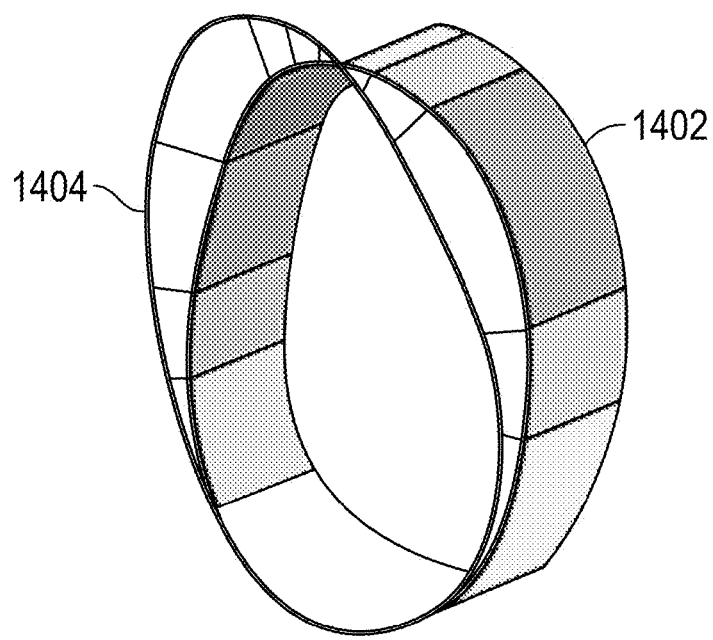
Figure 14E:
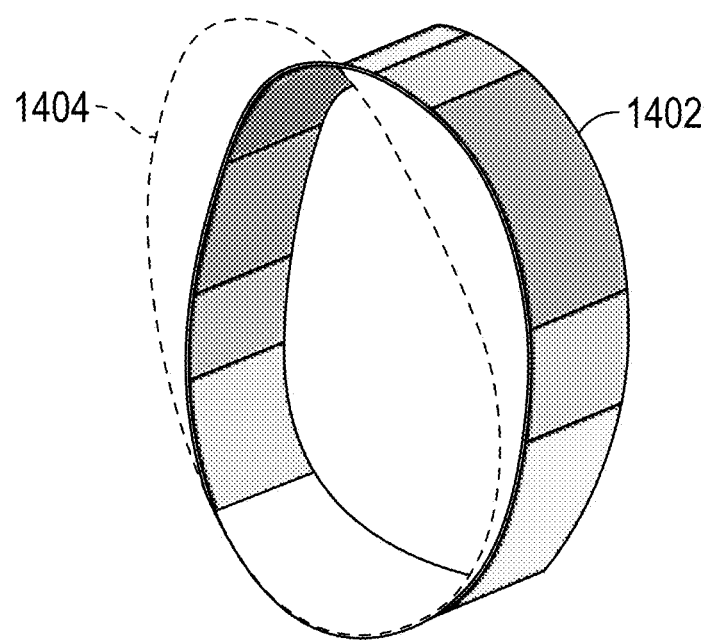

As shown in FIG. 14D, each location on the surface of the original tooth 1402 can be marked with a corresponding color according to the measured distance between the surface of the original tooth 1402 and the surface of the target tooth 1404 at that location. Accordingly, as shown in FIG. 14E, the tooth mass analysis can be displayed to a user as a colored heatmap overlaid on the original tooth 1402 showing the amounts and locations of tooth mass modification that would occur to achieve the geometry of the target tooth 1404.

Referring again to FIG. 13, at block 1310, the method 1300 can include outputting a visualization of the difference in tooth mass. The visualization can provide a graphical representation of the results of the tooth mass analysis to assist a user in evaluating the difference in tooth mass between the target tooth arrangement and the other (e.g., initial or intermediate) tooth arrangement. For example, the visualization can include a heatmap overlaid onto the other tooth arrangement that depicts the amounts and locations of tooth mass reduction and/or addition to achieve the target tooth arrangement, as discussed above. Alternatively or in combination, the visualization can present the tooth mass analysis results using any other suitable format, such as tables, graphs, charts, animations, etc.

Figure 15A:
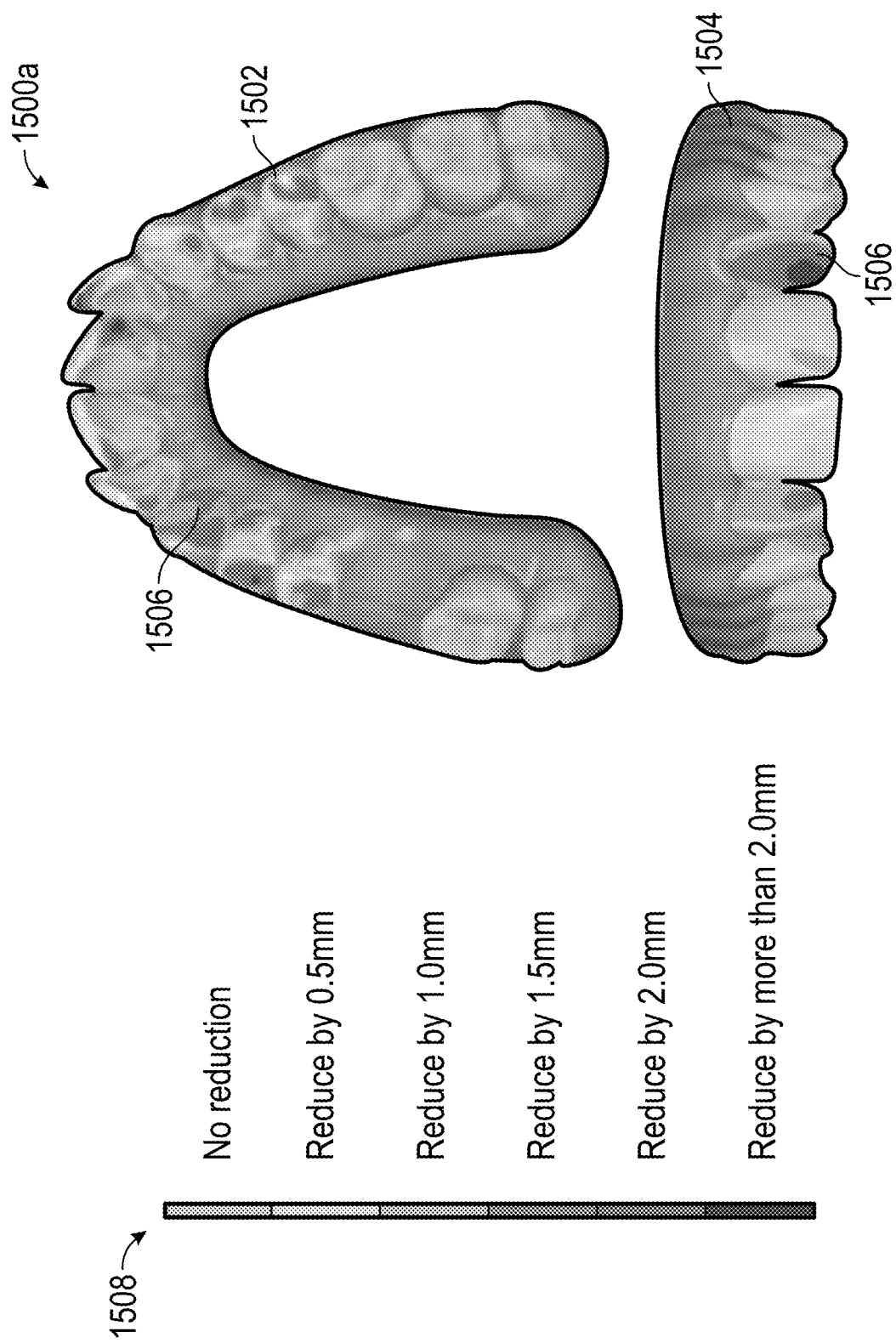
FIGS. 15A-15D illustrate representative examples of visualizations of tooth mass analysis results, in accordance with embodiments of the present technology.

FIGS. 15A-15D illustrate representative examples of visualizations of tooth mass analysis results, in accordance with embodiments of the present technology. Referring first to FIG. 15A, this embodiment illustrates a visualization 1500*a* in a reduction only mode. The visualization 1500*a* can include one or more digital representations of an arrangement of the patient's teeth, such as a first 3D model 1502 of the patient's arch from an occlusal view, and a second 3D model 1504 of the patient's arch from a frontal view. Optionally, the user can manipulate the digital representation(s), such as by translating, rotating, zooming in, zooming out, etc. The visualization 1500*a* includes a heatmap 1506 overlaid onto the digital representation(s) to show the amounts and locations of tooth mass reduction on the displayed tooth arrangement relative to the target tooth arrangement. The visualization 1500*a* can also include a legend 1508 indicating how the different colors of the heatmap 1506 correlate to different grades of tooth mass reduction.

Figure 15B:
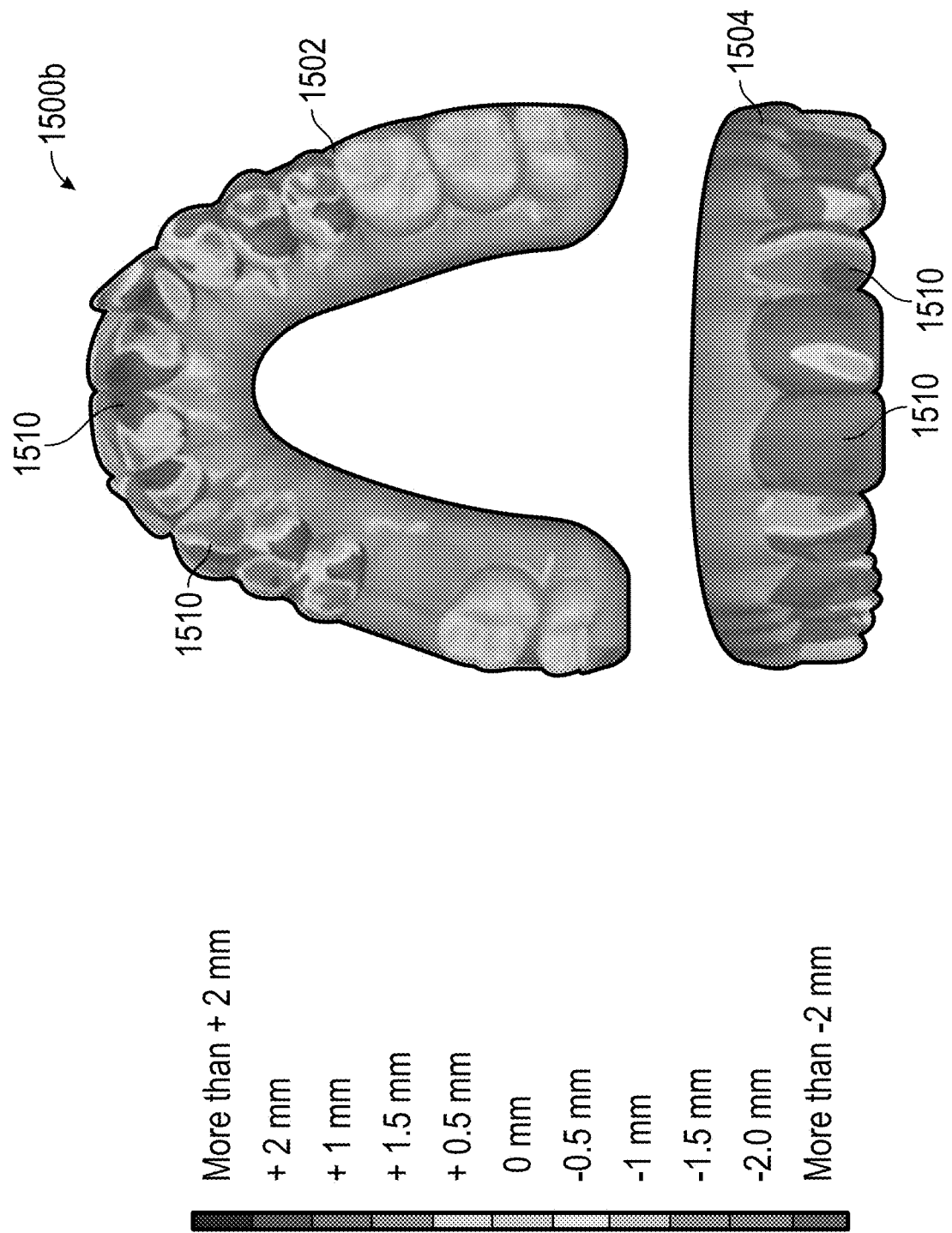

FIG. 15B illustrates a visualization 1500*b* in an addition and reduction mode. The visualization 1500*b* can be generally similar to the visualization 1500*a* of FIG. 15A, except that the visualization 1500*b* shows both tooth mass addition and tooth mass reduction. For example, the visualization 1500*b* can include one or more digital representations of an arrangement of the patient's teeth, such as the first 3D model 1502 and the second 3D model 1504 described above. The visualization 1500*b* can include a heatmap 1510 overlaid onto the digital representation(s) to show the amounts and locations of tooth mass reduction and tooth mass addition on the displayed tooth arrangement relative to the target tooth arrangement. The visualization 1500*b* can also include a legend 1512 indicating how the different colors of the heatmap 1510 correlate to different grades of tooth mass reduction and addition.

Figure 15C:
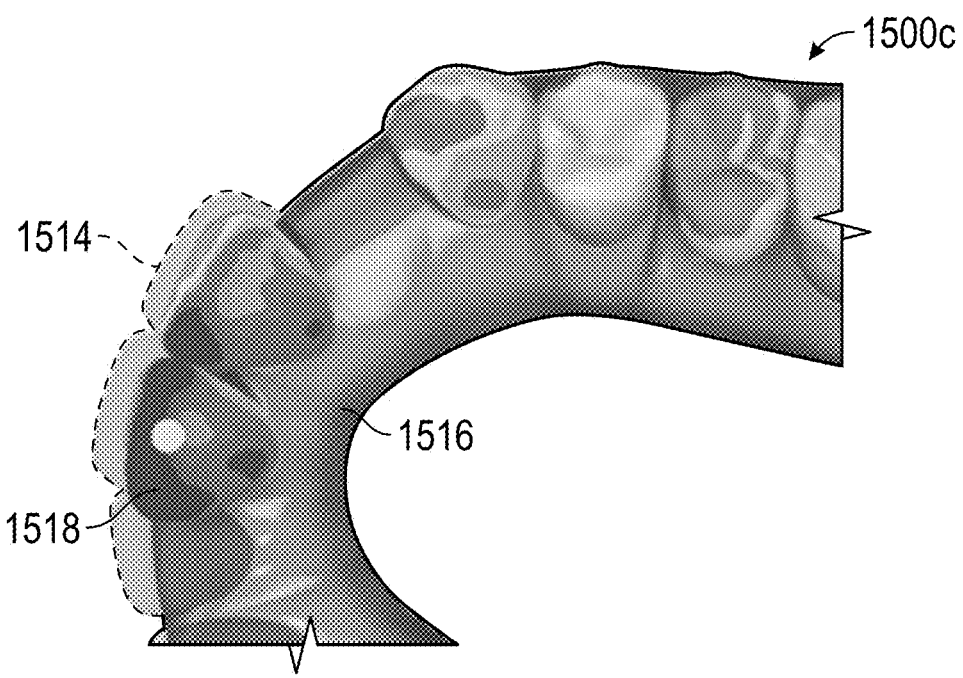

FIG. 15C illustrates a portion of a visualization 1500*c* including a restorative surface overlay 1514. The visualization 1500*c* can include a digital representation 1516 of a tooth arrangement and a heatmap 1518 overlaid onto the digital representation 1516, similar to the embodiments of FIGS. 15A and 15B. The restorative surface overlay 1514 can depict the surfaces of the target tooth arrangement and can be overlaid onto the digital representation 1516 so the user can visually evaluate the differences between the target tooth arrangement and the currently displayed tooth arrangement. In the illustrated embodiment, the restorative surface overlay 1514 has a lower opacity than the digital representation 1516 to make it easier for the user to see the current tooth arrangement. Optionally, the opacity of the restorative surface overlay 1514 can be adjustable (e.g., from 0% to 100%) so the user can alternate between viewing the current tooth arrangement and the target tooth arrangement.

Figure 15D:
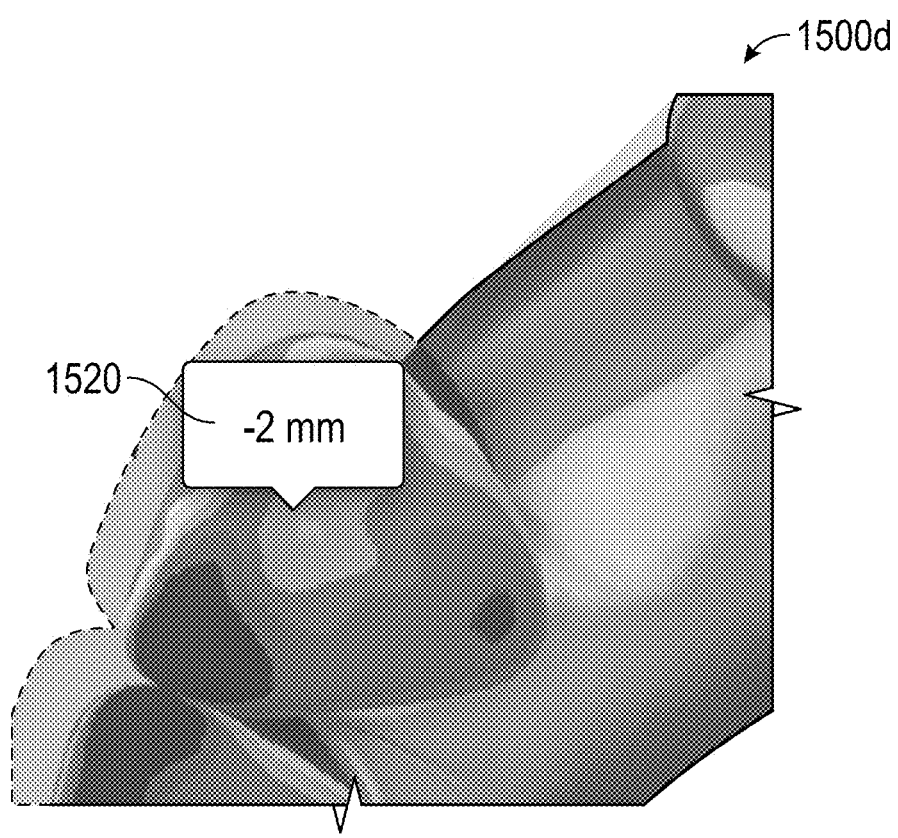

FIG. 15D illustrates a portion of a visualization 1500d including a tooltip 1520. When the user selects or hovers over a location on the digital representation of the teeth, the visualization 1500d can display the tooltip 1520 to show the amount of tooth mass addition or reduction at that location.

Referring again to block 1310 of FIG. 13, the visualization can be used to assist a user in determining the appropriate orthodontic-restorative treatment plan for the patient, e.g., based on factors such as invasiveness, treatment time, treatment complexity, clinician preference, patient preference, etc. In some embodiments, the difference in tooth mass between the target tooth arrangement and the other tooth arrangement correlates to the tooth mass that would need to be added and/or removed to directly achieve the target tooth arrangement from the other tooth arrangement. Stated differently, the tooth mass analysis can show the user how much tooth mass modification would be needed to achieve the target tooth arrangement at that treatment stage, without any further orthodontic repositioning. Accordingly, the visualization can help the user determine the combination of orthodontic repositioning and tooth mass modification that would best achieve the patient's treatment goals. For example, rather than having the patient complete all of the planned orthodontic treatment stages, the user instead can choose to terminate orthodontic treatment at an intermediate treatment stage, and use tooth mass reduction and/or addition to achieve the target tooth arrangement directly from that intermediate treatment stage. Conversely, the user can decide to have the patient complete more orthodontic treatment stages to reduce or minimize the amount of tooth mass reduction and/or addition needed to achieve the target tooth arrangement.

At block 1312, the method 1300 can optionally include receiving user input modifying at least one tooth arrangement, e.g., to adjust the ortho-restorative treatment plan. For example, the user can provide input via the visualization to modify the target tooth arrangement, such as by adjusting the positions of one or more teeth, adding one or more restorative objects to one or more teeth, removing one or more restorative objects from one or more teeth, adjusting the position and/or shape of a restorative object on a tooth, and so on. Subsequently the tooth mass analysis of block 1308 and/or visualization of block 1310 can be updated to reflect the changes to the target tooth arrangement. This process can be repeated to iteratively update the treatment plan based on user feedback.

In some embodiments, once the treatment plan is approved, the method 1300 can further include generating fabrication instructions for manufacturing orthodontic appliances, restorative objects, and/or other devices configured to implement the treatment plan. For example, based on the tooth mass analysis, the user can select the tooth arrangement (e.g., an intermediate tooth arrangement) that is intended to be the final treatment stage for repositioning the patient's teeth. The method 1300 can then determine (1) a series of orthodontic appliances configured to reposition the teeth from the initial tooth arrangement to the selected tooth arrangement, and/or (2) one or more restorative procedures configured to compensate for any differences in mass between the selected tooth arrangement and the target tooth arrangement. For example, if the selected tooth arrangement includes missing tooth mass relative to the target tooth arrangement, one or more restorative objects can be prescribed to fill in the missing tooth mass. As another example, tooth mass reduction can be prescribed if the selected tooth arrangement includes excess tooth mass relative to the target tooth arrangement. The fabrication instructions can be transmitted to a manufacturing system configured to produce the orthodontic appliances and/or restorative objects, as described elsewhere herein.

The method 1300 can be varied in many different ways. For example, some of the processes shown in FIG. 13 can be omitted (e.g., the process of block 1312) and/or the method 1300 can include additional processes not shown in FIG. 13. The method 1300 can be combined with any of the other methods described herein. For instance, some or all of the processes of the method 1300 can be performed as part of the processes of blocks 204 and/or 206 of the method 200 of FIG. 2. Additionally, the processes of blocks 1304 and/or 1310 can incorporate one or more facial lines determined using the method 300 of FIG. 3.

The tooth mass analysis techniques described herein can be used to provide guidance for many different aspects of ortho-restorative treatment planning. For example, the tooth mass analysis can be used to estimate the location and geometry of one or more restorative objects to be used in a treatment plan, including both temporary and permanent restorations. Additionally, the tooth mass analysis techniques can be used to estimate the amount and locations of any tooth preparations (e.g., tooth mass reduction) for accommodating a restorative object, before any actual dental work is started. The visualization of the tooth mass analysis results can provide guidance on the benefits of moving teeth before restoring teeth. In some embodiments, the visualization provides a graphical representation of a minimally invasive approach to preserving healthy natural tooth structure, allowing the user to see the effects of a proposed treatment before making decisions. The visualization can also compare the initial occlusion versus the post-orthodontic treatment tooth mass reduction and/or addition needed to achieve a facially-driven aesthetic smile design goal.

Figure 16A:
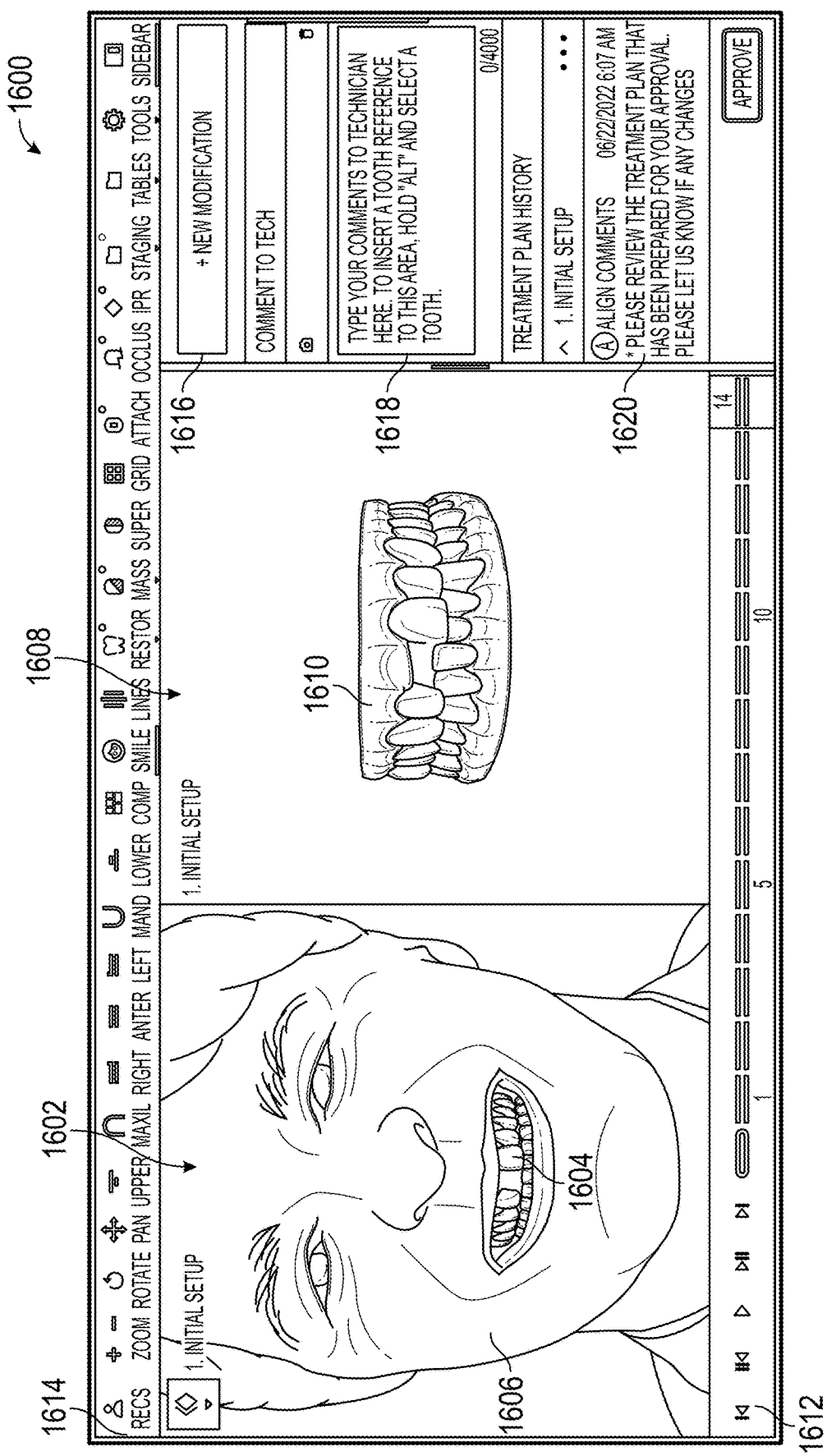
FIG. 16A illustrates a user interface for ortho-restorative treatment planning, in accordance with embodiments of the present technology.
Figure 16B:
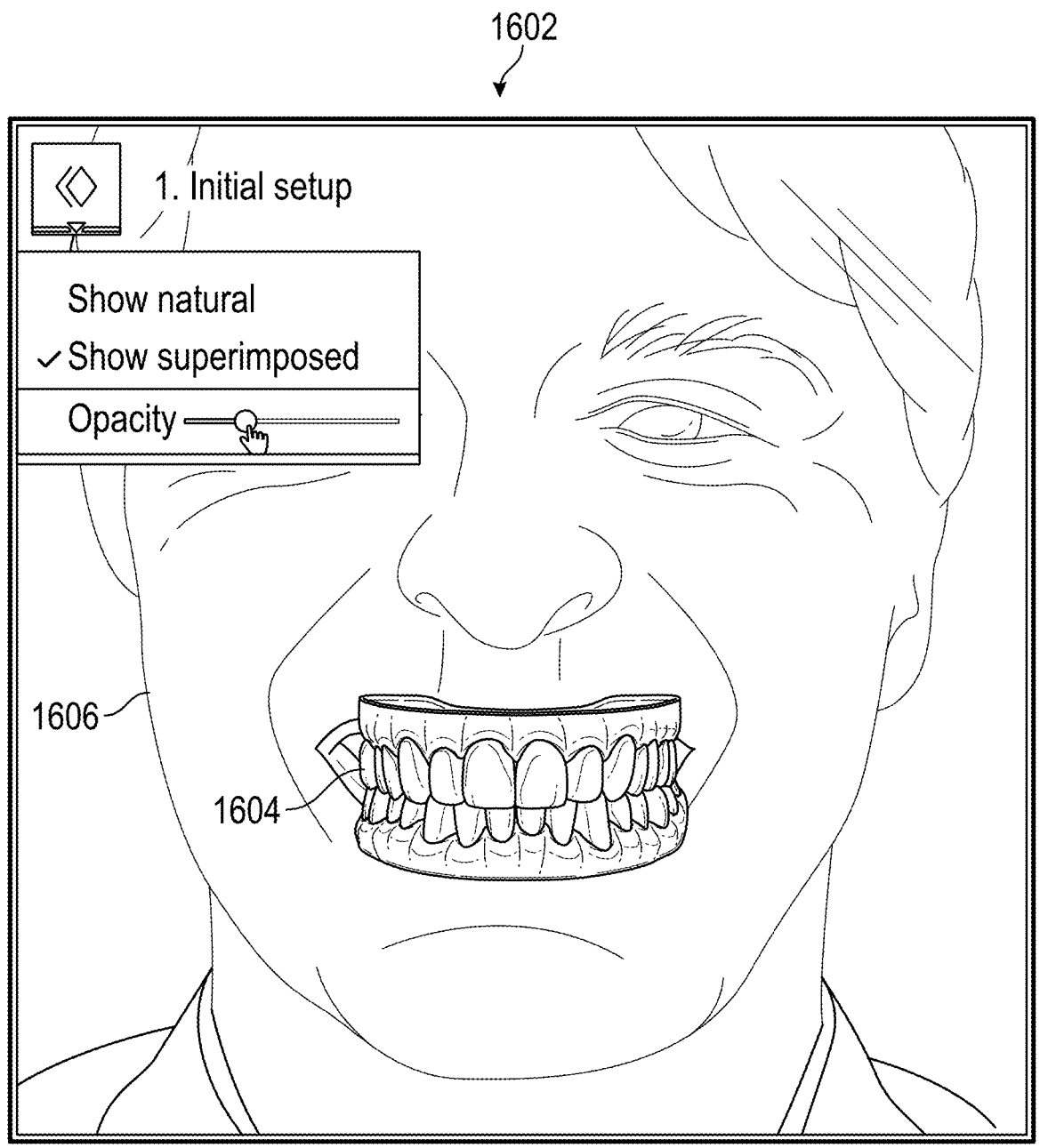
FIG. 16B is a closeup view of an in-face visualization of the user interface of FIG. 16A.
Figure 16C:
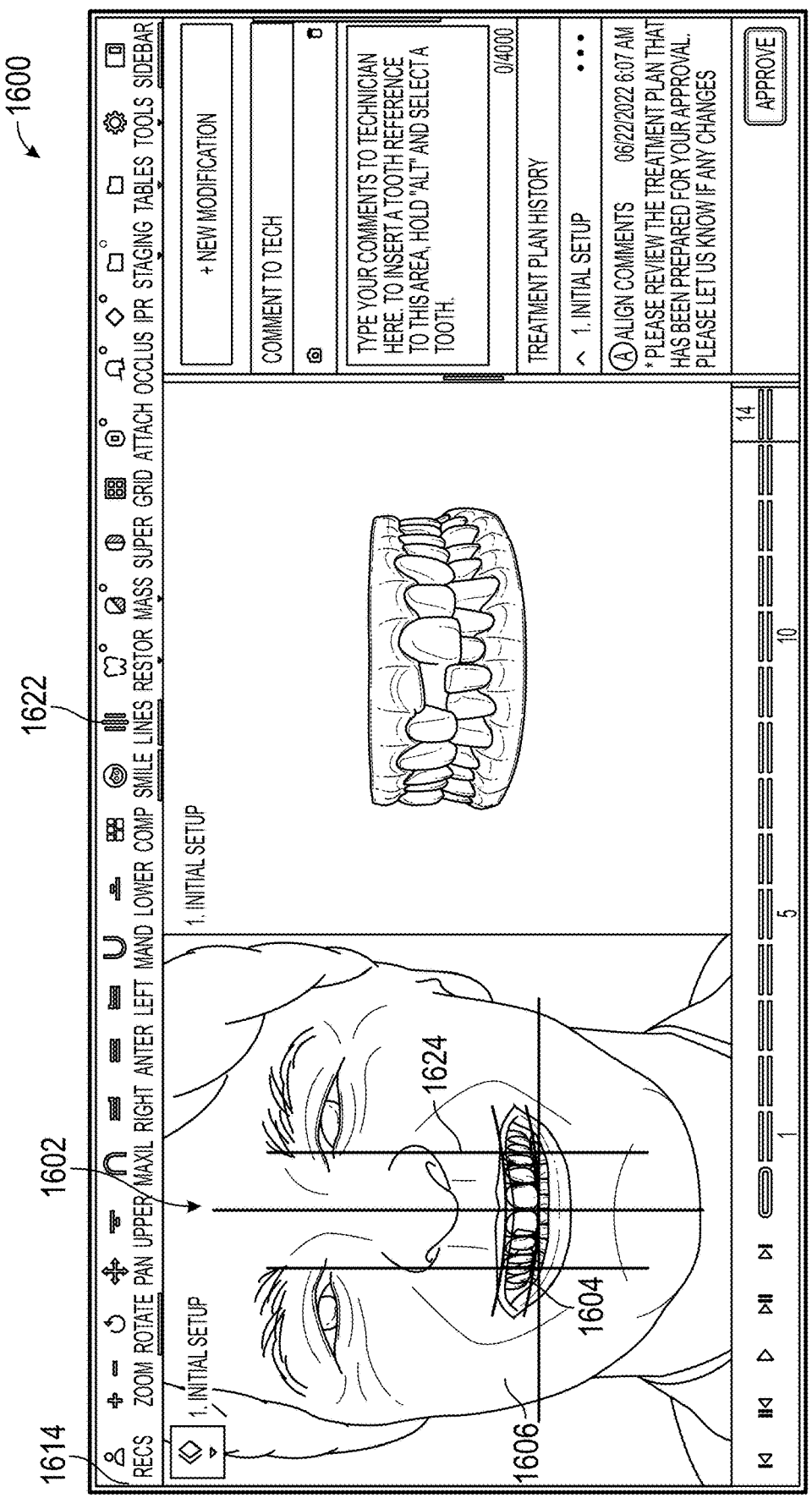
FIG. 16C illustrates a facial lines tool of the user interface of FIG. 16A.
Figure 16D:
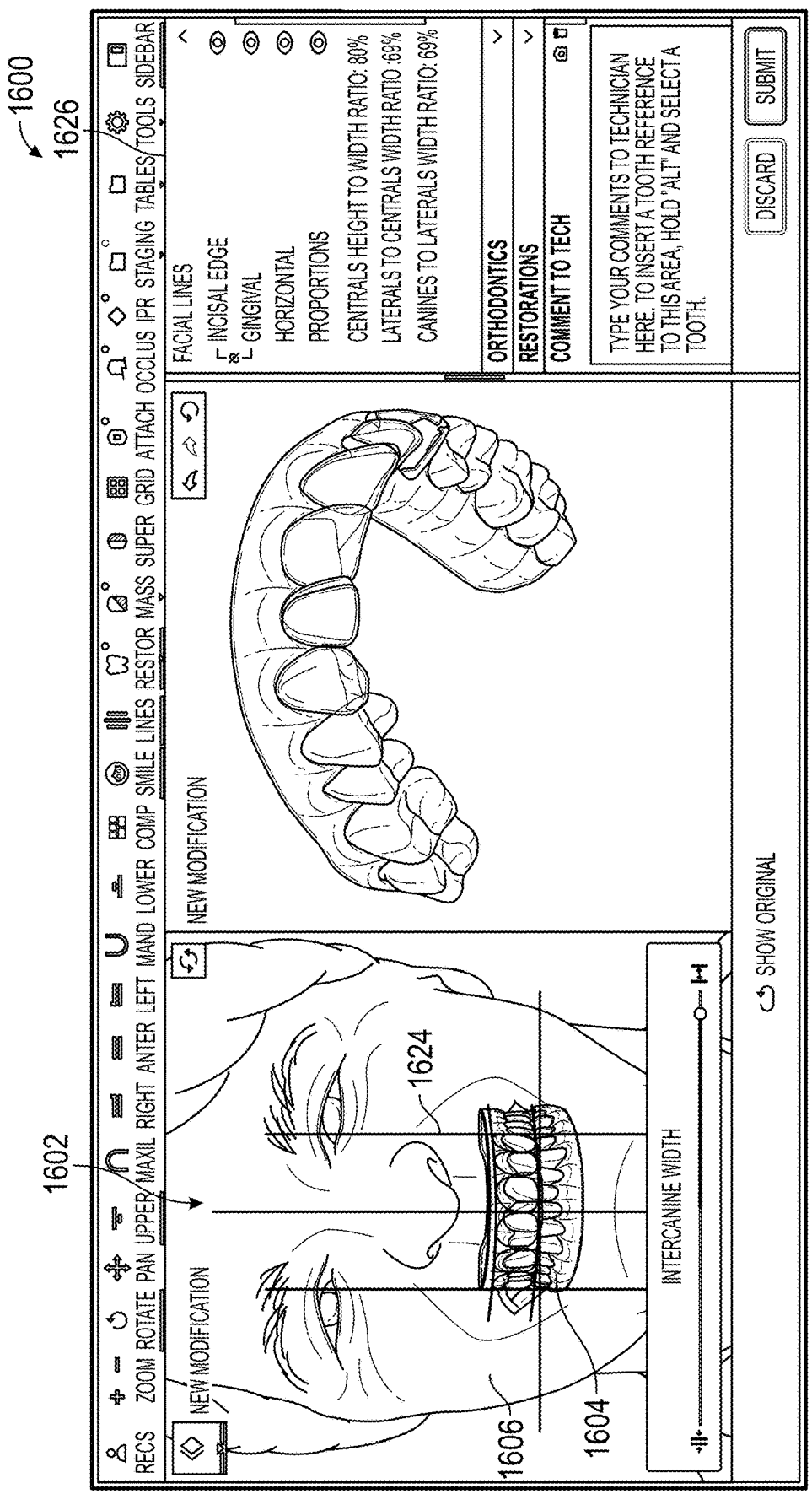
FIG. 16D illustrates a facial lines modification tool of the user interface of FIG. 16A.
Figure 16E:
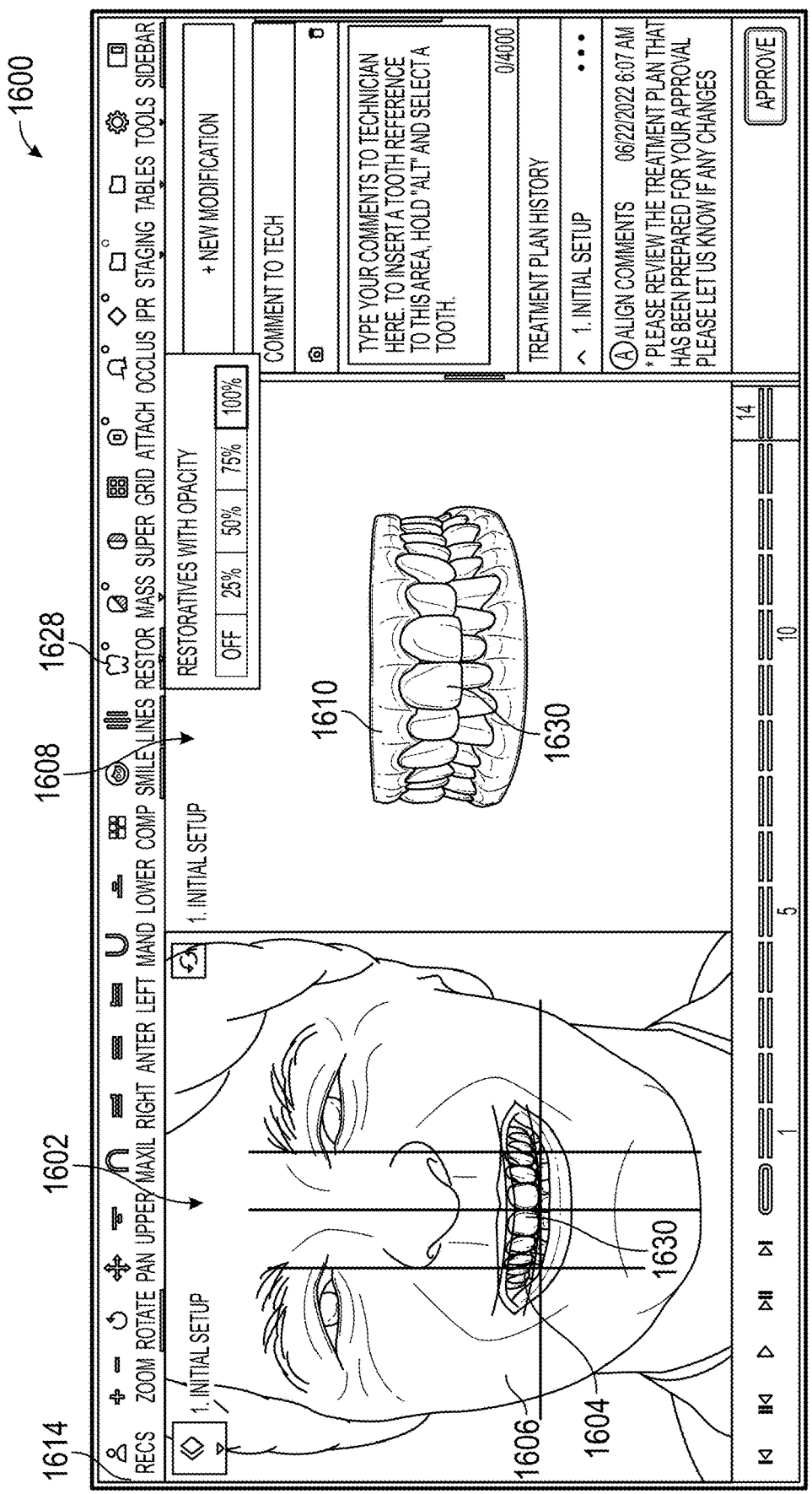
FIGS. 16E and 16F illustrate a restoratives overlay tool of the user interface of FIG. 16A.
Figure 16F:
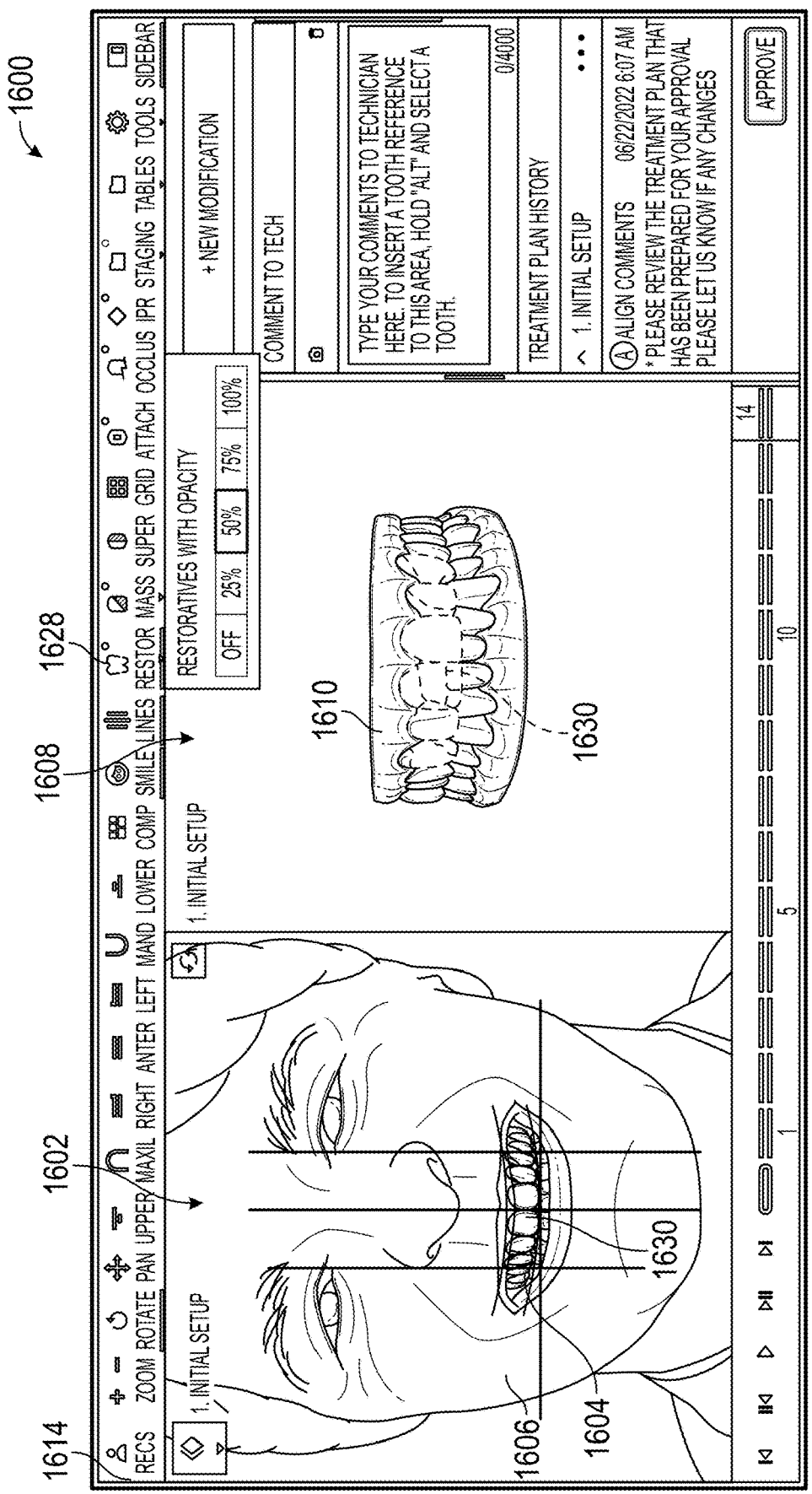
Figure 16G:
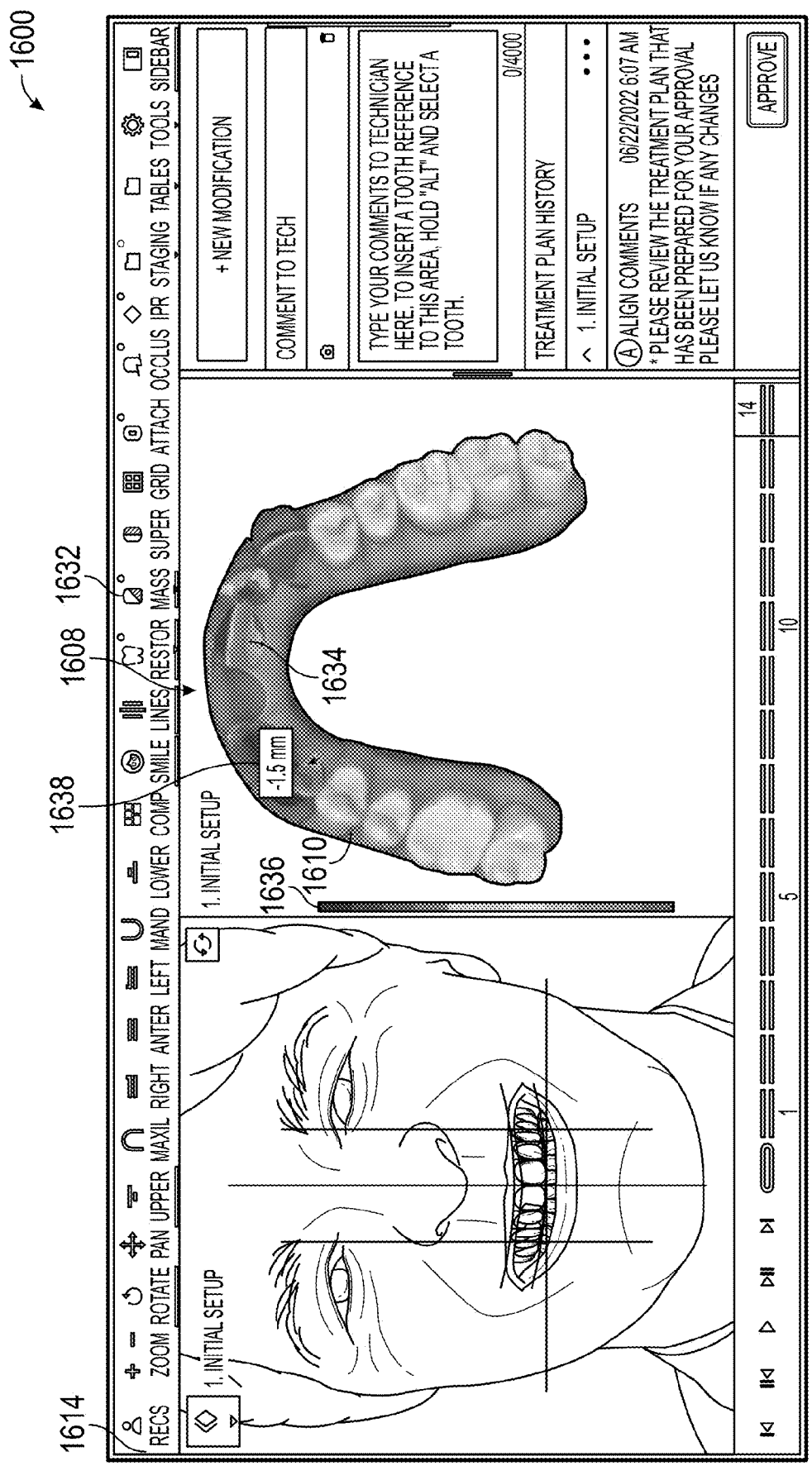
FIG. 16G illustrates a tooth mass analysis tool of the user interface of FIG. 16A.
Figure 16H:
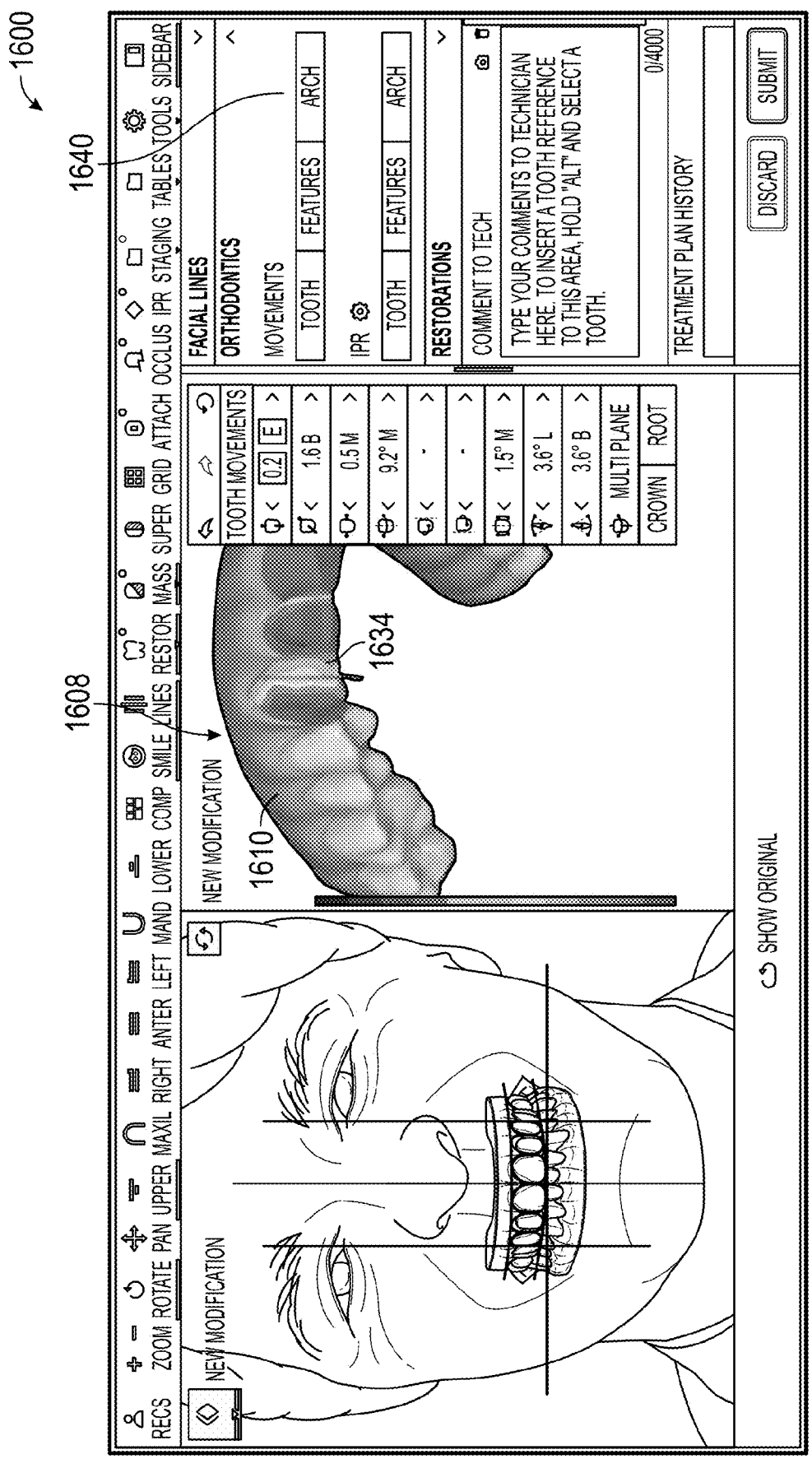
FIG. 16H illustrates an orthodontics modification tool of the user interface of FIG. 16A.
Figure 16I:
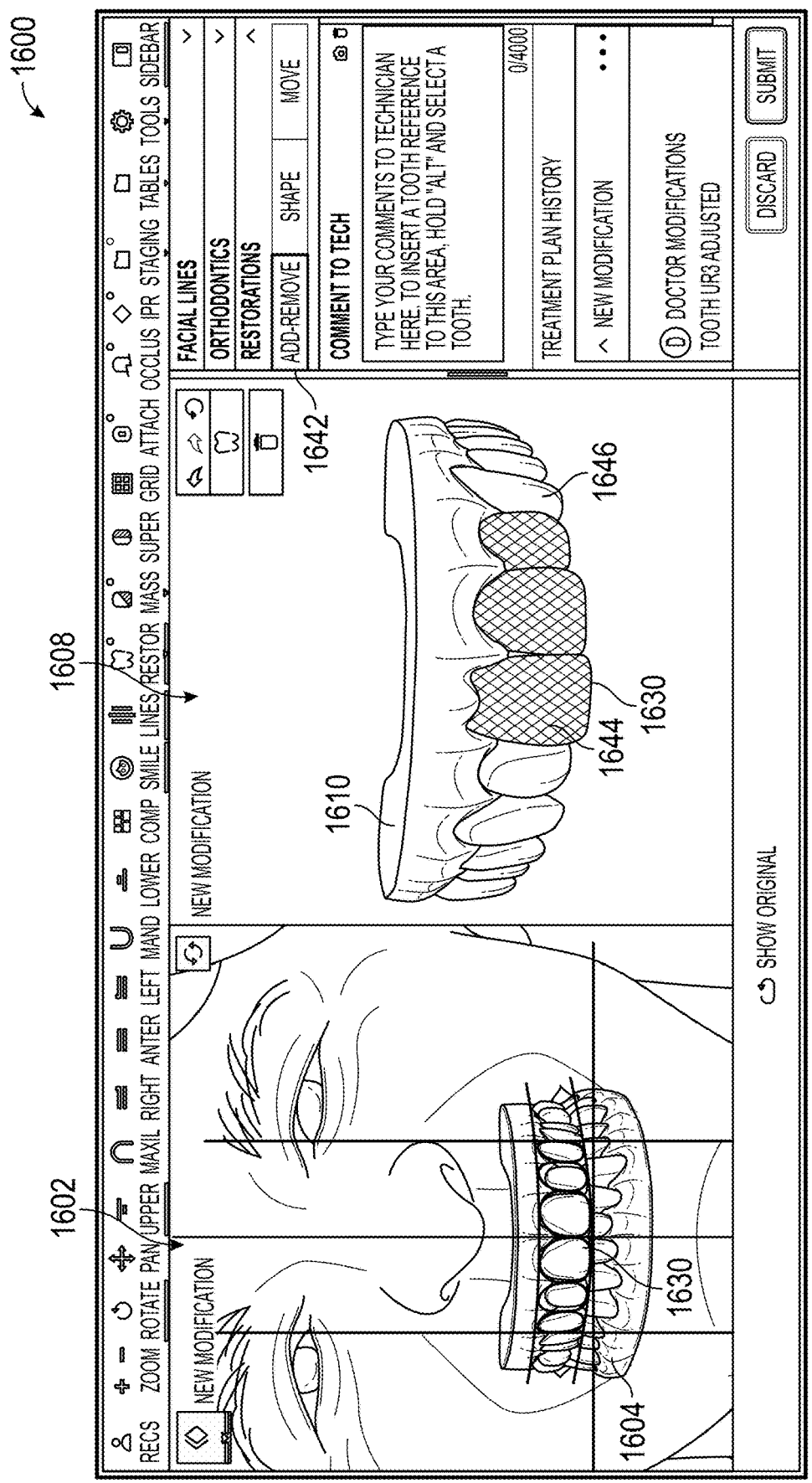
FIGS. 16I-16N illustrate a restorations modification tool of the user interface of FIG. 16A.
Figure 16J:
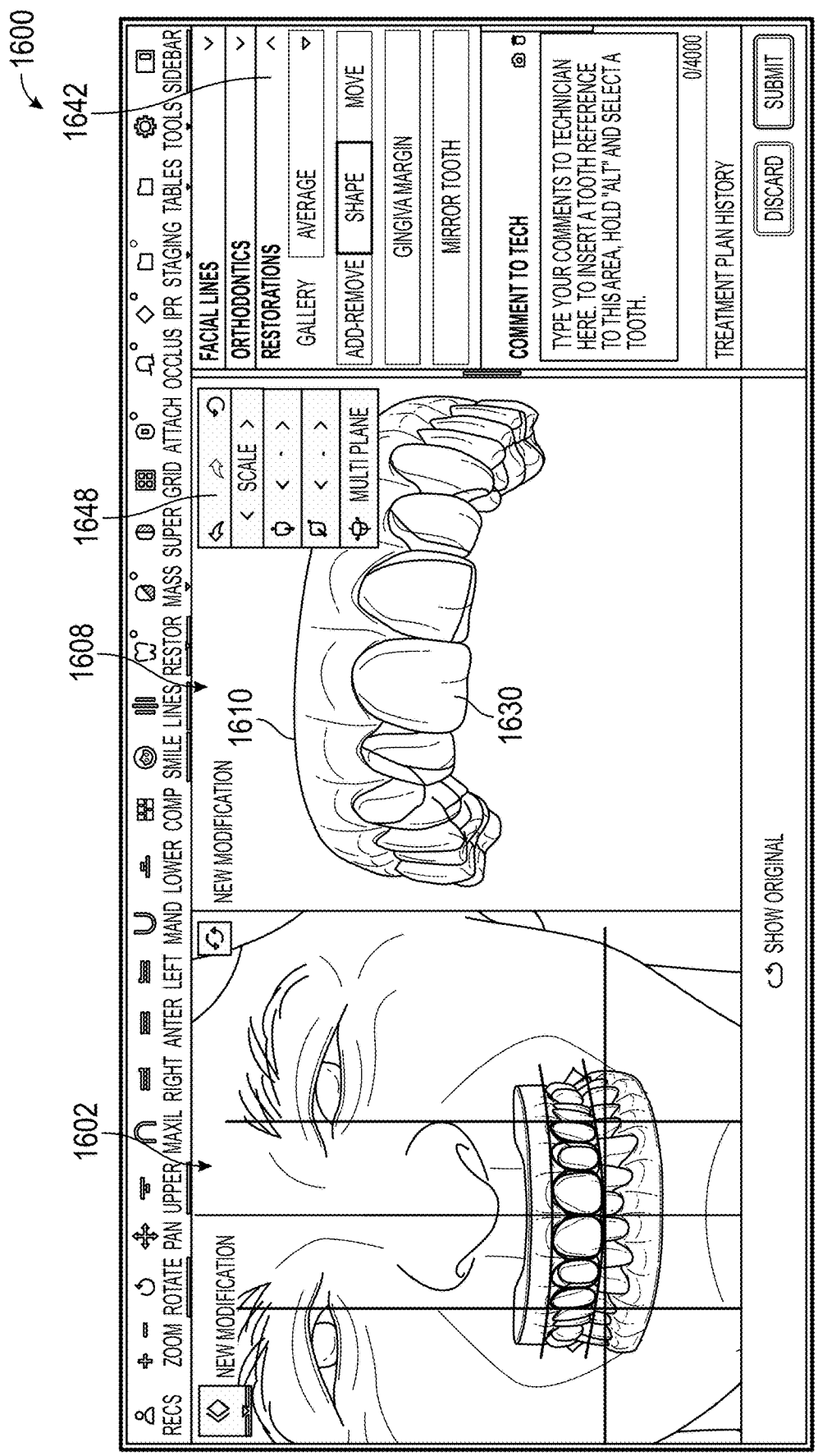
Figure 16K:
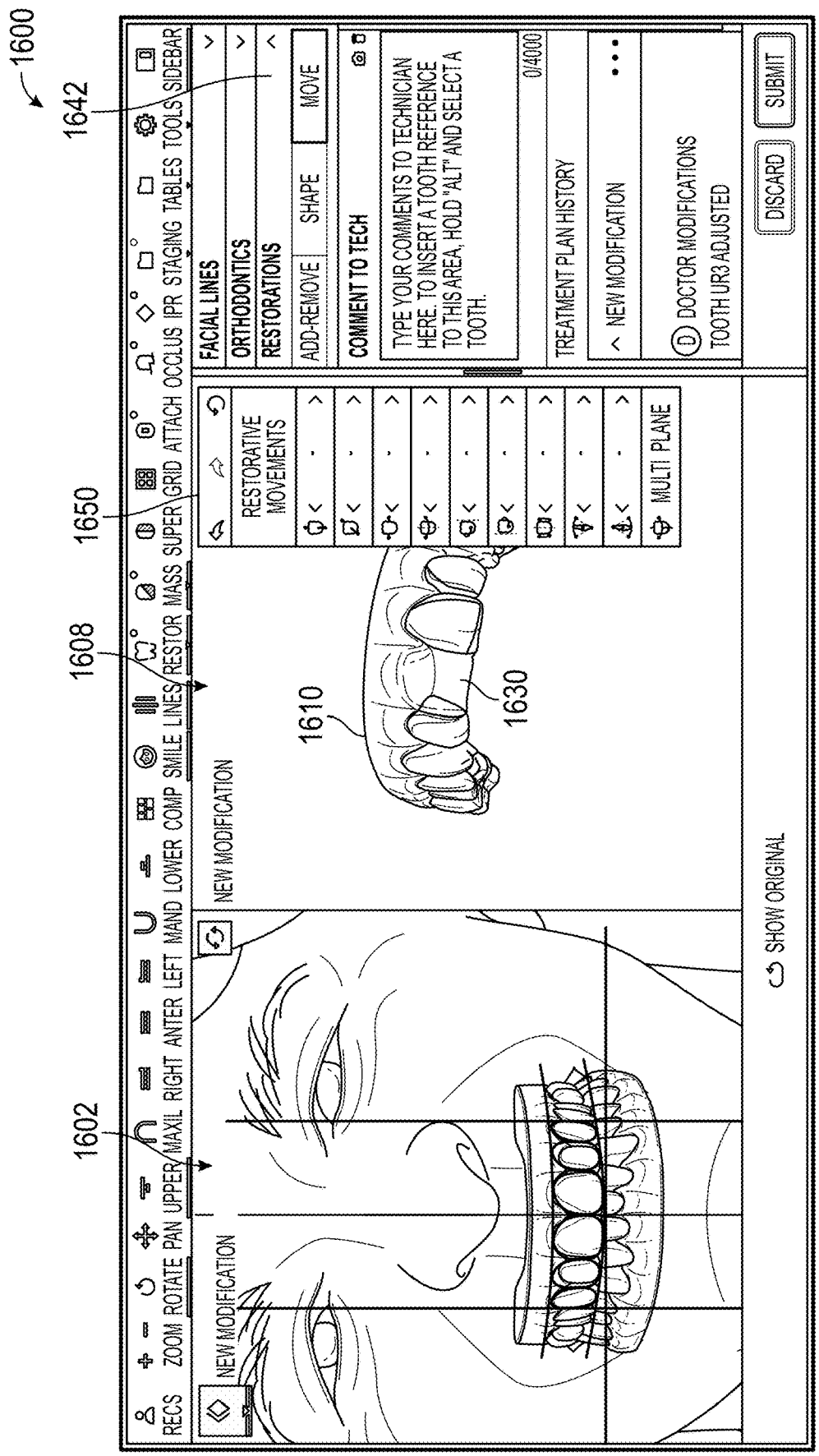
Figure 16L:
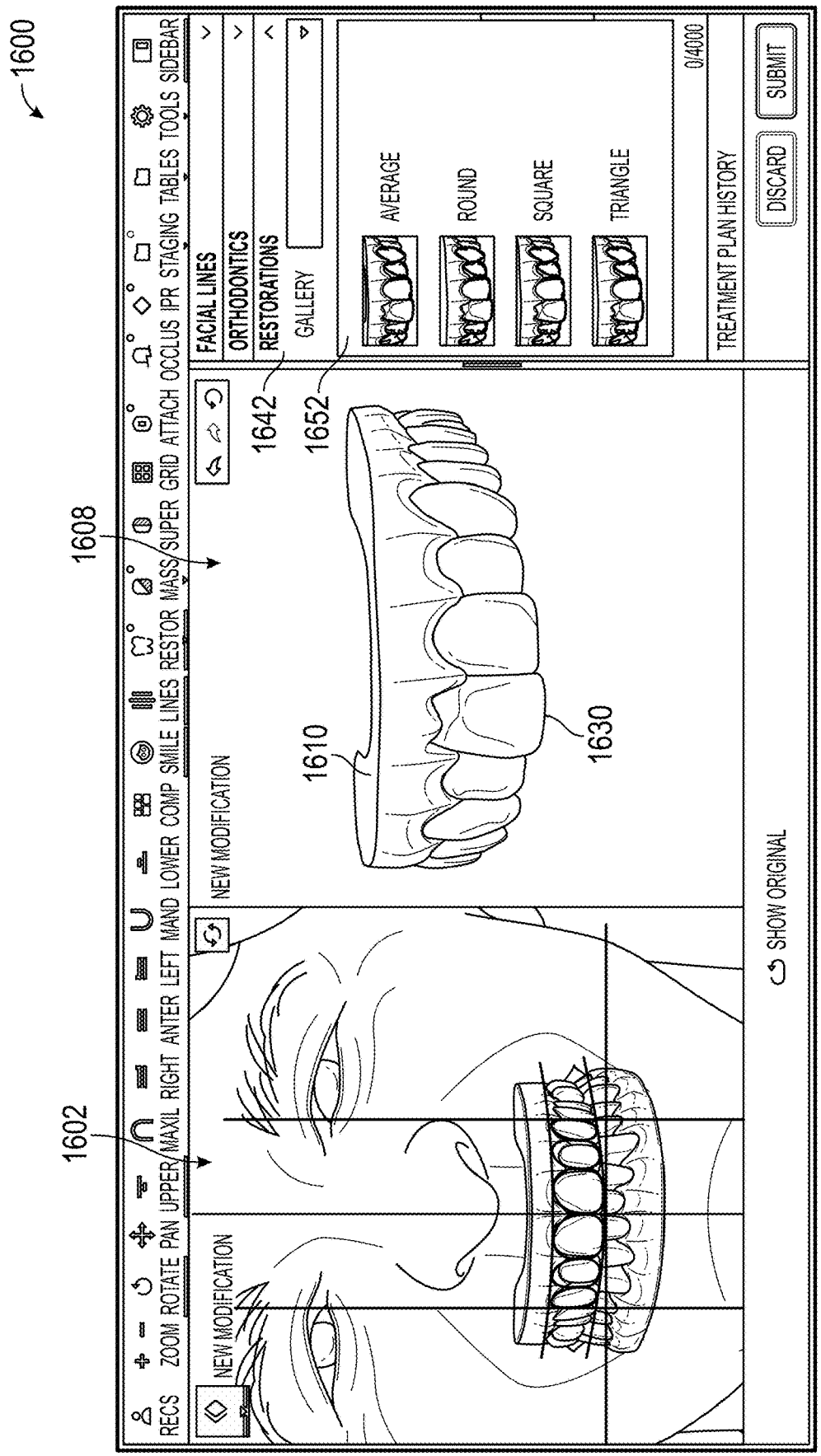
Figure 16M:
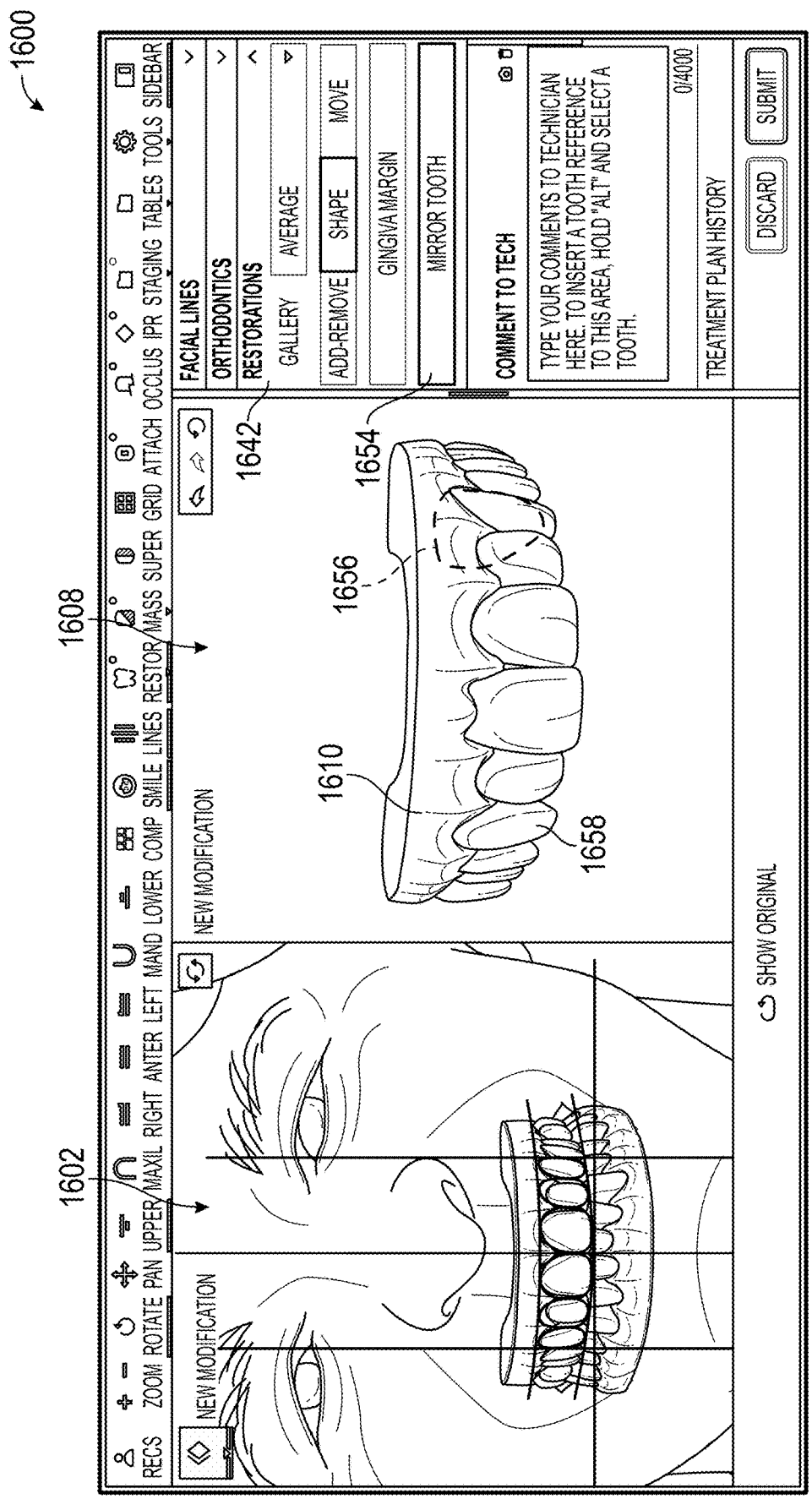
Figure 16N:
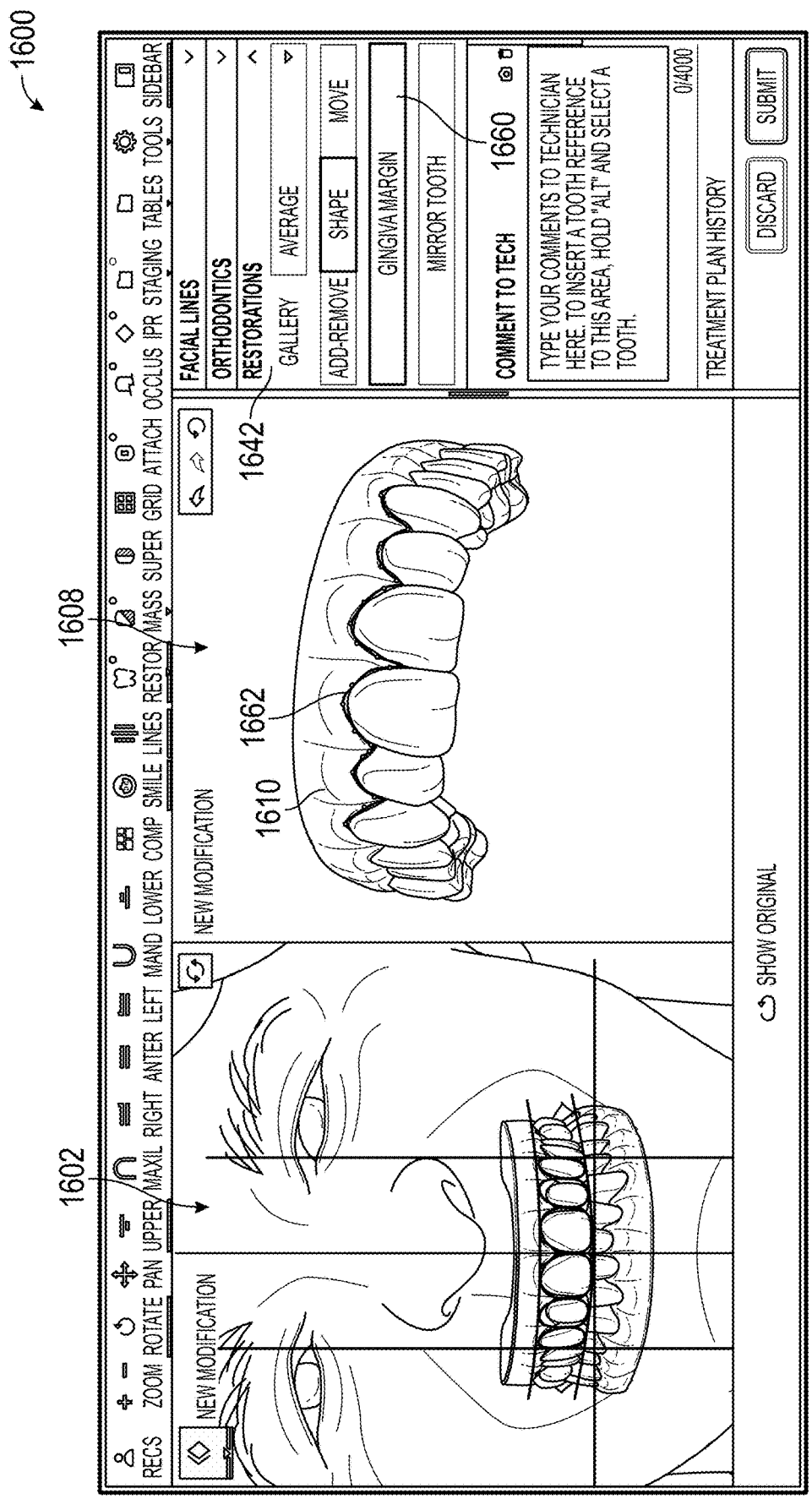
Figure 16O:
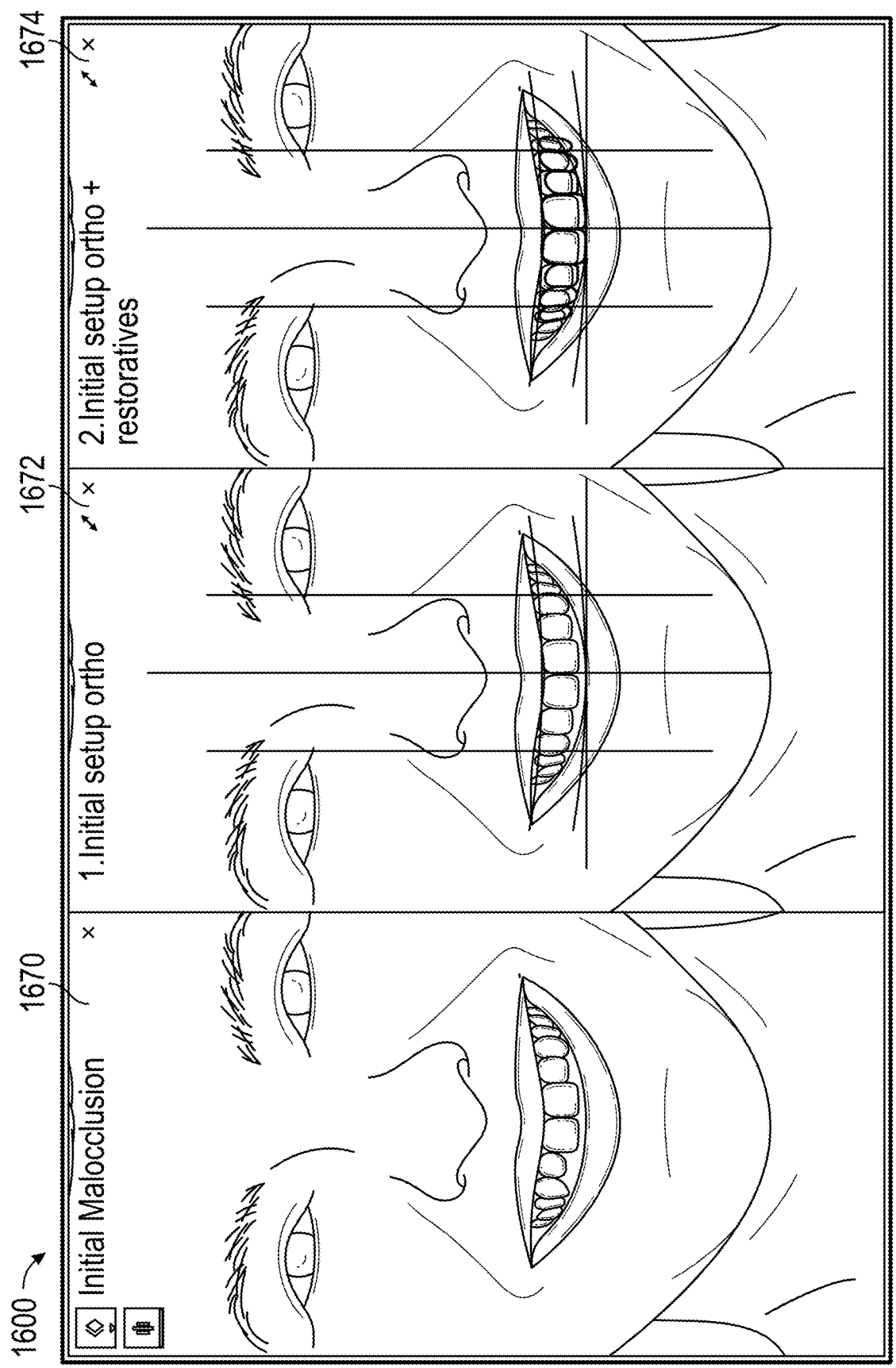
FIG. 16O illustrates a plan comparison tool of the user interface of FIG. 16A.

FIGS. 16A-16O illustrate a representative example of a UI 1600 for ortho-restorative treatment planning, in accordance with embodiments of the present technology. The UI 1600 can be generated by a software platform implemented by the system 100 of FIG. 1 (e.g., by the treatment planning component 104 and/or the treatment visualization component 106), or any other suitable computing system or device. The software platform can provide a single ecosystem for combined visual treatment planning for orthodontics and restorative applications. For example, the platform can provide integrated restorative tools, such as restorative-specific 3D modifications, multi-layer visualization of restoratives overlaid on the teeth, real-time treatment planning, and/or patient/doctor menus, as described in detail below. The UI 1600 can be used in connection with any of the methods described herein, such as the method 200 of FIG. 2, the method 300 of FIG. 3, and/or the method 1300 of FIG. 13.

Referring first to FIG. 16A, the UI 1600 shows an in-face visualization 1602 including a composite image in which a 3D model 1604 of the patient's teeth ("first tooth model 1604") is overlaid onto a 2D image 1606 of the patient's face ("patient image 1606"). The UI 1600 also shows a tooth model visualization 1608 depicting a 3D model 1610 of one or more both dental arches of the patient ("second tooth model 1610"). The first tooth model 1604 of the in-face visualization 1602 can show the teeth in the same arrangement as the second tooth model 1610 of the tooth model visualization 1608. For example, the teeth can be in an initial tooth arrangement prior to treatment, a target tooth arrangement representing the goal of the treatment plan, or an intermediate tooth arrangement corresponding to a particular stage of the treatment plan. The UI 1600 can include a navigation panel 1612 allowing the user to select which tooth arrangement is currently displayed.

The UI 1600 can also include a tool bar 1614 with various tools that allow the user to review and/or modify the treatment plan by manipulating the second tooth model 1610 shown in the tooth model visualization 1608, as described in greater detail below. Modifications can also be made via a modifications panel 1616, as discussed below. The first tooth model 1604 of the in-face visualization 1602 can be dynamically updated along with the second tooth model 1610 of the tooth model visualization 1608, thus allowing the user to assess the effects of the changes on the patient's smile via the in-face visualization 1602. Optionally, the UI 1600 can also include a comments panel 1618 allowing the user to provide written notes to another user (e.g., a technician responsible for finalizing the treatment plan), as well as a history panel 1620 listing any modifications that have been made to the treatment plan.

FIG. 16B is a closeup view of the in-face visualization 1602 of the UI 1600 of FIG. 16A, in accordance with embodiments of the present technology. As shown in FIG. 16B, the user can select various display modes for the in-face visualization 1602. For example, the user can select a "superimposed" display mode in which the opacity of the patient image 1606 is adjustable. In some embodiments, the user can reduce the opacity of the patient image 1606 so the features of the first tooth model 1604 can be more clearly visualized, thus allowing for more detailed review of the displayed tooth arrangement.

Optionally, the user can select a "natural" display mode in which the in-face visualization 1602 shows a simulated patient smile with the selected tooth arrangement. In the natural display mode, the first tooth model 1604 of the teeth can be displayed with lighting, coloration, opacity, etc., that mimics the natural appearance of the teeth. Additionally, the portions of the first tooth model 1604 that would be obstructed by the patient's lips and face can be hidden. The natural display mode can allow the user to assess the overall aesthetics of the teeth together with the patient's facial features.

FIG. 16C illustrates a facial lines tool of the UI 1600, in accordance with embodiments of the present technology. As shown in FIG. 16C, the user can choose to display one or more facial lines 1624 (e.g., facial midline, ICW lines, gingival line, incisal edge line, horizontal line, tooth outlines) overlaid onto the patient image 1606 of the in-face visualization 1602, e.g., by selecting a "lines" button 1622 on the tool bar 1614. The facial lines can be automatically generated from image data of the patient's face (e.g., the patient image 1606), as previously described in connection with the method 300 of FIG. 3. In some embodiments, the facial lines 1624 are smile lines defining a target smile to be achieved through orthodontic-restorative treatment. Accordingly, the user can view the facial lines 1624 as a reference while reviewing and/or modifying the treatment plan.

FIG. 16D illustrates a facial lines modification tool of the UI 1600, in accordance with embodiments of the present technology. The user may choose to modify some or all of the facial lines 1624 in order to adjust the target smile to be achieved via the ortho-restorative treatment plan. In some embodiments, the user can switch between a review mode to view the facial lines 1624 superimposed on the in-face visualization 1602, and a modification mode to make adjustments to one or more of the facial lines 1624. The color of the facial lines 1624 can change to indicate the corresponding mode, e.g., white for review mode (no modifications permitted) and blue for modification mode. Optionally, the facial line 1624 that is currently being modified can be shown in a different color than the other facial lines 1624.

As shown in FIG. 16D, the UI 1600 can include a facial lines modification panel 1626 with tools allowing the user to view, hide, and/or modify any of the facial lines 1624. For example, the user can directly select and modify the position, orientation, and/or shape of each facial line 1624 in the in-face visualization 1602. Alternatively or in combination, the user can modify the facial lines 1624 via controls (e.g., sliders, buttons, text entry boxes, etc.) shown in the facial lines modification panel 1626 and/or the in-face visualization 1602. In some embodiments, the tooth proportions of the target smile (e.g., laterals to centrals width ratio, centrals height to width ratio, canines to lateral width ratio) are automatically updated based on changes to the facial lines 1624, and/or vice-versa.

Representative examples of changes that can be made to the facial lines 1624 include, but are not limited to, any of the following:

Facial midline: move left, move right, rotate;
Incisal edge line: decrease curvature of left incisal edge line, increase curvature of left incisal edge line, decrease curvature of right incisal edge line, increase curvature of right incisal edge line, rotate, adjust left and right incisal edge lines together, adjust left and right incisal edge lines independently;
Gingival line: decrease curvature of left gingival line, increase curvature of left gingival line, decrease curvature of right gingival line, increase curvature of right gingival line, rotate, adjust left and right gingival lines together, adjust left and right gingival lines independently;
Horizontal line: move up, move down, rotate;
ICW lines: decrease ICW, increase ICW; and/or
Tooth proportions: adjust laterals to centrals width ratio, adjust centrals height to width ratio, adjust canines to lateral width ratio.

In some embodiments, the changes to the facial lines 1624 do not automatically produce any corresponding changes to the tooth arrangements of the treatment plan. Instead, the modified facial lines 1624 are used as a visual reference while the user manually adjusts one or more tooth arrangements of the treatment plan. In other embodiments, however, some or all of the tooth arrangements can be automatically updated based on the modified facial lines 1624. For example, the positions and/or shapes of one or more teeth in the target tooth arrangement can be adjusted so the resulting smile conforms to the target smile defined by the modified facial lines 1624; subsequently, some or all of the intermediate tooth arrangements can be adjusted accordingly to account for the changes to the target tooth arrangement.

FIGS. 16E and 16F illustrate a restoratives overlay tool of the UI 1600, in accordance with embodiments of the present technology. Referring to FIG. 16E, when the user activates the restoratives overlay tool (e.g., by selecting a "restoratives" button 1628 on the tool bar 1614), the UI 1600 can display the tooth mass modifications prescribed by the treatment plan in the in-face visualization 1602 and/or the tooth model visualization 1608. For example, the UI 1600 can display the locations and amounts of tooth mass addition (e.g., via restorative objects such as crowns, veneers, edge bonding, composites, prosthetics, etc.) and/or tooth mass reduction to achieve a target smile and/or target tooth arrangement, as described elsewhere herein.

In the illustrated embodiment, when the restoratives overlay tool is activated, the UI 1600 displays a model 1630 of at least one restorative object ("restoratives model 1630") overlaid onto the second tooth model 1610 in the tooth model visualization 1608 and/or the first tooth model 1604 of the in-face visualization 1602. The restoratives model 1630 can depict the surfaces and/or volumes of the teeth after the restorative object(s) have been applied. Optionally, the user can choose to display the restoratives model 1630 overlaid on the first tooth model 1604 only, the second tooth model 1610 only, or both.

In some embodiments, the user can adjust the opacity of the restoratives model 1630 shown in the UI 1600. For example, at 100% opacity (FIG. 16E), the restoratives model 1630 can be depicted as being fully opaque and having the same color as the teeth in the first and/or second tooth models 1604, 1610. Accordingly, the user can view the final shapes and positions of the teeth after the restorative objects are applied. At lower opacity settings (e.g., 25%, 50%, 75%), the restoratives model 1630 can be partially opaque and/or in a different color than the teeth in the first and/or second tooth models 1604, 1610, e.g., as represented by the broken lines in FIG. 16F. Accordingly, the user can compare the shapes and positions of the teeth in the currently displayed tooth arrangement to the shapes and positions of the teeth with the restoratives object applied. At 0% opacity, the restoratives model 1630 can be hidden, thus allowing the user to view the current tooth arrangement only.

FIG. 16G illustrates a tooth mass analysis tool of the UI 1600, in accordance with embodiments of the present technology. When the user activates the tooth mass analysis tool (e.g., by selecting the "mass" button 1632 on the tool bar 1614), the UI 1600 can display a heatmap overlay 1634 on the second tooth model 1610 of the tooth model visualization 1608 that shows any differences in mass between the currently displayed tooth arrangement and the target tooth arrangement. The difference in mass can be determined by comparing the positions and shapes of the teeth in the current tooth arrangement to the positions and shapes of the teeth in the target tooth arrangement, as previously described with respect to the method 1300 of FIG. 13. The heatmap overlay 1634 can depict the locations and amounts of tooth mass reduction only (e.g., when "reduction mode" is selected), or can depict the locations and amounts of tooth mass reduction and addition (when "reduction and addition mode" is selected). The UI 1600 can also a display a legend 1636 indicating how the different colors of the heatmap overlay 1634 correlate to the amounts of tooth mass reduction and/or addition. Optionally, when the user selects or hovers over a portion of the second tooth model 1610, the UI 1600 can show a tooltip 1638 quantifying the amount of tooth mass reduction and/or addition at that portion.

FIG. 16H illustrates an orthodontics modification tool of the UI 1600, in accordance with embodiments of the present technology. The user may choose to modify the positions of some or all of the teeth in the currently displayed tooth arrangement (e.g., an intermediate tooth arrangement or the target tooth arrangement) in order to adjust the corresponding orthodontic treatment stage of the ortho-restorative treatment plan. As shown in FIG. 16H, the UI 1600 can include an orthodontics modification panel 1640 with tools allowing the user to make various orthodontic adjustments to the displayed tooth arrangement, such as intrusion, extrusion, rotation, torque, mesialization, distalization, etc. The user can also directly manipulate the teeth of the second tooth model 1610 in the tooth model visualization 1608. In some embodiments, the tooth mass analysis is dynamically recalculated and the heatmap overlay 1634 is automatically updated to reflect the modifications to the displayed tooth arrangement.

FIGS. 16I-16N illustrate a restorations modification tool of the UI 1600, in accordance with embodiments of the present technology. The user may choose to modify the positions and/or shapes of at least one restorative object in the currently displayed tooth arrangement (e.g., an intermediate tooth arrangement or the target tooth arrangement) in order to adjust the target smile and/or tooth arrangement to be achieved via ortho-restorative treatment.

Referring first to FIG. 16I, the UI 1600 can include a restorations modification panel 1642 with tools allowing the user to make various adjustments to the displayed restorative object(s). For example, the user can add or remove a restorative object from a tooth (or, in the case of restorative objects used to replace a missing tooth, from the patient's arch). When the user adds a restorative object, the UI 1600 can display a restoratives model 1630 at the corresponding location in the first tooth model 1604 of the in-face visualization 1602 and/or the second tooth model 1610 of the tooth model visualization 1608. Optionally, teeth 1644 that include restorative objects can be depicted with a different visual appearance (e.g., a different color-represented by hatching in FIG. 16I) than teeth 1646 that do not include any restorative objects.

Referring next to FIG. 16J, the restorations modification tool can allow the user to change the geometry of a restorative object. The changes can be made by directly selecting and manipulating the corresponding restoratives model 1630 shown in the tooth model visualization 1608, through a restoratives shape control panel 1648 (e.g., via sliders, buttons, text input boxes), or a combination thereof. The in-face visualization 1602 and/or the tooth mass analysis results (e.g., heatmap overlay 1634—not shown) can be updated in real-time to reflect the changes made.

Representative examples of changes to the geometry of a restorative object that can be made include, but are not limited to, any of the following:

- Adjusting the scale of a restorative object (e.g., mesial/distal/buccal/lingual, extrusion);
- Adjusting the size of a restorative object (e.g., mesial/distal, buccal/lingual, extrusion); and/or
- Adjusting the shape of a restorative object (e.g., upper third (mesial/distal), upper third (buccal/lingual), middle third (mesial/distal), middle third (buccal/lingual), lower third (mesial/distal), lower third (buccal/lingual), extrusion/intrusion).

Referring next to FIG. 16K, the restorations modification tool can allow the user to change the position of a restorative object. The changes can be made by directly selecting and manipulating the corresponding restoratives model 1630 shown in the tooth model visualization 1608, through a restorative movements control panel 1650 (e.g., via sliders, buttons, text input boxes), or a combination thereof. The in-face visualization 1602 and/or the tooth mass analysis results (e.g., heatmap overlay 1634—not shown) can be updated in real-time to reflect the changes made.

Representative examples of changes to the position of a restorative object that can be made include, but are not limited to, any of the following:

- Extrusion/intrusion;
- Translation (e.g., buccal/lingual, mesial/distal);
- Rotation (e.g., mesial hinge rotation, distal hinge rotation);

Crown angulation (e.g., mesial/distal);
Root torque (e.g., buccal/lingual); and/or
Crown tip (e.g., buccal/lingual).

Referring next to FIG. 16L, the restorations modification tool can include a gallery menu 1652 allowing the user to adjust the overall shape of the teeth via one or more restorative objects to conform to a preset shape profile. For example, as shown in FIG. 16L, the preset shape profiles can include an average shape profile, a round shape profile, a square shape profile, and/or a triangle shape profile. The in-face visualization 1602, tooth model visualization 1608, and/or the tooth mass analysis results (e.g., heatmap overlay 1634—not shown) can be updated in real-time to reflect the selected shape profile.

Referring next to FIG. 16M, the restorations modification tool can include a "mirror tooth" tool 1654 that generates at least one restorative object 1656 that, when applied to an existing tooth (or to a location in the arch, when used to replace a missing tooth), automatically mirrors the shape of a corresponding (e.g., contralateral) tooth 1658. This technique can be advantageous for quickly creating a target smile that is generally symmetric across the facial midline. The restorative object 1656 can be superimposed on the second tooth model 1610 of the tooth model visualization 1608 so the user can preview the shape and location of the restorative object 1656. Additionally, the in-face visualization 1602 and/or the tooth mass analysis results (e.g., heatmap overlay 1634—not shown) can be updated in real-time to reflect the added restorative object 1656.

Referring next to FIG. 16N, the restorations model tool can include a "gingiva margin" tool 1660 that allows the user to adjust the gingival margin of the target tooth arrangement. As shown in FIG. 16N, the user can directly manipulate one or more points defining the gingival margin 1662 on the second tooth model 1610 of the tooth model visualization 1608. The in-face visualization 1602 can be updated in real-time to reflect the changes to the gingival margin 1662. The gingiva margin tool 1660 can allow the user to preview the results of a gingivectomy and/or other soft tissue/bone modeling procedures, in combination with the ortho-restorative treatment procedures described herein.

FIG. 16O illustrate a plan comparison tool of the UI 1600, in accordance with embodiments of the present technology. The plan comparison tool can allow the user to visually compare and assess the differences between multiple treatment plans. In the illustrated embodiment, the plan comparison tool concurrently displays a plurality of in-face visualizations: a first in-face visualization 1670 showing an image of the patient's face with teeth in the initial arrangement, a second in-face visualization 1672 showing a composite image of the patient's face combined with a model of the teeth in an arrangement (e.g., intermediate or target arrangement) of a first treatment plan, and a third in-face visualization 1674 showing a composite image of the patient's face combined with a model of the teeth in an arrangement (e.g., intermediate or target arrangement) of a second treatment plan. The in-face visualizations can be displayed in a side-by-side format to facilitate visual comparison and review. Optionally, some or all of the displayed in-face visualizations can include one or more facial lines overlaid onto the image of the patient's face.

The first treatment plan can differ from the second treatment plan with respect to any of the following: treatment modality (e.g., orthodontics only, restorative only, ortho-restorative), number of treatment stages, teeth to be repositioned, tooth movements (e.g., movement type, movement direction, movement velocity), tooth mass addition (e.g., amount, locations), tooth mass reduction (e.g., amount, location), and/or other treatment parameters (e.g., changes to the gingival line). For example, as shown in FIG. 16O, the second in-face visualization 1672 shows a tooth arrangement for an orthodontics-only treatment plan, and the third in-face visualization 1674 shows a tooth arrangement for an ortho-restorative treatment plan.

In other embodiments, the second in-face visualization 1672 and the third in-face visualization can each independently be selected from any of the following: an orthodontics-only treatment plan, a restorative-only treatment plan, or an ortho-restorative treatment plan. Optionally, the plan comparison tool can be used to compare different stages of a single treatment plan, e.g., the second in-face visualization 1672 can show a first stage of a treatment plan, and the third in-face visualization 1674 can show a second stage of the treatment plan. Additionally, the plan comparison tool can show the treatment plans and/or stages in different formats. For example, the plan comparison tool can show 3D tooth models of the different treatment plans and/or stages, in addition or as an alternative to the in-face visualizations.

Figure 17A:
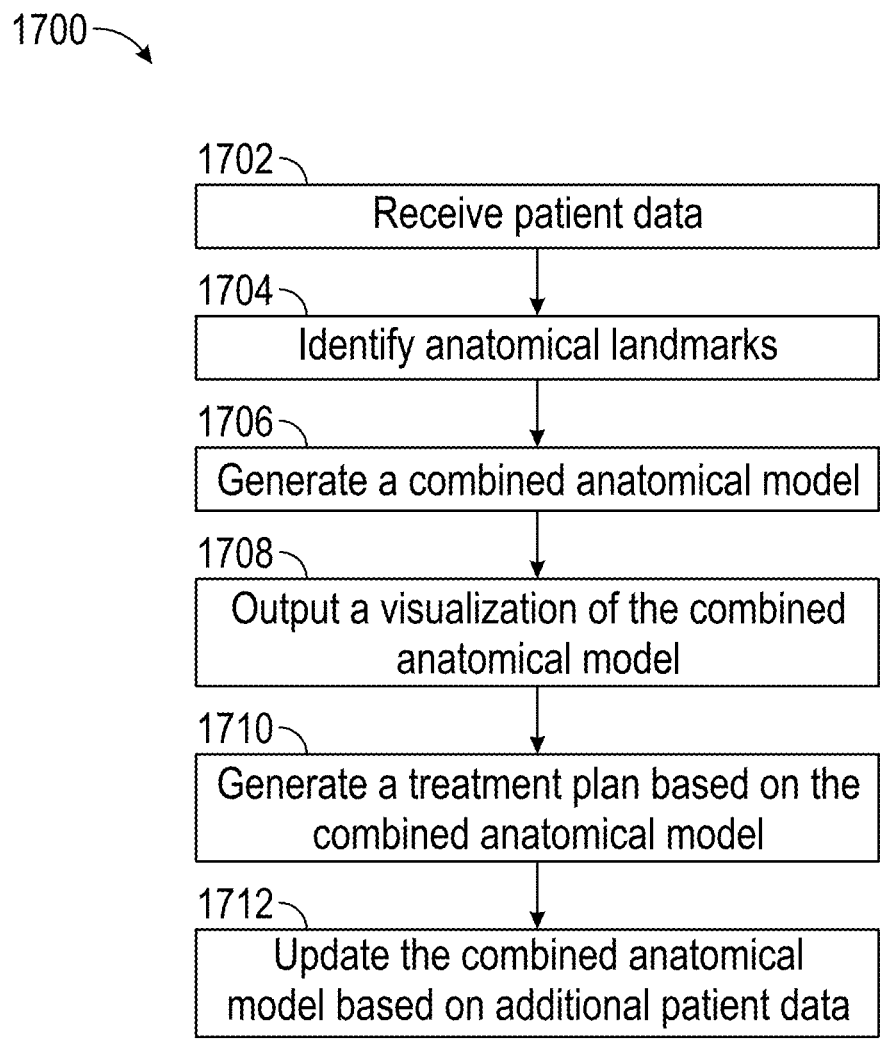
FIG. 17A is a flow diagram illustrating a method for planning and/or monitoring a treatment procedure, in accordance with embodiments of the present technology.

FIG. 17A is a flow diagram illustrating a method 1700 for planning and/or monitoring a treatment procedure, in accordance with embodiments of the present technology. As described in detail below, the method 1700 can be used to combine different types of patient data assets into a single unified model, thus allowing a user (e.g., a clinician or technician) to visualize all the relevant patient data in context with each other and/or over time. This approach can make it easier for the user to review data from multiple modalities when planning a treatment procedure. Additionally, the techniques described herein can be used to provide automated treatment planning and/or progress tracking capabilities, based on the patient's specific craniofacial anatomy.

The method 1700 can be performed using any suitable system or device. In some embodiment, some or all of the processes of the method 1700 are implemented as computer-readable instructions (e.g., program code) that are configured to be executed by one or more processors of a computing device. For example, some or all of the processes of the method 1700 can be performed by one or more components of the system 100 of FIG. 1, such as the data input component 102, the treatment planning component 104, and/or the treatment visualization component 106.

The method 1700 begins at block 1702 with receiving patient data. The patient data can include any data relevant to a treatment procedure for the patient's teeth (e.g., an orthodontic treatment procedure, a restorative treatment procedure, or an ortho-restorative treatment procedure). For example, the patient data can depict the hard and/or soft tissue of the patient's craniofacial region, such as the teeth, gingiva, one or both dental arches, intraoral cavity, jaws, face, etc. The patient data can include a combination of multiple data types, such as one or more of the following: photographs, videos, scan data (e.g., intraoral and/or extraoral scans), MRI data, radiographic data (e.g., bitewing x-ray data, panoramic x-ray data, cephalometric x-ray data, CT data, CBCT data, fluoroscopy data), and/or motion data. Optionally, the patient data can include any suitable combination of 2D data, 3D data, and/or 4D data.

| At block 1704, the method 1700 can include identifying one or more anatomical landmarks of the patient, based on the patient data. The anatomical landmarks can include soft tissue landmarks (e.g., facial landmarks, such as the facial landmarks depicted in FIG. 8A), hard tissue landmarks (e.g., cranial landmarks), or combinations thereof. The anatomical landmarks can be detected from the patient data using any suitable technique, such as manually by a user, automatically by a computing device (e.g., the treatment planning component 104 of FIG. 1), or suitable combinations thereof. For example, anatomical landmarks can be detected from images, scans, and/or similar data types using computer vision techniques and/or machine learning algorithms (e.g., CNNs, RNNs, regression techniques, and/or other deep learning techniques), as described elsewhere herein.

At block 1706, the method 1700 can include generating a combined anatomical model, based on the identified anatomical landmarks. The combined anatomical model can be a digital representation of the patient's craniofacial anatomy that incorporates multiple data types (e.g., 2D, 3D, and/or 4D data). For example, different data types (e.g., image data obtained using different modalities, such as photographs, scans, x-ray data, MRI data, motion capture data) can be presented as different layers of the combined anatomical model. The different layers can be selectively displayed, hidden, manipulated, etc., to facilitate visualization. The combined anatomical model can be a static model (e.g., a 2D or 3D model showing the patient anatomy in a single pose) or a dynamic model (e.g., an animated model showing the patient anatomy in multiple poses, such as when smiling, speaking, moving the jaws, etc.). The combined anatomical model can be generated in many different ways. In some embodiments, for example, the model is generated by identifying and matching corresponding anatomical landmarks across different data assets. The different data assets can then be aligned, merged, or otherwise combined with each other based on the matched landmarks. For instance, CBCT data can depict both hard and soft tissues of the patient's craniofacial anatomy, and thus can be aligned to models and/or scans of the patient's teeth (e.g., via matching of hard tissue landmarks), as well as image data of the patient's face (e.g., via matching of soft tissue landmarks).

Figure 17C:
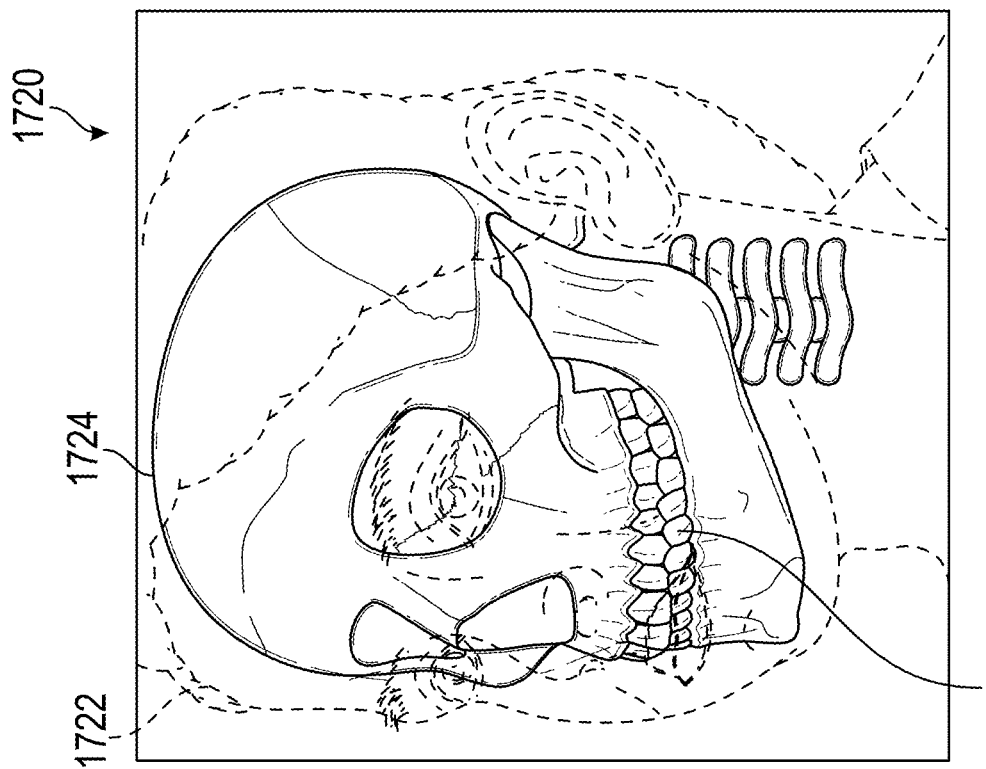
FIGS. 17B and 17C illustrate a combined anatomical model configured in accordance with embodiments of the present technology.
Figure 17B:

FIGS. 17B and 17C illustrate a combined anatomical model 1720 configured in accordance with embodiments of the present technology. In the illustrated embodiment, the model 1720 includes two layers: a first layer 1722 showing the patient's external anatomy (e.g., craniofacial features), and a second layer 1724 showing the patient's internal anatomy (e.g., hard and/or soft tissues). The first layer 1722 can be generated from photographs, videos, scans, etc., of the patient's face, while the second layer 1724 can be generated from x-ray data (e.g., CBCT data), intraoral scan data, MRI data, and/or other suitable imaging modalities for capturing the internal anatomy. Optionally, the second layer 1724 of the combined anatomic model 1720 can be a composite layer in which a digital representation 1726 of the patient's teeth in a planned arrangement (e.g., an initial, intermediate, or target arrangement of a treatment plan) is combined with image data of the remaining portions of the anatomy (e.g., jaws, head). Alternatively, the digital representation 1726 of the teeth can be presented on its own separate layer of the model 1720. Moreover, the model 1720 can include additional layers corresponding to other types of data.

The user can interact with the combined anatomical model 1720 when planning and/or reviewing a treatment plan, as described elsewhere herein. For example, the appearance (e.g., color, opacity) of the layers 1722, 1724 can be adjusted independently to facilitate visualization. In the illustrated embodiment, FIG. 17B shows the first layer 1722 at 100% opacity, while FIG. 17C shows the first layer 1722 at reduced opacity so the second layer 1724 is visible. Optionally, the digital representation 1726 of the teeth can be manipulated by a user to modify the treatment plan, and/or the digital representation 1726 of the teeth can include a heatmap overlay or other graphical representation of changes in tooth mass prescribed by the treatment plan, as described elsewhere herein.

Referring again to FIG. 17A, at block 1708, the method 1700 can continue with outputting a visualization of the combined anatomical model. For example, the visualization can be displayed on a UI produced by a suitable computing system or device, such as the treatment planning component 104 of the system 100 of FIG. 1. The visualization can be displayed to a user (e.g., clinician, technician, patient) to provide visual guidance for planning a treatment procedure, as described elsewhere herein. For example, the visualization can show an initial state of the patient's craniofacial anatomy (e.g., the current anatomy before treatment), a target state of the anatomy (e.g., a simulation of the anatomy once the treatment goal has been achieved), and/or an intermediate state (e.g., a simulation of the anatomy at an intermediate stage of the treatment). The user can interact with the visualization to review and/or modify the treatment plan, in accordance with the techniques described elsewhere herein.

At block 1710, the method 1700 optionally includes generating a treatment plan, based on the combined anatomical model. The treatment plan can be an orthodontic treatment plan, a restorative treatment plan, or an ortho-restorative treatment plan. For example, the treatment plan can include (1) repositioning one or more teeth and/or (2) altering the mass of one or more teeth, as described in greater detail elsewhere herein. In some embodiments, the process of block 1710 includes analyzing the combined anatomical model to automatically detect one or more patient characteristics, such as face type, ethnicity, gender, and/or dental and skeletal class. The patient characteristics can be used as a basis for automated treatment planning, e.g., the treatment plan can account for different ethnicities, genders, face types, etc., in determining a treatment goal for the patient. Alternatively or in combination, the anatomical landmarks identified in block 1704 can also serve as inputs for automated treatment planning. For instance, the anatomical landmarks can be used to calculate facial lines defining a target smile and/or a target tooth arrangement, as previously described.

At block 1712, the method 1700 optionally includes updating the combined anatomical model, based on additional patient data. In some embodiments, the additional patient data includes one or more data assets depicting the patient's anatomy after the treatment procedure has started (e.g., updated photographs, scans, x-rays, etc.). The additional patient data can be incorporated into the combined anatomical model so the model depicts the most recent state of the patient's anatomy. For example, the additional patient data can be merged with the model based on landmark matching, as previously described with respect to blocks 1704 and 1706.

The updated combined anatomical model ("updated model") can be displayed to a user to provide visual guidance for treatment monitoring and progress tracking. For example, the user can review a visualization of the updated model to evaluate any changes that have occurred, such as orthodontic changes (e.g., surgical and non-surgical), restoratives changes, orthognathic changes, facial changes (e.g., changes in facial symmetry), soft tissue changes (e.g., surgical and non-surgical, such as lip support), etc. Alternatively or in combination, the changes can be automatically detected by comparing the anatomical landmarks in the updated model to the corresponding anatomical landmarks in the original model, e.g., using computer vision techniques, machine learning algorithms, and/or other suitable approaches.

The method 1700 can be varied in many different ways. For example, some of the processes shown in FIG. 17A can be omitted (e.g., the processes of blocks 1708, 1710, and/or 1712) and/or the method 1700 can include additional processes not shown in FIG. 17A. Moreover, the method 1700 can be combined with any of the other methods described herein. For instance, some or all of the processes of the method 1700 can be performed as part of the processes of blocks 204 and/or 206 of the method 200 of FIG. 2. Additionally, the method 1700 can implement any of the techniques described with respect to the method 300 of FIG. 3.

Figure 18:
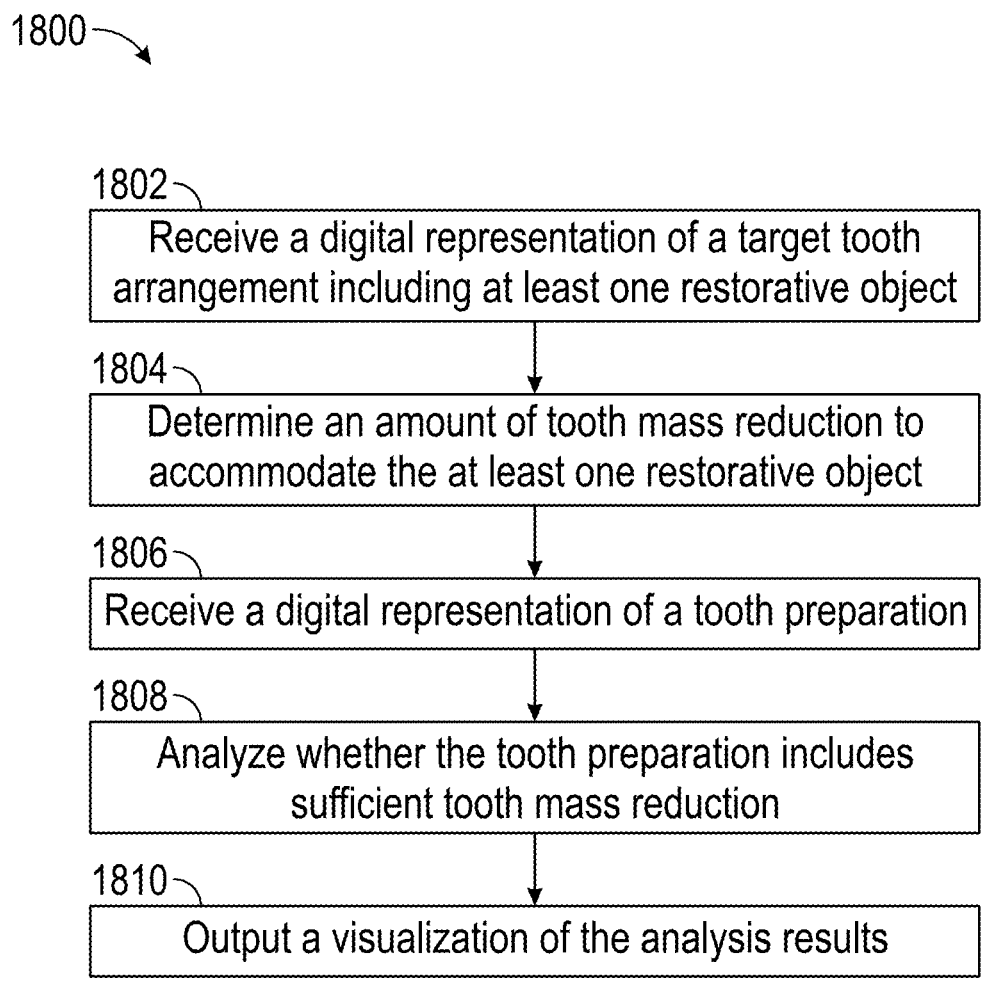
FIG. 18 is a flow diagram illustrating a method for planning a restorative treatment procedure, in accordance with embodiments of the present technology.

FIG. 18 is a flow diagram illustrating a method 1800 for planning a restorative treatment procedure, in accordance with embodiments of the present technology. As described in detail below, the method 1800 can be used to evaluate whether a tooth preparation has sufficient tooth mass reduction to accommodate a desired restorative object (e.g., a crown or other prosthetic). The method 1800 can be performed using any suitable system or device. In some embodiment, some or all of the processes of the method 1800 are implemented as computer-readable instructions (e.g., program code) that are configured to be executed by one or more processors of a computing device. For example, some or all of the processes of the method 1800 can be performed by one or more components of the system 100 of FIG. 1, such as the data input component 102, the treatment planning component 104, and/or the treatment visualization component 106.

The method 1800 begins at block 1802 with receiving a digital representation of a target tooth arrangement for a patient. The target tooth arrangement can be a prescribed arrangement of the teeth configured to achieve the patient's desired aesthetic and/or functional treatment goals (e.g., a target smile), and can be determined using any of the techniques described elsewhere herein. In some embodiments, the target tooth arrangement includes at least one tooth that is modified with at least one restorative object.

At block 1804, the method 1800 can continue with determining an amount of tooth mass reduction to accommodate the at least one restorative object. Tooth mass reduction can be prescribed to create a mounting surface on an existing tooth that fits the restorative object. The appropriate amount of tooth mass reduction can depend on various factors, such as the size of the restorative object, the shape of the restorative object, the type of material used for the restorative object, the thickness requirements of the material used for the restorative object, the shape of the existing tooth, the position of the existing tooth (e.g., the initial position and/or the final position after orthodontic repositioning), the shapes of neighboring teeth, the positions of neighboring teeth (e.g., before and/or after orthodontic repositioning), occlusion, etc.

In some embodiments, the process of block 1804 involves receiving a first digital representation depicting the initial geometry of the tooth, and then generating a second digital representation depicting the tooth with one or more portions removed to accommodate the restorative object ("target tooth preparation"). The amounts and locations of tooth mass reduction in the target tooth preparation can be estimated based on any of the above factors, and can be determined using clinical data, clinical protocols, simulations, trained machine learning algorithms, or suitable combinations thereof.

At block 1806, the method 1800 can include receiving a digital representation of a tooth preparation. The tooth preparation can be an actual tooth of the patient that has undergone tooth mass reduction to accommodate the restorative object(s) prescribed by the target tooth arrangement. The digital representation can include any suitable data that depicts the geometry of the tooth preparation. For example, the digital representation can include scan data and/or surface topography data of the tooth preparation generated via an intraoral scanner. Alternatively or in combination, the digital representation can be produced from other types of patient data, such as photographs, x-ray data, etc.

At block 1808, the method 1800 can include analyzing whether the tooth preparation includes sufficient tooth mass reduction to accommodate the at least one restorative object. This process can involve comparing the digital representation of the actual tooth preparation received in block 1806 to the digital representation of the target tooth preparation generated in block 1804. The comparison can be performed using the tooth mass analysis techniques described above in connection with the method 1300 of FIG. 13. For example, the surfaces of the actual tooth preparation can be compared to the surfaces of the target tooth preparation to identify locations where (1) locations where the actual tooth preparation has added mass compared to the target tooth preparation. (2) locations where the actual tooth preparation has reduced mass compared to the target tooth preparation, and/or (3) locations where the mass of the actual tooth preparation is the same as the mass of the target tooth preparation. The comparison results can then be used to identify locations where the actual tooth preparation should be further reduced, such as any locations where the amount of added mass in the actual tooth preparation relative to the target tooth preparation exceeds a predetermined threshold.

Optionally, at block 1810, the method 1800 includes outputting a visualization of the analysis results of block 1808. The visualization can provide a graphical representation of the differences in mass between the actual tooth preparation and the target tooth preparation, and can therefore assist a user in identifying locations where additional tooth mass reduction may be beneficial or necessary. For example, the visualization can include a heatmap overlaid on a digital representation of the actual tooth preparation (e.g., a 3D model of the patient's current tooth arrangement including the tooth preparation) that graphically displays the differences in tooth mass, similar to the visualization described above in connection with the method 1300 of FIG. 13. The visualization can include indicators marking any locations where additional tooth mass reduction may be needed and/or any other potential issues. In some embodiments, the visualization allows the user to view the analysis results in multiple dimensions (e.g., 3D), thus providing real-time analysis of tooth preparations for evaluating the manufacturability of the corresponding restorations. This approach can avoid restoration failures due to insufficient material thickness, inadequate tooth preparation, and/or other issues, as well as reduce time spent on later adjustments to the restoration and/or tooth preparation.

The method 1800 can be varied in many different ways. For example, some of the processes shown in FIG. 18 can be omitted and/or the method 1800 can include additional processes not shown in FIG. 18. Moreover, the method 1800 can be combined with any of the other methods described herein. For instance, some or all of the processes of the method 1800 can be performed as part of the processes of blocks 204 and/or 206 of the method 200 of FIG. 2. Additionally, the method 1800 can implement any of the techniques described with respect to the method 1300 of FIG. 13.

II. Orthodontic Appliances and Associated Methods

Figure 19A:
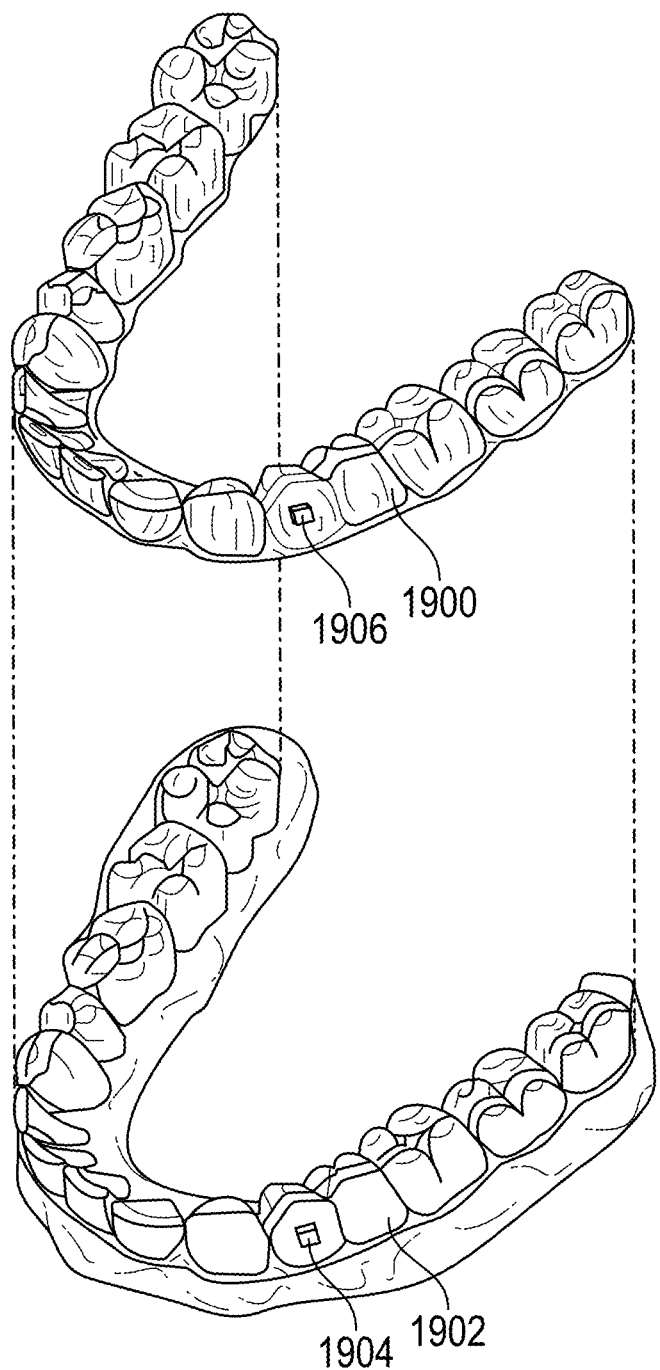
FIG. 19A illustrates a representative example of a tooth repositioning appliance configured in accordance with embodiments of the present technology.

FIG. 19A illustrates a representative example of a tooth repositioning appliance 1900 configured in accordance with embodiments of the present technology. The appliance 1900 can be manufactured and post-processed using any of the systems, methods, and devices described herein. The appliance 1900 (also referred to herein as an "aligner") can be worn by a patient in order to achieve an incremental repositioning of individual teeth 1902 in the jaw. The appliance 1900 can include a shell (e.g., a continuous polymeric shell or a segmented shell) having teeth-receiving cavities that receive and resiliently reposition the teeth. The appliance 1900 or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

The appliance 1900 can fit over all teeth present in an upper or lower jaw, or less than all of the teeth. The appliance 1900 can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance 1900 can be a generic appliance configured to receive the teeth, but not necessarily shaped to match the topography of the patient's teeth. In some cases, only certain teeth received by the appliance 1900 are repositioned by the appliance 1900 while other teeth can provide a base or anchor region for holding the appliance 1900 in place as it applies force against the tooth or teeth targeted for repositioning. In some cases, some, most, or even all of the teeth can be repositioned at some point during treatment. Teeth that are moved can also serve as a base or anchor for holding the appliance as it is worn by the patient. In preferred embodiments, no wires or other means are provided for holding the appliance 1900 in place over the teeth. In some cases, however, it may be desirable or necessary to provide individual attachments 1904 or other anchoring elements on teeth 1902 with corresponding receptacles 1906 or apertures in the appliance 1900 so that the appliance 1900 can apply a selected force on the tooth. Representative examples of appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 19B:
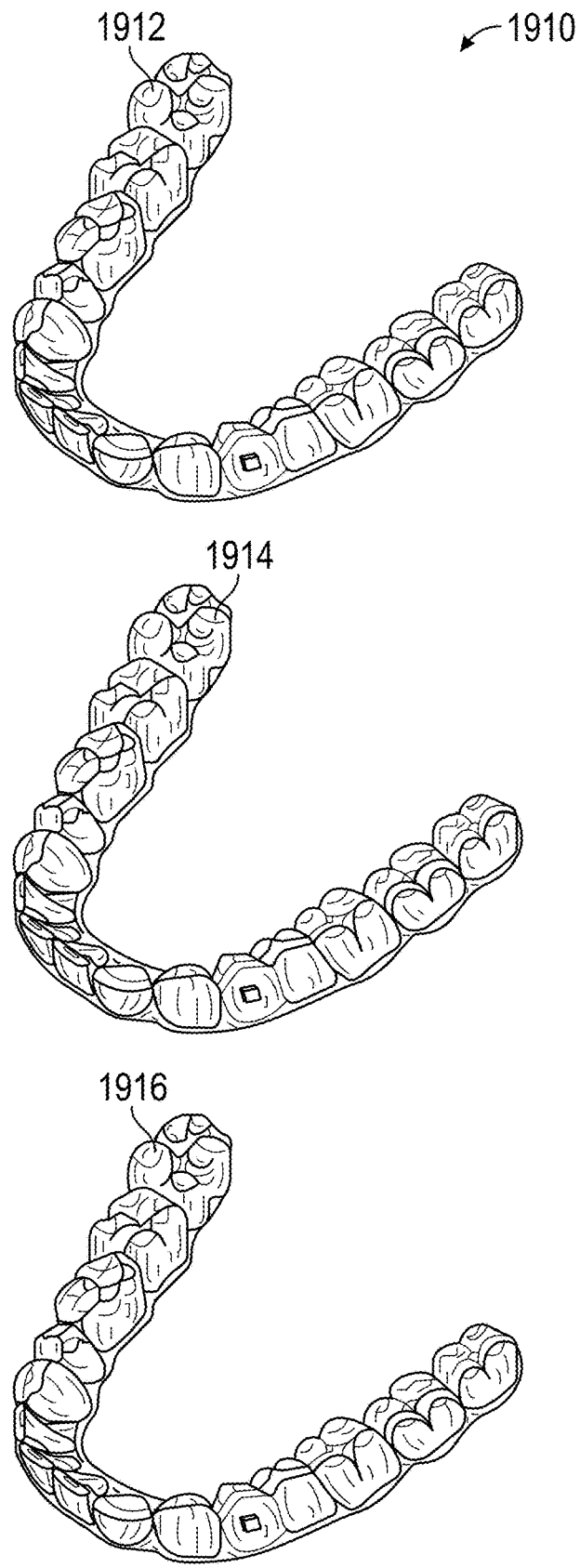
FIG. 19B illustrates a tooth repositioning system including a plurality of appliances, in accordance with embodiments of the present technology.

FIG. 19B illustrates a tooth repositioning system 1910 including a plurality of appliances 1912, 1914, 1916, in accordance with embodiments of the present technology. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 1910 can include a first appliance 1912 corresponding to an initial tooth arrangement, one or more intermediate appliances 1914 corresponding to one or more intermediate arrangements, and a final appliance 1916 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 19C:
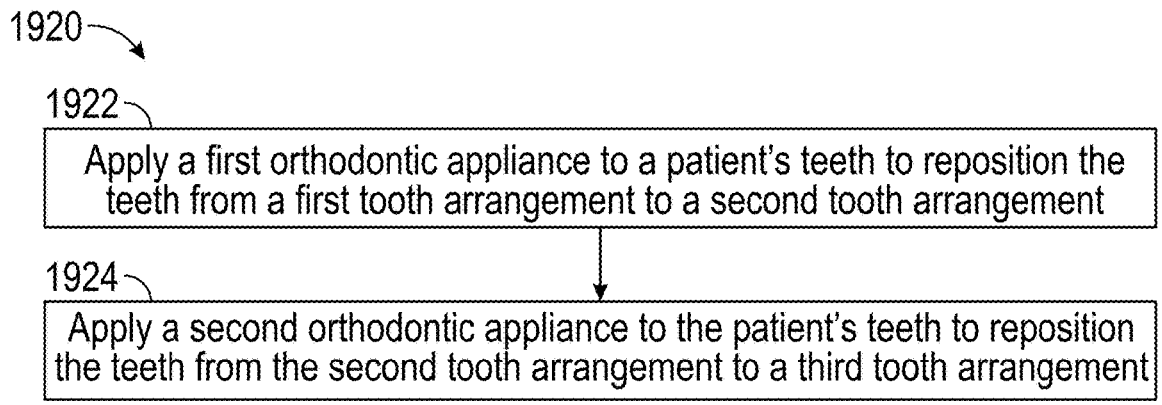
FIG. 19C illustrates a method of orthodontic treatment using a plurality of appliances, in accordance with embodiments of the present technology.

FIG. 19C illustrates a method 1920 of orthodontic treatment using a plurality of appliances, in accordance with embodiments of the present technology. The method 1920 can be practiced using any of the appliances or appliance sets described herein. In block 1922, a first orthodontic appliance is applied to a patient's teeth in order to reposition the teeth from a first tooth arrangement to a second tooth arrangement. In block 1924, a second orthodontic appliance is applied to the patient's teeth in order to reposition the teeth from the second tooth arrangement to a third tooth arrangement. The method 1920 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 20:
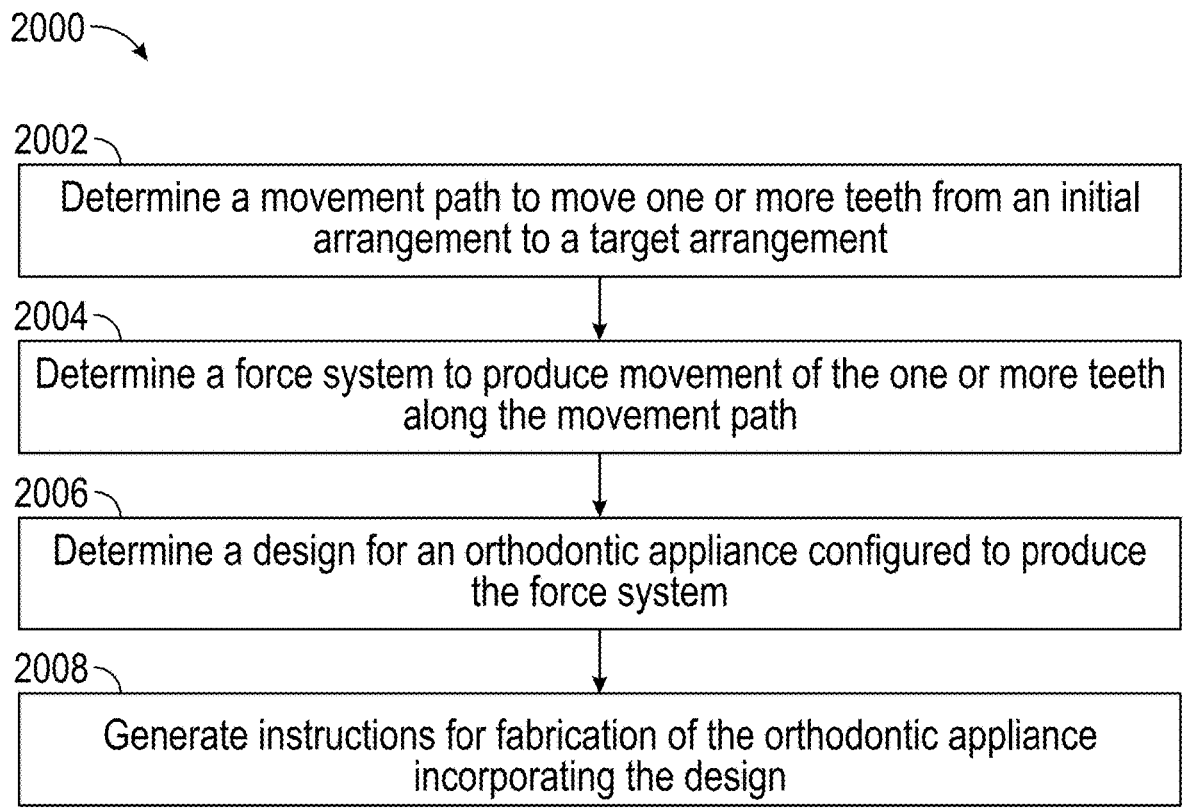
FIG. 20 illustrates a method for designing an orthodontic appliance, in accordance with embodiments of the present technology.

FIG. 20 illustrates a method 2000 for designing an orthodontic appliance, in accordance with embodiments of the present technology. The method 2000 can be applied to any embodiment of the orthodontic appliances described herein. Some or all of the steps of the method 2000 can be performed by any suitable data processing system or device, e.g., one or more processors configured with suitable instructions.

In block 2002, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 2004, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as X-ray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients can require lower forces to expand the suture than older patients, as the suture has not yet fully formed.

In block 2006, a design for an orthodontic appliance configured to produce the force system is determined. The design can include the appliance geometry, material composition and/or material properties, and can be determined in various ways, such as using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the Auto-CAD® software products available from Autodesk, Inc., of San Rafael, CA. For creating finite element models and analyzing them, program products from a number of vendors can be used, including finite element analysis packages from ANSYS, Inc., of Canonsburg, PA, and SIMULIA (Abaqus) software products from Dassault Systèmes of Waltham, MA.

Optionally, one or more designs can be selected for testing or force modeling. As noted above, a desired tooth movement, as well as a force system required or desired for eliciting the desired tooth movement, can be identified. Using the simulation environment, a design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In block 2008, instructions for fabrication of the orthodontic appliance incorporating the design are generated. The instructions can be configured to control a fabrication system or device in order to produce the orthodontic appliance with the specified design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Although the above steps show a method 2000 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 2000 may be performed with any suitable fabrication system or device, such as the embodiments described herein. Some of the steps may be optional, and the order of the steps can be varied as desired.

Figure 21:
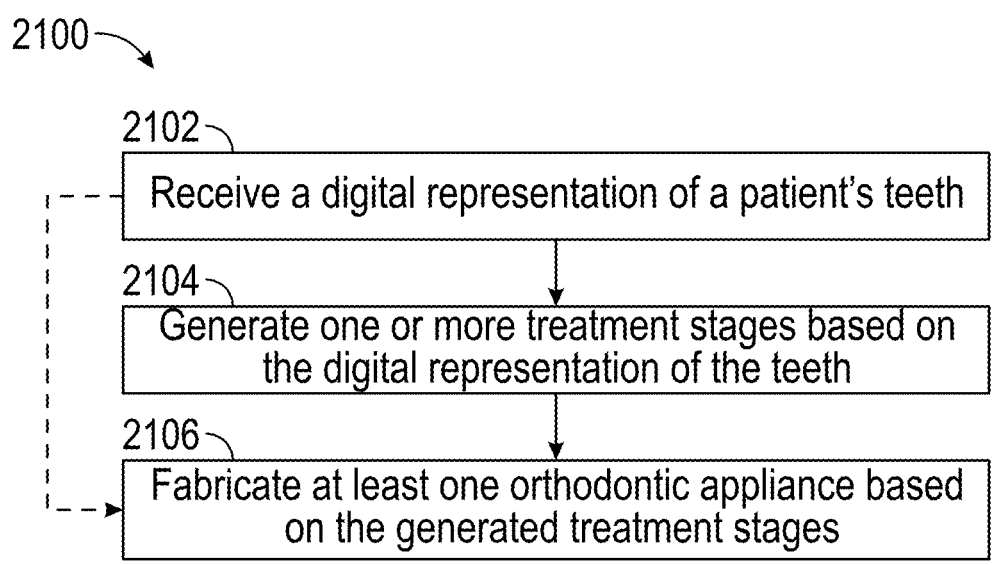
FIG. 21 illustrates a method for digitally planning an orthodontic treatment and/or design or fabrication of an appliance, in accordance with embodiments of the present technology.

FIG. 21 illustrates a method 2100 for digitally planning an orthodontic treatment and/or design or fabrication of an appliance, in accordance with embodiments. The method 2100 can be applied to any of the treatment procedures described herein and can be performed by any suitable data processing system.

In block 2102, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 2104, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 2106, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 21, design and/or fabrication of an orthodontic appliance, and perhaps a particular orthodontic treatment, may include use of a representation of the patient's teeth (e.g., including receiving a digital representation of the patient's teeth (block 2102)), followed by design and/or fabrication of an orthodontic appliance based on a representation of the patient's teeth in the arrangement represented by the received representation.

The techniques described herein can be used for the direct fabrication of dental appliances, such as aligners and/or a series of aligners with tooth-receiving cavities configured to move a person's teeth from an initial arrangement toward a target arrangement in accordance with a treatment plan. Aligners can include mandibular repositioning elements, such as those described in U.S. Pat. No. 10,912,629, entitled "Dental Appliances with Repositioning Jaw Elements," filed Nov. 30, 2015; U.S. Pat. No. 10,537,406, entitled "Dental Appliances with Repositioning Jaw Elements," filed Sep. 19, 2014; and U.S. Pat. No. 9,844,424, entitled "Dental Appliances with Repositioning Jaw Elements," filed Feb. 21, 2014; all of which are incorporated by reference herein in their entirety.

The techniques used herein can also be used to manufacture attachment fabrication templates, e.g., appliances used to position pre-fabricated attachments on a person's teeth in accordance with one or more aspects of a treatment plan. Examples of attachment fabrication templates can be found at least in: U.S. application Ser. No. 17/249,218, entitled, "Flexible 3D Printed Orthodontic Device," filed Feb. 24, 2021; U.S. application Ser. No. 16/366,686, entitled, "Dental Attachment Placement Structure," filed Mar. 27, 2019; U.S. application Ser. No. 15/674,662, entitled, "Devices and Systems for Creation of Attachments," filed Aug. 11, 2017; U.S. Pat. No. 11,103,330, entitled, "Dental Attachment Placement Structure," filed Jun. 14, 2017; U.S. application Ser. No. 14/963,527, entitled, "Dental Attachment Placement Structure," filed Dec. 9, 2015; U.S. application Ser. No. 14/939,246, entitled, "Dental Attachment Placement Structure," filed Nov. 12, 2015; U.S. application Ser. No. 14/939,252, entitled, "Dental Attachment Formation Structures," filed Nov. 12, 2015; and U.S. Pat. No. 9,700,385, entitled, "Attachment Structure," filed Aug. 22, 2014; all of which are incorporated by reference herein in their entirety.

The techniques described herein can be used to make incremental palatal expanders and/or a series of incremental palatal expanders used to expand a person's palate from an initial position toward a target position in accordance with one or more aspects of a treatment plan. Examples of incremental palatal expanders can be found at least in: U.S. application Ser. No. 16/380,801, entitled, "Releasable Palatal Expanders," filed Apr. 10, 2019; U.S. application Ser. No. 16/022,552, entitled, "Devices, Systems, and Methods for Dental Arch Expansion," filed Jun. 28, 2018; U.S. Pat. No. 11,045,283, entitled, "Palatal Expander with Skeletal Anchorage Devices," filed Jun. 8, 2018; U.S. application Ser. No. 15/831,159, entitled "Palatal Expanders and Methods of Expanding a Palate," filed Dec. 4, 2017; U.S. Pat. No. 10,993,783, entitled, "Methods and Apparatuses for Customizing a Rapid Palatal Expander," filed Dec. 4, 2017; and U.S. Pat. No. 7,192,273, entitled, "System and Method for Palatal Expansion," filed Aug. 7, 2003; all of which are incorporated by reference herein in their entirety.

EXAMPLES

The following examples are included to further describe some aspects of the present technology, and should not be used to limit the scope of the technology.

1. A method comprising:
  receiving a treatment plan comprising a target tooth arrangement and a plurality of intermediate tooth arrangements configured to adjust a patient's teeth from an initial tooth arrangement toward the target tooth arrangement, wherein the target tooth arrangement comprises a change in mass of at least one tooth; and
  outputting a graphical user interface comprising a visualization of the treatment plan, wherein the visualization comprises:
    a plurality of digital models, each digital model representing a corresponding intermediate tooth arrangement of the plurality of intermediate tooth arrangements, and
    a heatmap overlaid onto at least one digital model of the plurality of digital models, wherein the heatmap shows a difference in tooth mass between the target tooth arrangement and the corresponding at least one intermediate tooth arrangement of the at least one digital model.

2. The method of Example 1, wherein the change in mass of the at least one tooth comprises a tooth mass addition, a tooth mass reduction, or a combination thereof.

3. The method of Example 1 or 2, wherein the target tooth arrangement comprises at least one restorative object applied to the at least one tooth.

4. The method of Example 3, wherein the at least one restorative object comprises one or more of the following: a crown, a veneer, edge bonding, a composite, an implant, or a prosthetic.

5. The method of Example 3 or 4, wherein the visualization comprises a restoratives model overlaid onto the at least one digital model and representing the at least one restorative object.

6. The method of Example 5, further comprising receiving user input adjusting an opacity of the restoratives model.

7. The method of any one of Examples 1 to 6, wherein the heatmap shows locations and amounts of tooth mass reduction.

8. The method of any one of Examples 1 to 7, wherein the heatmap shows locations and amounts of tooth mass addition.

9. The method of any one of Examples 1 to 8, wherein the heatmap comprises a plurality of colors representing distances between a surface of the at least one intermediate tooth arrangement and a surface of the target tooth arrangement.

10. The method of Example 9, wherein the plurality of colors comprise a first set of colors representing tooth mass reduction grades, and a second set of colors representing tooth mass addition grades.

11. The method of any one of Examples 1 to 10, wherein the heatmap shows a difference in tooth mass between each of the plurality of intermediate tooth arrangements and the target tooth arrangement.

12. The method of any one of Examples 1 to 11, further comprising:
  receiving user input indicating a modification to the treatment plan, and
  updating the heatmap based on the modification.

13. The method of Example 12, wherein the modification comprises one or more of the following: an adjustment to a position of a tooth, an addition of a restorative object to a tooth, a removal of a restorative object from a tooth, an adjustment to a position of a restorative object, an adjustment to a shape of a restorative object, or an adjustment to a gingival margin.

14. The method of any one of Examples 1 to 13, wherein the visualization comprises a patient image.

15. The method of Example 14, wherein the visualization shows one or more smile lines overlaid onto the patient image.

16. The method of Example 15, wherein the one or more smile lines represent parameters of a target smile for the patient.

17. The method of Example 15 or 16, wherein the one or more smile lines comprise one or more of the following: a facial midline, an intercanine width line, a gingival line, an incisal edge line, a horizontal line, or a tooth outline.

18. The method of any one of Examples 15 to 17, further comprising receiving user input modifying the one or more smile lines.

19. The method of any one of Examples 1 to 18, wherein the visualization comprises a composite image comprising the at least one digital model overlaid onto an image of the patient's face.

20. The method of Example 19, further comprising:
  receiving user input indicating a modification to the treatment plan, and
  updating the composite image based on the modification.

21. A system for planning a treatment for a patient's teeth, the system comprising:
  one or more processors; and
  a memory operably coupled to the one or more processors and storing instructions that, when executed by the one or more processors, cause the system to perform operations comprising:
    receiving a treatment plan comprising a target tooth arrangement and a plurality of intermediate tooth arrangements configured to adjust the patient's teeth from an initial tooth arrangement toward the target tooth arrangement, wherein the target tooth arrangement comprises a change in mass of at least one tooth, and
    outputting a graphical user interface comprising a visualization of the treatment plan, wherein the visualization comprises:
      a plurality of digital models, each digital model representing a corresponding intermediate tooth arrangement of the plurality of intermediate tooth arrangements, and
      a heatmap overlaid onto at least one digital model of the plurality of digital models, wherein the heatmap shows a difference in tooth mass between the target tooth arrangement and the corresponding at least one intermediate tooth arrangement of the at least one digital model.

22. A non-transitory computer-readable storage medium comprising instructions that, when executed by one or more processors of a computing system, cause the computing system to perform operations comprising:
receiving a treatment plan comprising a target tooth arrangement and a plurality of intermediate tooth arrangements configured to adjust a patient's teeth from an initial tooth arrangement toward the target tooth arrangement, wherein the target tooth arrangement comprises a change in mass of at least one tooth; and
outputting a graphical user interface comprising a visualization of the treatment plan, wherein the visualization comprises:
a plurality of digital models, each digital model representing a corresponding intermediate tooth arrangement of the plurality of intermediate tooth arrangements, and
a heatmap overlaid onto at least one digital model of the plurality of digital models, wherein the heatmap shows a difference in tooth mass between the target tooth arrangement and the corresponding at least one intermediate tooth arrangement of the at least one digital model.

23. A method comprising:
receiving input data representing an initial tooth arrangement of a patient's teeth;
determining a target tooth arrangement for the patient's teeth, wherein the target tooth arrangement comprises a change in mass of at least one tooth;
generating a plurality of intermediate tooth arrangements configured to adjust the patient's teeth from the initial tooth arrangement toward the target tooth arrangement; and
generating instructions to output a visualization showing a difference in tooth mass between at least one intermediate tooth arrangement of the plurality of intermediate tooth arrangements and the target tooth arrangement.

24. The method of Example 23, wherein the change in the mass of the at least one tooth comprises addition of a restorative object to adjust a shape of an existing tooth or to replace a missing tooth.

25. The method of Example 24, wherein the restorative object comprises a temporary restoration or a permanent restoration.

26. The method of Example 24 or 25, wherein the restorative object comprises a crown, a veneer, edge bonding, a composite, an implant, or a prosthetic.

27. The method of any one of Examples 23 to 26, wherein the change in the mass of the at least one tooth comprises removal of a portion of an existing tooth.

28. The method of any one of Examples 23 to 27, wherein determining the target tooth arrangement comprises:
determining a tooth arrangement to be achieved through orthodontic repositioning; and
generating the target tooth arrangement by applying one or more restorative adjustments to the tooth arrangement.

29 The method of Example 28, wherein the one or more restorative adjustments comprise changing a shape of a tooth in the tooth arrangement.

30. The method of Example 28 or 29, wherein the one or more restorative adjustments are determined based on unique facial features of the patient.

31. The method of any one of Examples 28 to 30, wherein the one or more restorative adjustments are determined based on a plurality of facial lines defining a target smile for the patient.

32. The method of any one of Examples 23 to 31, further comprising comparing the at least one intermediate tooth arrangement to the target tooth arrangement to determine the difference in tooth mass.

33. The method of Example 32, wherein the comparing comprises measuring a distance between a surface of the at least one intermediate tooth arrangement and a surface of the target tooth arrangement.

34. The method of Example 32 or 33, wherein the comparing comprises identifying a region of a tooth in the at least one intermediate tooth arrangement that is protruded or recessed relative to a corresponding region of the tooth in the target tooth arrangement.

35. The method of any one of Examples 23 to 34, wherein the visualization comprises a heatmap overlay.

36 The method of any one of Examples 23 to 35, further comprising:
receiving user input indicating a modification to the target tooth arrangement,
generating a modified target tooth arrangement based on the modification, and
generating instructions to update the visualization to show a difference in tooth mass between the at least one intermediate tooth arrangement and the modified target tooth arrangement.

37 The method of Example 36, wherein the modification comprises one or more of the following: an adjustment to a position of a tooth, an addition of a restorative object to a tooth, a removal of a restorative object from a tooth, an adjustment to a position of a restorative object, an adjustment to a shape of a restorative object, or an adjustment to a gingival margin.

38 The method of any one of Examples 23 to 37, further comprising generating instructions for manufacturing a plurality of orthodontic appliances configured to adjust the patient's teeth from the initial tooth arrangement toward the target tooth arrangement.

39. The method of Example 38, wherein the plurality of orthodontic appliances comprise a plurality of polymeric shell aligners.

40. The method of any one of Examples 23 to 39, further comprising generating instructions for applying or manufacturing a restorative object corresponding to change in the mass of the at least one tooth.

41. The method of any one of Examples 23 to 40, further comprising:
receiving user input indicating a selected intermediate tooth arrangement of the plurality of intermediate tooth arrangements, and
generating a treatment plan for the patient, wherein the treatment plan comprises: (1) a plurality of orthodontic appliances configured to reposition the patient's teeth from the initial tooth arrangement toward the selected intermediate tooth arrangement, and (2) one or more restorative procedures configured to compensate for a difference in tooth mass between the selected intermediate tooth arrangement and the target tooth arrangement.

42. The method of Example 41, wherein the treatment plan comprises: (1) a shorter duration compared to an alternative treatment plan in which the patient's teeth are repositioned from the initial tooth arrangement toward the target tooth arrangement, and (2) a larger change in the mass of the at least one tooth compared to the alternative treatment plan.

43. The method of any one of Examples 23 to 42, further comprising:
receiving image data of the patient's face,
determining one or more facial lines based on the image data, and
generating the target tooth arrangement based on the one or more facial lines.

44. The method of Example 43, wherein the image data comprises a single image.

45. The method of Example 43, wherein the image data comprises a plurality of images.

46 The method of Example 45, wherein the plurality of images comprise image frames of a video.

47. The method of Example 45 or 46, further comprising selecting at least one image from the plurality of images, wherein the one or more facial lines are determined using the at least one image.

48. The method of Example 47, wherein the at least one image is selected based on one or more of the following criteria: position of the patient's head, position of the patient's mouth, visibility of the patient's face, visibility of the patient's teeth, clarity of the patient's mouth, resolution of the patient's mouth, or whether the patient's eyes are open.

49. The method of any one of Examples 43 to 48, further comprising adjusting the image data to a vertical orientation before determining the one or more facial lines.

50. The method of any one of Examples 43 to 49, wherein determining the one or more facial lines comprises:
identifying a plurality of facial landmarks in the image data, and
determining the one or more facial lines based on the plurality of facial landmarks.

51. The method of any one of Examples 43 to 50, wherein the one or more facial lines define a target smile for the patient.

52. The method of any one of Examples 43 to 51, where the one or more facial lines comprise one or more of the following: a facial midline, an intercanine width line, an incisal edge line, a gingival edge line, a horizontal line, or a tooth outline.

53 The method of any one of Examples 43 to 52, wherein the visualization comprises the one or more facial lines.

54. The method of Example 53, wherein the visualization is overlaid onto the image data of the patient's face.

55. The method of Example 53 or 54, further comprising receiving user input indicating a modification to the one or more facial lines.

56. The method of any one of Examples 23 to 55, wherein the input data comprises one or more of the following: images, videos, scan data, MRI data, CT data, CBCT data, or motion data.

57. The method of any one of Examples 23 to 56, wherein the input data comprises one or more of the following: 2D data, 3D data, or 4D data.

58. The method of Example 56 or 57, further comprising generating a combined anatomical model based on the input data, wherein the visualization comprises the combined anatomical model.

59. The method of Example 58, wherein the combined anatomical model comprises a plurality of layers, and wherein at least some of the plurality of layers are generated using different data types.

60 The method of Example 58 or 59, wherein the combined anatomical model is a static model.

61. The method of Example 58 or 59, wherein the combined anatomic model is a dynamic model.

62. The method of any one of Examples 56 to 61, further comprising generating a digital representation of the initial tooth arrangement based on the input data.

63. The method of any one of Examples 56 to 62, further comprising determining one or more craniofacial landmarks based on the input data.

64. The method of Example 63, further comprising determining a target smile based on the one or more craniofacial landmarks.

65. The method of any one of Examples 23 to 64, wherein the input data comprises a patient image that is automatically selected from a video.

66. The method of any one of Examples 23 to 65, wherein the input data comprises a patient image that is automatically selected using a trained machine learning algorithm.

67. A system for planning a treatment for a patient's teeth, the system comprising:
one or more processors; and
a memory operably coupled to the one or more processors and storing instructions that, when executed by the one or more processors, cause the system to perform operations comprising:
receiving input data representing an initial tooth arrangement of the patient's teeth,
determining a target tooth arrangement for the patient's teeth, wherein the target arrangement comprises a change in mass of at least one tooth,
generating a plurality of intermediate tooth arrangements configured to adjust the patient's teeth from the initial tooth arrangement toward the target tooth arrangement, and
generating instructions to output a visualization showing a difference in tooth mass between at least one intermediate tooth arrangement of the plurality of intermediate tooth arrangements and the target tooth arrangement.

68. A non-transitory computer-readable storage medium comprising instructions that, when executed by one or more processors of a computing system, cause the computing system to perform operations comprising:
receiving input data representing an initial tooth arrangement of a patient's teeth;
determining a target tooth arrangement for the patient's teeth, wherein the target tooth arrangement comprises a change in mass of at least one tooth;
generating a plurality of intermediate tooth arrangements configured to adjust the patient's teeth from the initial tooth arrangement toward the target tooth arrangement; and
generating instructions to output a visualization showing a difference in tooth mass between at least one intermediate tooth arrangement of the plurality of tooth arrangements and the target tooth arrangement.

69. A method comprising:
receiving an image of a patient's face;
determining a plurality of facial lines using the image of the patient's face, wherein the plurality of facial lines represent a target smile for the patient; and
outputting a visualization comprising the plurality of facial lines overlaid onto a composite image, wherein the composite image comprises the image of the patient's face combined with a digital model of the patient's teeth, and wherein the digital model represents a tooth arrangement of a treatment plan to adjust the patient's teeth from an initial arrangement toward a target tooth arrangement corresponding to the target smile.

70. The method of Example 69, further comprising selecting the image from a plurality of images of the patient's face.

71. The method of Example 70, wherein the plurality of images comprise image frames of a video.

72. The method of Example 70 or 71, wherein the image is selected using a machine learning algorithm.

73. The method of any one of Examples 70 to 72, wherein the image is selected based on one or more of the following criteria: position of the patient's head, position of the patient's mouth, visibility of the patient's face, visibility of the patient's teeth, clarity of the patient's mouth, resolution of the patient's mouth, or whether the patient's eyes are open.

74. The method of any one of Examples 69 to 73, further comprising adjusting the image before determining the plurality of facial lines.

75. The method of Example 74, wherein adjusting the image comprises rotating the image to a vertical orientation.

76. The method of Example 75, wherein rotating the image to the vertical orientation comprises:
    identifying a set of first facial landmarks in the image,
    generating a mirrored image comprising a set of second facial landmarks,
    matching each first facial landmark to a corresponding second facial landmark by one or more of rotating or translating the mirrored image,
    determining a matching angle for the mirrored image, and rotating the image by the matching angle.

77. The method of any one of Examples 69 to 76, wherein determining the plurality of facial lines comprises:
    identifying a plurality of facial landmarks in the image, and
    determining the plurality of facial lines based on the plurality of facial landmarks.

78. The method of Example 77, wherein determining the plurality of facial lines comprises:
    determining a face type of the patient,
    calculating one or more orthodontic parameters based on the face type, and
    determining at least some of the facial lines based on the one or more orthodontic parameters.

79. The method of Example 78, wherein the one or more orthodontic parameters are calculated using a continuous function relating a value of the one or more orthodontic parameters to the face type of the patient.

80. The method of any one of Examples 69 to 79, where the plurality of facial lines comprise one or more of the following: a facial midline, an intercanine width line, an incisal edge line, a gingival edge line, a horizontal line, or a tooth outline.

81. The method of any one of Examples 69 to 80, further comprising receiving user input indicating a modification to at least one facial line.

82. The method of any one of Examples 69 to 81, wherein the visualization comprises a plurality of digital models representing a plurality of intermediate tooth arrangements configured to adjust a patient's teeth from the initial tooth arrangement toward the target tooth arrangement.

83. The method of Example 82, wherein the target tooth arrangement comprises a change in mass of at least one tooth.

84. The method of Example 83, wherein the change in the mass of the at least one tooth comprises one or more of a tooth mass addition or a tooth mass reduction.

85. The method of Example 83 or 84, wherein the change in the mass of the at least one tooth comprises addition of a restorative object to adjust a shape of an existing tooth or to replace a missing tooth.

86. The method of Example 85, wherein the restorative object comprises a crown, a veneer, edge bonding, a composite, an implant, or a prosthetic.

87. The method of any one of Examples 82 to 86, wherein the composite image is displayed concurrently with at least one digital model of the plurality of digital models.

88 The method of any one of Examples 82 to 87, further comprising receiving user input indicating a modification to the target tooth arrangement, wherein the modification is generated based on the plurality of facial lines.

89. A system for planning a treatment for a patient's teeth, the system comprising:
    a processor; and
    a memory operably coupled to the processor and storing instructions that, when executed by the processor, cause the system to perform operations comprising:
        receiving an image of the patient's face,
        determining a plurality of facial lines using the image of the patient's face, wherein the plurality of facial lines represent a target smile for the patient, and
        outputting a visualization comprising the plurality of facial lines overlaid onto a composite image, wherein the composite image comprises the image of the patient's face combined with a digital model of the patient's teeth, and wherein the digital model represents a tooth arrangement of a treatment plan to adjust the patient's teeth from an initial arrangement toward a target tooth arrangement corresponding to the target smile.

90. A non-transitory computer-readable storage medium comprising instructions that, when executed by one or more processors of a computing system, cause the computing system to perform operations comprising:
    receiving an image of a patient's face;
    determining a plurality of facial lines using the image of the patient's face, wherein the plurality of facial lines represent a target smile for the patient; and
    outputting a visualization comprising the plurality of facial lines overlaid onto a composite image, wherein the composite image comprises the image of the patient's face combined with a digital model of the patient's teeth, and wherein the digital model represents a tooth arrangement of a treatment plan to adjust the patient's teeth from an initial arrangement toward a target tooth arrangement corresponding to the target smile.

91. A method comprising:
    receiving a digital representation of a target tooth arrangement for a patient's teeth, wherein the target tooth arrangement includes at least one tooth that is modified with at least one restorative object;
    determining a target tooth preparation for the at least one tooth to accommodate the at least one restorative object;
    receiving a digital representation of an actual tooth preparation of the at least one tooth; and
    outputting a visualization showing a difference in tooth mass between the target tooth preparation and the actual tooth preparation.

92. The method of Example 91, wherein the at least one restorative object comprises a temporary restoration or a permanent restoration.

93. The method of Example 91 or 92, wherein the at least one restorative object comprises one or more of a crown, a veneer, edge bonding, a composite, an implant, or a prosthetic.

94. The method of any one of Examples 91 to 93, wherein the target tooth preparation comprises tooth mass reduction to accommodate the at least one restorative object.

95. The method of Example 94, wherein the tooth mass reduction is configured to create a mounting surface on the at least one tooth for the at least one restorative object.

96. The method of any one of Examples 91 to 95, wherein determining the target tooth preparation comprises:
   receiving a first digital representation depicting an initial geometry of the at least one tooth,
   generating a second digital representation depicting the at least one tooth with one or more portions removed to accommodate the at least one restorative object.

97 The method of any one of Examples 91 to 96, wherein the digital representation of the actual tooth preparation comprises intraoral scan data.

98. The method of any one of Examples 91 to 97, further comprising determining the difference in tooth mass by comparing the digital representation of the target tooth representation to the digital representation of the actual tooth preparation.

99. The method of Example 98, wherein the comparing comprises measuring a distance between a surface of the actual tooth preparation and a surface of the target tooth preparation.

100. The method of Example 98 or 99, wherein the comparing comprises identifying a region of the at least one tooth in the actual tooth preparation that is protruded or recessed relative to a corresponding region of the at least one tooth in the target tooth preparation.

101. The method of any one of Examples 91 to 100, wherein the visualization comprises a heatmap overlay showing the difference in tooth mass.

102. The method of Example 101, wherein the heatmap comprises a plurality of colors representing distances between a surface of the actual tooth preparation and a surface of the target tooth preparation.

103. The method of any one of Examples 91 to 102, further comprising identifying one or more locations in the actual tooth preparation where additional tooth mass reduction is prescribed.

104. The method of Example 103, wherein the one or more locations comprise added mass relative to the target tooth preparation that exceeds a predetermined threshold.

105. The method of Example 103 or 104, wherein the visualization includes one or more indicators marking the one or more locations.

106. A system for planning a treatment for a patient's teeth, the system comprising:
   a processor; and
   a memory operably coupled to the processor and storing instructions that, when executed by the processor, cause the system to perform operations comprising:
      receiving a digital representation of a target tooth arrangement for the patient's teeth, wherein the target tooth arrangement includes at least one tooth that is modified with at least one restorative object,
      determining a target tooth preparation for the at least one tooth to accommodate the at least one restorative object,
      receiving a digital representation of an actual tooth preparation of the at least one tooth, and
      outputting a visualization showing a difference in tooth mass between the target tooth preparation and the actual tooth preparation.

107. A non-transitory computer-readable storage medium comprising instructions that, when executed by one or more processors of a computing system, cause the computing system to perform operations comprising:
   receiving a digital representation of a target tooth arrangement for a patient's teeth, wherein the target tooth arrangement includes at least one tooth that is modified with at least one restorative object;
   determining a target tooth preparation for the at least one tooth to accommodate the at least one restorative object;
   receiving a digital representation of an actual tooth preparation of the at least one tooth; and
   outputting a visualization showing a difference in tooth mass between the target tooth preparation and the actual tooth preparation.

CONCLUSION

Although many of the embodiments are described above with respect to systems, devices, and methods for ortho-restorative treatment planning, the technology is applicable to other applications and/or other approaches, such as other types of dental treatments (e.g., orthodontics-only treatments, restorative-only treatments) or other types of treatments applied to a patient's craniofacial region (e.g., orthognathic treatments, plastic surgery, cosmetics). Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-21.

The various processes described herein can be partially or fully implemented using program code including instructions executable by one or more processors of a computing system for implementing specific logical functions or steps in the process. The program code can be stored on any type of computer-readable medium, such as a storage device including a disk or hard drive. Computer-readable media containing code, or portions of code, can include any appropriate media known in the art, such as non-transitory computer-readable storage media. Computer-readable media can include volatile and non-volatile, removable and non-removable media implemented in any method or technology for storage and/or transmission of information, including, but not limited to, random-access memory (RAM), read-only memory (ROM), electrically erasable programmable read-only memory (EEPROM), flash memory, or other memory technology; compact disc read-only memory (CD-ROM), digital video disc (DVD), or other optical storage; magnetic cassettes, magnetic tape, magnetic disk storage, or other magnetic storage devices; solid state drives (SSD) or other solid state storage devices; or any other medium which can be used to store the desired information and which can be accessed by a system device.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially." "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

To the extent any materials incorporated herein by reference conflict with the present disclosure, the present disclosure controls.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method comprising:
   receiving input data representing an initial tooth arrangement of a patient's teeth;
   determining a target tooth arrangement for the patient's teeth, wherein the target tooth arrangement comprises a change in mass of at least one tooth;
   generating a plurality of intermediate tooth arrangements configured to adjust the patient's teeth from the initial tooth arrangement toward the target tooth arrangement;
   generating instructions to output a first heatmap showing a difference in tooth mass between a first intermediate tooth arrangement of the plurality of intermediate tooth arrangements and the target tooth arrangement;
   generating instructions to output a second heatmap showing a difference in tooth mass between a second intermediate tooth arrangement of the plurality of intermediate tooth arrangements and the target tooth arrangement; and
   receiving a user input selecting the first intermediate tooth arrangement or the second intermediate tooth arrangement for use in a treatment plan based on a comparison between the first heatmap and the second heatmap.

2. The method of claim 1, wherein the change in the mass of the at least one tooth comprises addition of a restorative object to adjust a shape of an existing tooth or to replace a missing tooth.

3. The method of claim 2, wherein the restorative object comprises a temporary restoration or a permanent restoration.

4. The method of claim 2, wherein the restorative object comprises a crown, a veneer, edge bonding, a composite, an implant, or a prosthetic.

5. The method of claim 1, wherein the change in the mass of the at least one tooth comprises removal of a portion of an existing tooth.

6. The method of claim 1, wherein determining the target tooth arrangement comprises:
   determining a tooth arrangement to be achieved through orthodontic repositioning; and
   generating the target tooth arrangement by applying one or more restorative adjustments to the tooth arrangement.

7. The method of claim 6, wherein the one or more restorative adjustments comprise changing a shape of a tooth in the tooth arrangement.

8. The method of claim 6, wherein the one or more restorative adjustments are determined based on unique facial features of the patient.

9. The method of claim 6, wherein the one or more restorative adjustments are determined based on a plurality of facial lines defining a target smile for the patient.

10. The method of claim 1, further comprising determining the differences in tooth mass for each of the first intermediate tooth arrangement and the second intermediate tooth arrangement with respect to the target tooth arrangement.

11. The method of claim 10, wherein determining the differences in tooth mass comprises:
    measuring a first distance between a surface of the first intermediate tooth arrangement and a surface of the target tooth arrangement, and
    measuring a second distance between a surface of the second intermediate tooth arrangement and a surface of the target tooth arrangement.

12. The method of claim 10, wherein determining the differences in tooth mass comprises identifying a region of a tooth in at least one of the first intermediate tooth arrangement or the second intermediate tooth arrangement that is protruded or recessed relative to a corresponding region of the tooth in the target tooth arrangement.

13. The method of claim 1, further comprising:
    receiving user input indicating a modification to the target tooth arrangement,
    generating a modified target tooth arrangement based on the modification, and
    generating instructions to update the visualization to show a difference in tooth mass between the modified target tooth arrangement and at least one of the first intermediate tooth arrangement or the second intermediate tooth arrangement.

14. The method of claim 13, wherein the modification comprises one or more of the following: an adjustment to a position of a tooth, an addition of a restorative object to a tooth, a removal of a restorative object from a tooth, an adjustment to a position of a restorative object, an adjustment to a shape of a restorative object, or an adjustment to a gingival margin.

15. The method of claim 1, further comprising generating instructions for manufacturing a plurality of orthodontic appliances configured to adjust the patient's teeth from the initial tooth arrangement toward the target selected intermediate tooth arrangement.

16. The method of claim 15, wherein the plurality of orthodontic appliances comprise a plurality of polymeric shell aligners.

17. The method of claim 1, further comprising generating instructions for applying or manufacturing a restorative object corresponding to the change in mass of the at least one tooth.

18. The method of claim 1, further comprising:
generating the treatment plan for the patient, wherein the treatment plan comprises: (1) a plurality of orthodontic appliances configured to reposition the patient's teeth from the initial tooth arrangement toward the selected intermediate tooth arrangement, and (2) one or more restorative procedures configured to compensate for a difference in tooth mass between the selected intermediate tooth arrangement and the target tooth arrangement.

19. The method of claim 18, wherein the treatment plan comprises: (1) a shorter duration compared to an alternative treatment plan in which the patient's teeth are repositioned from the initial tooth arrangement toward the target tooth arrangement, and (2) a larger change in the mass of the at least one tooth compared to the alternative treatment plan.

20. The method of claim 1, wherein at least one of the first heatmap or the second heatmap comprises a first set of colors representing tooth mass reduction grades, and a second set of colors representing tooth mass addition grades.

* * * * *

UNITED STATES PATENT AND TRADEMARK OFFICE
CERTIFICATE OF CORRECTION

PATENT NO. : 12,220,288 B2
APPLICATION NO. : 18/050284
DATED : February 11, 2025
INVENTOR(S) : Dmitry Yurievich Chekh et al.

Page 1 of 1

It is certified that error appears in the above-identified patent and that said Letters Patent is hereby corrected as shown below:

In the Claims

In Column 55, in Claim 15, Line 2, after "toward the" delete "target".

Signed and Sealed this
Eighteenth Day of March, 2025

Coke Morgan Stewart
*Acting Director of the United States Patent and Trademark Office*